US011135163B2

(12) United States Patent
Sun et al.

(10) Patent No.: US 11,135,163 B2
(45) Date of Patent: Oct. 5, 2021

(54) PEPTIDE HYDROGEL PROPERTIES AND ITS APPLICATIONS

(71) Applicant: Kansas State University Research Foundation, Manhattan, KS (US)

(72) Inventors: Xiuzhi S. Sun, Manhattan, KS (US); Hongzhou Huang, Manhattan, KS (US); Tiffany L. Carter, Kansas City, MO (US); Mark L. Weiss, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 34 days.

(21) Appl. No.: 16/109,119

(22) Filed: Aug. 22, 2018

(65) Prior Publication Data
US 2018/0353428 A1 Dec. 13, 2018

Related U.S. Application Data

(62) Division of application No. 15/316,398, filed as application No. PCT/US2015/034409 on Jun. 5, 2015, now abandoned.

(60) Provisional application No. 62/008,140, filed on Jun. 5, 2014.

(51) Int. Cl.
| | |
|---|---|
| A61K 9/06 | (2006.01) |
| A61K 38/00 | (2006.01) |
| A61L 24/00 | (2006.01) |
| A61L 24/10 | (2006.01) |

(52) U.S. Cl.
CPC .............. *A61K 9/06* (2013.01); *A61K 38/00* (2013.01); *A61L 24/0031* (2013.01); *A61L 24/108* (2013.01); *A61L 2400/04* (2013.01); *C12N 2513/00* (2013.01); *C12N 2533/50* (2013.01)

(58) Field of Classification Search
CPC .................................. A61K 9/06; A61K 38/00
See application file for complete search history.

(56) References Cited

U.S. PATENT DOCUMENTS

| 5,177,060 | A | 1/1993 | Wei | |
|---|---|---|---|---|
| 7,745,570 | B2 | 6/2010 | Tomich et al. | |
| 8,722,850 | B2 | 5/2014 | Vescovi et al. | |
| 8,835,395 | B2 * | 9/2014 | Sun | A61L 27/22 |
| | | | | 514/21.4 |
| 8,883,967 | B2 | 11/2014 | Tomich et al. | |
| 9,943,592 | B2 | 4/2018 | Sun et al. | |
| 2009/0105449 | A1 | 4/2009 | Tomich et al. | |
| 2011/0150844 | A1 * | 6/2011 | Ellis-Behnke | A61K 38/10 |
| | | | | 424/93.7 |
| 2011/0230911 | A1 | 9/2011 | Scheibel et al. | |
| 2012/0021020 | A1 | 1/2012 | Tomich et al. | |
| 2013/0018004 | A1 * | 1/2013 | Sun | A61L 27/22 |
| | | | | 514/21.4 |
| 2013/0023460 | A1 * | 1/2013 | Hauser | A61K 8/042 |
| | | | | 514/1.1 |
| 2014/0093473 | A1 * | 4/2014 | Hauser | C07K 5/101 |
| | | | | 424/78.17 |

FOREIGN PATENT DOCUMENTS

| WO | 2011112856 | | 2/2011 | |
|---|---|---|---|---|
| WO | WO 2011/112856 | * | 9/2011 | ............. A61L 27/52 |

OTHER PUBLICATIONS

Francis, 2010, Albumin and mammalian cell culture: implications for biotechnology applications, Cytotechnology, 62: 1-16.*
Huang et al. 2012, Structural Transformation and physical Properties of a Hydrogel-Forming Peptide Studied by NMR, Transmission Electron Microscopy, and Dynamic Rheometer, Biophysical Journal, 103: 979-988.*
International Search Report and Written Opinion dated Nov. 9, 2015, in PCT/US2015/034409, filed Jun. 5, 2015.
Behrens, Adam M. "Hemostatic Strategies for Traumatic and Surgical Bleeding," Society for Materials, Dec. 12, 2013, Wiley Online Library.
Huang, Hongzhou, "Structural Transformation and Physical Properties of a Hydrogel-Forming Peptide Studied by NMR, Transmission Electron Microscopy, and Dynamic Rheometer," Biophysical Journal, Sep. 2012, pp. 979-988, vol. 103.
Adrianos, Sherry L. "Nephila clavipes Flagelliform Silk-like GGX Motifs Contribute to Extensibility and Spacer Motifs Contribute to Strength in Synthetic Spider Silk Fibers," Biomacromolecules, Jun. 10, 2013, pp. 1751-1760, Bol. 14(6).
Teule, Florence "Combining flagelliform and dragline spider silk motifs to produce tunable sunthetoc biopolymer fibers," Biopolymers, Jun. 2012, vol. 97(6) pp. 418-431.
Sukthankar, Pinakin "Branched Oligopeptides Form Nano-Capsules with Lipid Vesicle Characteristics," Langmuir, Nov. 2013, vol. 29(47) pp. 14648-14654.
Shen, Xinchun "Adhesion and Structure Properties of Protein Nanomaterials Containing Hydrophobic and Charged Amino Acids," Journal Nanoscience and Nanotechnology, 2006, vol. 6(3), pp. 837-844.
Huang, Hongzhou "Design of a shear-thinning recoverable peptide hydrogel from native sequences and application for influenza H1N1 vaccine adjuvant," Soft Matter, Jun. 25, 2011, vol. 7, pp. 8905-8912.

(Continued)

Primary Examiner — Amber D Steele
(74) Attorney, Agent, or Firm — Hovey Williams LLP

(57) ABSTRACT

Peptide hydrogels having a self-assembling, 3-dimensional nanofiber matrix are described. The nanofiber matrix comprises an amphiphilic peptide and optionally albumin. The peptide comprises (consists of) a terminal hydrophobic region, a central turning region, and a terminal hydrophilic region. Methods of making such hydrogels are also described, along with methods of using the hydrogels as scaffolding for tissue engineering, hemostatic agents, as well as 3-dimensional cell cultures, and for drug delivery, encapsulation of active agents (therapeutic cells, molecules, drugs, compounds), cell transplantation, cell storage, virus culture and storage.

19 Claims, 26 Drawing Sheets

Specification includes a Sequence Listing.

(56) References Cited

OTHER PUBLICATIONS

Adrianos, Sheery L. "Nephila clavipes Flagelliform Silk-like GGX Motifs Contribute to Extensiblity and Spacer Motifs Contribute to Strength in Synthetic Spider Silk Fibers," Biomacromolecules, Jun. 10, 2013, vol. 14(6), pp. 1751-1760.

* cited by examiner

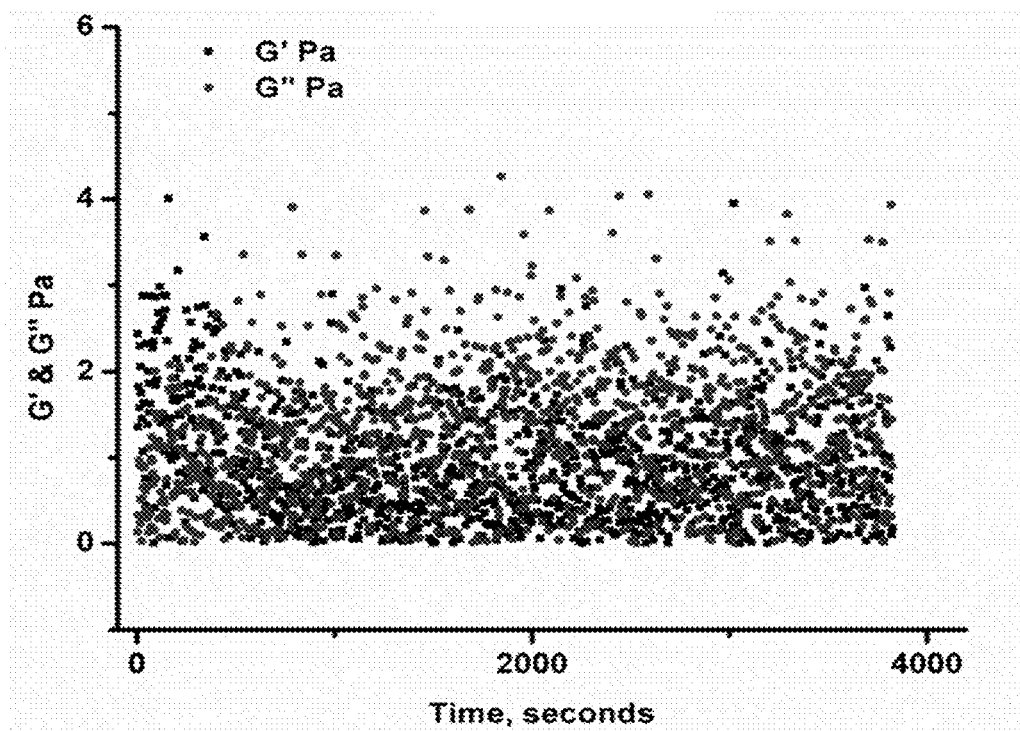
FIG. 7C
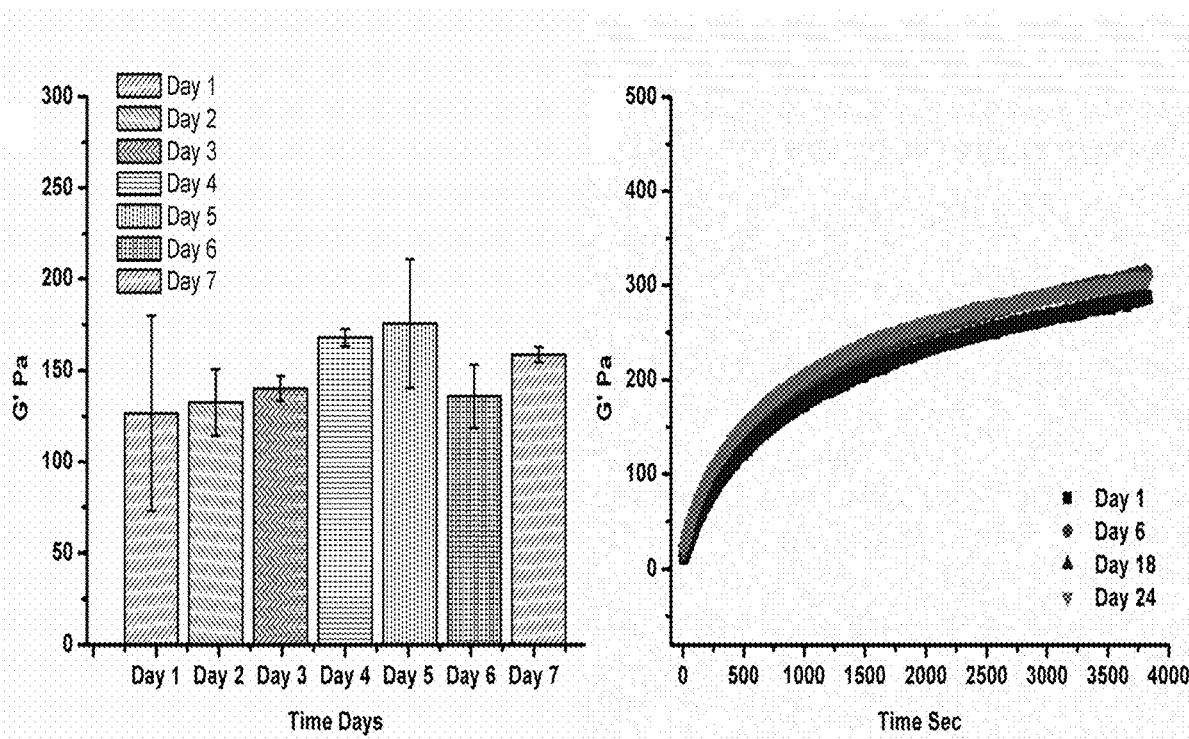
FIG. 8A
FIG. 8B

Gelation Kinetics of Blood and h9e peptide

PEPTIDE HYDROGEL PROPERTIES AND ITS APPLICATIONS

CROSS-REFERENCE TO RELATED APPLICATIONS

The present application is a divisional of U.S. application Ser. No. 15/316,398, filed Dec. 5, 2016, which is the U.S. National Stage of International Patent Application No. PCT/US2015/034409, filed Jun. 5, 2015, which claims the priority benefit of U.S. Provisional Patent Application Ser. No. 62/008,140, filed Jun. 5, 2014, entitled PEPTIDE HYDROGEL PROPERTIES AND ITS APPLICATIONS. All of the foregoing applications are hereby incorporated by reference in their entireties.

SEQUENCE LISTING

The following application contains a sequence listing in computer readable format (CRF), submitted as a text file in ASCII format entitled "SequenceListing," created on Apr. 24, 2015, as 27 KB. The content of the CRF is hereby incorporated by reference.

BACKGROUND OF THE INVENTION

Field of the Invention

The present invention relates to peptide hydrogels, hemostatic agents, and cell cultures therefrom.

Description of Related Art

Using peptide hydrogels as injectable materials for tissue engineering and other biotechnological applications has been an important discovery made over the past few decades. Because of its high water content and polymer network, peptide hydrogels are a promising material for storage and transfer of proteins without significant loss of their biological activity. A sol-gel transformation occurs when peptide molecules self-assemble into a well-defined nanofiber network that traps water molecules. Among U.S. military personnel, hemorrhage is one of the greatest threats to survival. Among American civilians, bleeding is the leading cause of death in operating rooms. Extensive blood loss due to hemorrhage is a worldwide concern. In order to prevent or significantly reduce the number of deaths associated with exsanguination, research has been conducted over the past 40 years. The body naturally addresses the issue of bleeding by the process of hemostasis (coagulation cascade). However, during a traumatic injury, the body may be unable to stop or slow the amount of bleeding caused by the injury.

SUMMARY OF THE INVENTION

The present invention is broadly concerned with peptide hydrogels having a self-assembling, 3-dimensional nanofiber matrix. Exemplary peptide sequences that self-assemble into nano fibers are disclosed in U.S. Pat. No. 8,835,395 B2 incorporated by reference herein in its entirety. While exploring the possible applications of these innovative peptides, we also reported that the peptides can form hydrogel when mixed with serum albumin (PCT Application PCT/US2013/073645). Because of its elastic and high tensile strength properties, the h9e peptide (SEQ ID NO:1) hydrogel has the potential for use in biomaterials for medical uses. Here, we describe the use of these peptides as a hemostatic agent, among other uses.

The nanofiber matrix comprises (consists essentially or even consists of) an amphiphilic peptide and optionally albumin. The amphiphilic peptide comprises (consists essentially or even consists of) a terminal hydrophobic region, a central turning region, and a terminal hydrophilic region. In alternative embodiments, the hydrogel can further comprise an extracellular matrix ligand, lipid, protein, or biopolymer attached to the hydrophilic region of the peptide.

Hemostatic agents prepared from these hydrogels are also disclosed herein, including methods of using the peptides and resulting hydrogels for wound healing and hemostasis. For example, a hemostatic agent useful for promoting blood clotting and/or reducing hemorrhaging is disclosed herein. The hemostatic agent comprising a peptide, wherein the peptide is amphiphilic and comprises a terminal hydrophobic region, a central turning region, and a terminal hydrophilic region. Methods of treating a wound site or reducing hemorrhaging in a subject having a wound are also described herein. The method comprises delivering a hemostatic agent, as described herein, to the site of the wound.

Methods of forming a peptide-albumin hydrogel are also described herein. The methods comprise providing a peptide solution comprising a peptide dispersed, dissolved, or suspended in a solvent system, and mixing a source of albumin with the peptide solution at room temperature to form a peptide-albumin solution. The peptide is amphiphilic and comprises a terminal hydrophobic region, a central turning region, and a terminal hydrophilic region. The peptide and albumin self-assemble into the peptide-albumin hydrogel without adjusting the pH, temperature, salt, or ion composition of the peptide-albumin solution.

Methods of using the peptide-albumin hydrogels are also described herein, including methods of delivering an active agent to a patient. The methods comprise administering to the patient a peptide-albumin hydrogel according to any of the embodiments described herein, wherein the active agent is encapsulated in the hydrogel matrix.

Methods of storing and expanding cells, such as stem cells and red blood cells, are also described. The methods generally comprise mixing cells with a self-assembling amphiphilic peptide and a hydrogelation agent, to yield a 3-dimensional cell culture comprising the cells embedded in a hydrogel matrix. The peptide consists of a terminal hydrophobic region, a central turning region, and a terminal hydrophilic region. The hydrogel matrix comprises a 3-dimensional nanofiber matrix comprising the peptide. The cells are maintained and can be expanded in the hydrogel matrix under cell culture conditions.

BRIEF DESCRIPTION OF THE DRAWINGS

Figure (FIG. 1 shows TEM images of peptide-albumin mixture: A. h9e/BSA mixture, B. h9e/HSA mixture;

FIG. 7C shows a graph illustrating G' and G" of 2 mM h9e-2i hydrogel after 20 fold dilution;

FIG. 8A shows a graph of G' of h9e-2i hydrogel from Day 1 to Day 7;

FIG. 8B shows a graph illustrating the hydrogel formation of h9e-2i mixture after the h9e solution was stored at 4° C. refrigerator for 1, 6, 18 and 24 days;

DETAILED DESCRIPTION

Figure 1:
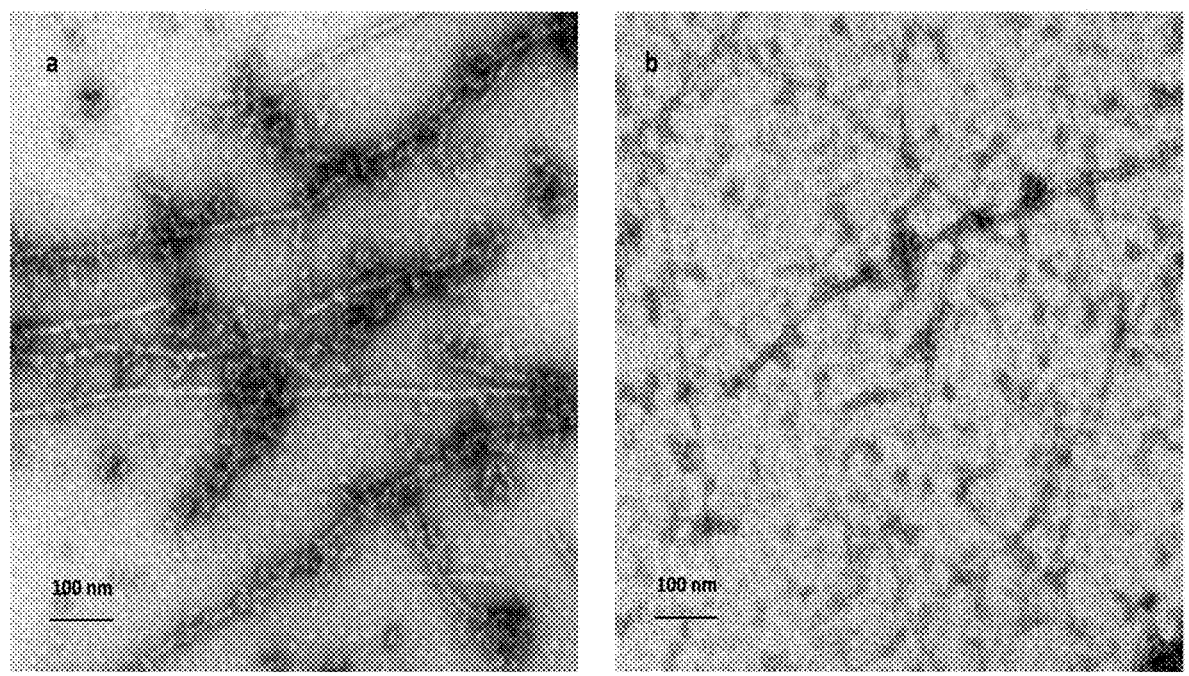

The present invention is concerned with self-assembled hydrogels and methods of making and using the same. The hydrogel matrix network comprises a peptide and optionally albumin which make up the 3-dimensional nanofibrous network of the hydrogel structure. The peptide hydrogels are characterized by a "reversible" hydrogel matrix, which means that the 3-dimensional nanofibrous matrix is shear thinning (i.e., the viscosity decreases with an increase in the rate of shear stress applied to the gel), but recovers quickly after gel destruction, as discussed in more detail below. The hydrogels are useful in various applications, including as scaffolds for tissue engineering, 3-dimensional (3-D) cell cultures, drug delivery and encapsulation of therapeutic agents (cells, molecules, drugs, compounds), injectables (including those that gel in situ, such as hemostatic compositions), hemostatic agents, wound dressings, pharmaceutical carriers or vehicles, cell transplantation, cell storage, virus culture, virus storage, and the like.

The peptide hydrogels have a uniform internetwork morphology with a porous structure and open cells. The average cell size of the hydrogel matrix will be from about 10 µm to about 80 µm, preferably from about 20 µm to about 60 µm, and more preferably from about 30 µm to about 50 µm, as observed under a scanning electron microscope. The average pore size will range from about 50 to about 200 nm. The hydrogel peptides are in the form of peptide nanofibers having an average diameter of from about 3 nm to about 30 nm, preferably from about 5 nm to about 20 nm, and more preferably from about 8 nm to about 15 nm, as measured under a transmission electron microscope. The peptide nanofibers have an average length of from about 0.3 µm to about 5 µm, preferably from about 0.8 µm to about 3 µm, and more preferably from about 1 µm to about 2 µm.

Hydrogel formation can be triggered using various approaches, including selected proteins and metal ions. Calcium ions and albumin can be used together to initiate nanofiber formation and further hydrogelation.

In one or more embodiments, the hydrogel is a peptide-albumin hydrogel. The peptide-albumin hydrogels have a storage modulus (associated with gel strength) of at least about 50 Pa, preferably at least about 100 Pa, and more preferably from about 100 Pa to about 10,000 Pa. It will be appreciated that by varying the peptide and albumin concentrations, the strength of the particular hydrogel can be tuned to the desired application for the gel. For example, for an injectable hydrogel, the hydrogel matrix will have a storage modulus of from about 50 Pa to about 3,000 Pa and preferably from about 70 Pa to about 1,000 Pa. In some embodiments, such as scaffolding, very strong hydrogels can be formed, having a storage modulus of at least about 300 Pa, preferably from about 500 Pa to about 10,000 Pa, and even more preferably from about 1,000 Pa to about 5,000 Pa. These gel strengths are based upon a neutral pH (about 7) and a temperature of about room temperature (aka "ambient temperature" or about 20-25° C.).

As noted above, the hydrogel matrix is reversible. This means that after gel destruction by subjecting the gel to a sufficient mechanical force (e.g., shear thinning), the hydrogels have a % recovery of at least about 60%, preferably at least about 80%, more preferably at least about 90%, and even more preferably about 100% in less than about 10 minutes, preferably in less than about 5 minutes, and more preferably in less than about 2 minutes (after removing the shear stress from the destroyed gel). As used herein, the "% recovery" of the hydrogel is the percentage of the original storage modulus (i.e., before gel destruction) achieved by the gel after destruction and re-hydrogelation. In other words, shear thinning only temporarily destroys the gel structure or architecture. Shear thinning can be carried out using various mechanical forces that impose a shear strain or shear stress on the hydrogel, such as pipetting, centrifugation, vibration, injection, spraying, filtration, and the like. As noted above, reassembly of the gel or hydrogelation reoccurs quickly after shear thinning and destruction of the gel structure (i.e., after removal of or stopping the application of mechanical force to the destroyed gel). This recovery property also persists even after destroying the gel structure multiple times. Advantageously, the destroyed matrix after shear thinning can also be diluted with solvent to a substantially liquid solution (i.e., G'<0.2 Pa) to stop the recovery process. In other words, when diluted to a peptide concentration of less than about 0.1% by weight, the peptide-albumin solution remains in a low-viscosity liquefied form and does not rapidly reassemble. This technique is useful for isolating cells or other components cultured in the hydrogel, such as by separating (e.g., by centrifugation) the liquefied peptide-albumin solution from the cells. This process can be enhanced by maintaining the liquefied and diluted peptide-albumin solution at a low temperature (about 4° C.) during separation.

The inventive gels are water soluble and temperature stable up to about 90° C. As used herein, "water soluble" means the gels can be diluted with water after formation, and "temperature stable" means that the hydrogel is not denatured at temperatures ranging from about 1° C. to about 90° C. Advantageously, unlike other types of gels, the storage modulus of the inventive peptide-albumin hydrogels increases as temperature is increased.

The hydrogels are prepared by combining the peptides with a source of albumin or other hydrogelation agent (e.g., proteins, metal ions, etc. that can trigger gelation). As used herein, a "source of albumin" refers to one or more types of (purified) albumin that can be directly combined with the peptides, a composition containing one or more types of albumin, as well as albumin derivatives.

In one or more embodiments, the method involves forming or providing a solution of peptides according to the invention. The peptide solution comprises (consists essentially or even consists of) the peptides suspended, dispersed, or dissolved in a solvent system at levels of at least about 0.001%, preferably from about 0.001% to about 5% by weight, more preferably from about 0.3% to about 3.5% by weight, and even more preferably from about 0.5% to about 2% by weight, based upon the total weight of the solution taken as 100% by weight. It has been found that when the hydrogels are desired for use as a flowable matrix for 3-D cell culture, lower starting concentrations of peptides are desired. Dried (e.g., freeze-dried) peptides are suitable for use in the invention and can be mixed with the solvent system to create the peptide solution. The peptide solution has a pH of from about 6 to about 8, preferably from about 6.5 to about 7.5, more preferably from about 7 to about 7.5, and even more preferably about 7. Suitable solvent systems include aqueous alkaline solutions, such as sodium bicarbonate, sodium hydroxide, potassium hydroxide, and mixtures thereof in water.

The peptide solution is combined with a source of albumin, such as a composition comprising (consisting essentially of or even consisting of) albumin. Suitable types of albumin for use in the invention include albumin isolated, extracted, and/or purified from plant or animal sources, as well as synthesized albumin, such as recombinant/transgenic albumin (e.g., human albumin expressed in a plant system), and derivatives thereof (e.g., modified albumins, such as biotin-labeled, acetylated, glycated, nitrated, etc.). The albumin itself can be directly added to the peptide solutions, or it can be provided as part of a composition that contains albumin. For example, whole blood can be used as the source of albumin. In one or more embodiments, the peptide solution can be combined with whole blood to initiate hydrogelation. Examples of other such compositions include serum, serum-supplemented cell media (e.g., Minimum Essential Medium (MEM), Dulbecco's modified Eagle's medium (DMEM), Roswell Park Memorial Institute medium (RPMI), and Leibovitz medium), CMRL 1066 (Sigma), plasma, and the like. In one or more embodiments, the source of albumin can be mixed with a solvent system, such as water, to form a solution comprising albumin (or a source of albumin). This solution is then mixed with the peptide solution, preferably at about room temperature. The resulting peptide-albumin solution has a substantially neutral pH of from about 6 to about 8, preferably from about 6.5 to about 7.5, more preferably from about 7 to about 7.5, and even more preferably about 7.

The level of albumin used is at least about 0.001% by weight, preferably from about 0.5% by weight to about 20% by weight, and more preferably from about 1% by weight to about 10% by weight, based upon the total weight of the peptide-albumin solution taken as 100% by weight. The level of peptide used will vary depending upon the desired function of the hydrogel. In one or more embodiments, the peptide concentration is at least about 0.001% by weight, preferably from about 0.1% by weight to about 10% by weight, more preferably from about 0.15% by weight to about 5% by weight, and even more preferably from about 0.2% by weight to about 1% by weight, based upon the total weight of the peptide-albumin solution taken as 100% by weight. However, for wound healing or hemostatic applications, higher peptide concentrations above 1% by weight may be more preferred (e.g., from about 1 to about 5% by weight, preferably from about 2 to about 5% by weight, and more preferably from about 3 to about 5% by weight) to facilitate blood clotting and stop bleeding. The gel typically comprises at least about 0.001% by weight peptide, preferably from about 0.1% to about 3% by weight of the peptide, preferably from about 0.25% to about 1.5% by weight of the peptide, and more preferably from about 0.5% to about 1% by weight of the peptide, based on the total weight of the gel taken as 100% by weight. In either the solution or gel, the weight ratio of peptide to albumin is preferably from about 100:1 to about 1:100, more preferably from about 10:1 to about 1:10, and even more preferably from about 2:1 to about 1:2.

It will be appreciated that the desired properties of the hydrogel can be varied by modifying the relative concentration of peptide and albumin in the peptide-albumin solution. For example, higher albumin concentrations can be used to induce very rapid gel formation, while higher peptide concentrations can be used to form higher strength gels. Regardless, the hydrogel is considered formed once G' (storage modulus) is greater than G" (storage loss). In other words, the composition is considered a hydrogel when it reaches self-supporting strength and is not susceptible to deformation merely due to its own internal forces. The hydrogel typically forms in less than about 120 minutes after combining the peptide and the albumin, preferably less than about 60 minutes, and more preferably from about 15 to about 30 minutes. Again, it will be understood that these parameters can be varied by modifying the albumin and peptide concentrations.

Advantageously, hydrogelation is induced upon mixing the peptide solution with the hydrogelation agent (e.g., source of albumin), without any further modifications to the system. That is, the preparation method does not require and is preferably essentially free of modifications or adjustments to the pH of the system (e.g., by adding a buffer), the chemical composition, or the temperature of the system. In other words, unlike other hydrogelation techniques, the inventive method is preferably essentially free of chemical or environmental modifications to the peptide-albumin solution for hydrogel formation. As used here, "essentially free" means that the omitted ingredients or steps are not intentionally added or carried out to achieve hydrogelation, although it is appreciated that incidental impurities or ancillary steps may be included that do not otherwise modify the hydrogel and are encompassed by the invention. In some embodiments, the resulting hydrogels are also preferably essentially free of one or more of synthetic polymers, polysaccharides, lipids, undesirable buffers (e.g., citrate/lactate buffer, etc.), and the like.

As noted above, the hydrogels have various uses, including as scaffolding for tissue engineering, drug delivery, and the like. Advantageously, active agents, including therapeutics, such as small molecule drugs and/or biologics (e.g., enzymes and other proteins and peptides, and DNA and RNA fragments), can be encapsulated in the hydrogel simply by adding the active agent to the peptide-albumin solution, such that encapsulation takes place in situ during hydrogelation. Due to the neutral pH (physiological pH) of the peptide-albumin solution and the fact that chemical and/or environmental modifications are not carried out on the system to induce hydrogelation, this encapsulation technique is particularly well-suited to encapsulating biologic therapeutic agents requiring physiological conditions. The hydrogel can be used in pharmaceutically acceptable compositions as a delivery vehicle for administration of the active agent to a subject (e.g., orally, intravenously, subcutaneously, intramuscularly, nasally, etc.).

The peptides and resulting hydrogels can also be used as hemostatic compositions to stop bleeding and promote blood clotting and gelation at a wound site (e.g., internal or external laceration, abrasion, incision, puncture, etc.) of a patient. Advantageously, hydrogel formation can be carried out in situ by administering a solution of the inventive peptides, or the peptide-albumin solution to the patient. Alternatively, the peptide solution alone could be administered to the patient, wherein native (in vivo) albumin in the patient's blood and/or blood stream initiates hydrogel formation in situ at the wound site. In other words, the peptide solution can be administered to the patient as a hemostatic agent without added albumin. In one or more embodiments, the invention is concerned with a method of treating a wound site or reducing hemorrhaging in vivo by administering to a patient a peptide solution (with or without albumin) according to the invention, or applying the peptide solution to the wound site (with or without added albumin). The peptide solution would typically be administered via an injection at or near the wound site, or other delivery of the peptide solution to the wound site (e.g., such as using a syringe to dispense the peptide solution into the wound site).

The peptide solution can also be mixed with the patient's blood to promote pre-gelation of the hydrogel, followed by delivery to the wound site to promote further clotting at the wound site. The peptide solution can also be delivered to the wound site in dried form instead of being in solution. The peptide can alternatively be reconstituted with a solvent system before being delivered to the wound site. The hydrogels can also be used as 3-dimensional cell cultures. For example, the cells to be cultured can be mixed with the peptide-albumin solution, and in particular, can be added to the system as part of serum-supplemented cell media. During hydrogelation, the cells become encapsulated within the hydrogel matrix. The hydrogel can then be applied (plated, seeded, etc.) to a cell culture plate or microwell for cell culturing. In one or more embodiments, the hydrogel can be covered with additional cell media to prevent drying out, and the hydrogel containing the cells can be incubated under cell culture conditions (i.e., the appropriate conditions for cell maintenance and/or growth, depending on the cell type). Because of the reversible nature of the hydrogel, the cultured cells can be later isolated from the hydrogel. For example, the hydrogel can be subjected to a mechanical force to disrupt the hydrogel matrix, in combination with diluting the hydrogel (e.g., with additional cell media or other solvent). The resulting liquefied peptide and cell mixture can then be separated to isolate the cultured cells. This technique is suitable for use with various types of cells including stem cells, cancer cells, primary cells, normal cells, neuron cells, and the like.

Linear, self-assembling peptides are used in forming the hydrogels. Suitable peptides are described in WO 2011/112856, incorporated by reference herein in its entirety to the extent not inconsistent with the present disclosure. The peptides comprise (consist essentially or even consist of) three segments or regions: a terminal hydrophobic region, a central turning region, and a terminal hydrophilic region. The turning region is positioned between, and preferably directly connected to, the hydrophobic and hydrophilic regions. Thus, the peptides are amphiphilic, with one end segment of the peptide being relatively water loving (aka "hydrophilic"), the other end segment of the peptide being relatively water fearing (aka "hydrophobic"), and the central turning region providing the flexibility for turning and folding. A region is considered "hydrophilic" in the context of the present disclosure, if the region has a greater water affinity than the hydrophobic region of the corresponding peptide. Likewise, a region is considered "hydrophobic" herein, if the region has a greater aversion to water than the respective hydrophilic segment of the corresponding peptide. Accordingly, it will be appreciated that a hydrophobic region may still include one or more hydrophilic amino acid residues, as long as the overall nature of the region is nonetheless more hydrophobic than the corresponding hydrophilic region of the peptide. Similarly, a hydrophilic region may include one or more hydrophobic amino acid residues, as long as the overall nature of the region is nonetheless more hydrophilic than the corresponding hydrophobic region of the peptide. As used herein, it will be appreciated that when referring to amino acids that are present as part of a peptide, the amino acids are actually amino acid residues, regardless of whether "residues" is specifically stated.

The hydrophobic region is preferably elastic and capable of binding the Group I and Group II metals (and particularly calcium). Preferred hydrophobic regions comprise (consist essentially or even consist of) from about 2 to about 15 amino acid residues, preferably from about 4 to about 9 amino acid residues, and more preferably about 5 amino acid residues. The amino acid residues are preferably selected from the group consisting of F, L, I, V, A, D, P, G, and H, where at least one amino acid residue is I. More preferably, the hydrophobic region contains at least F and I or at least V and I. In one or more embodiment, the hydrophobic region is selected from the group consisting of FLIVI (SEQ ID NO:2), GLIVI (SEQ ID NO:5), PLIVI (SEQ ID NO:6), DLIVI (SEQ ID NO:7), VLIVI (SEQ ID NO:8), ILIVI (SEQ ID NO:9), LLIVI (SEQ ID NO:10), ALIVI (SEQ ID NO:11), FGIVI (SEQ ID NO:12), FPIVI (SEQ ID NO:13), FDIVI (SEQ ID NO:14), FVIVI (SEQ ID NO:15), FIIVI (SEQ ID NO:16), FAIVI (SEQ ID NO:17), FLGVI (SEQ ID NO:18), FLPVI (SEQ ID NO:19), FLDVI (SEQ ID NO:20), FLVIV (SEQ ID NO:21), FLAVI (SEQ ID NO:22), FLIGI (SEQ ID NO:23), FLIPI (SEQ ID NO:24), FLIDI (SEQ ID NO:25), FLIII (SEQ ID NO:26), FLILI (SEQ ID NO:27), FLIAI (SEQ ID NO:28), FLIVG (SEQ ID NO:29), FLIVP (SEQ ID NO:30), FLIVD (SEQ ID NO:31), FLIVV (SEQ ID NO:32), FLIVL (SEQ ID NO:33), and FLIVA (SEQ ID NO:34). In one or more embodiment, the hydrophobic region is FLIVI (SEQ ID NO:2).

Alternative hydrophobic regions comprise (consist essentially or even consist of) $X^{22}X^{23}X^{24}VI$ (SEQ ID NO:55), where $X^{22}$ can be selected from A, V, H, where $X^{23}$, can be selected from A, V, H, and where $X^{24}$ can be selected from A, V, H, In one or more embodiments, V, and I can be switched with any amino acid in the hydrophobic segment.

Preferred hydrophilic regions comprise (consist essentially or even consist of) from about 5 to about 20 amino acid residues, preferably from about 5 to about 10 amino acid residues, and more preferably about 10 amino acid residues. More preferably, the hydrophilic regions comprise amino acid residues selected from the group consisting of G, P, D, V, I, L, and A, where at least three of the residues are G, P, and D. In one or more embodiments, the hydrophilic region is selected from the group consisting of $[GPXXD]_n$ (SEQ ID NO:35), $[GXXPD]_n$ (SEQ ID NO:36), $[GXPXD]_n$ (SEQ ID NO:37), and combinations thereof, where n=1-6, and each X is individually selected from the group consisting of G, A, D, R, Q, E, S, T, K, Y, H, and P. In one embodiment, the hydrophilic region comprises, and preferably consists of, in any order, amino acid residues of $GPGX^1DGPGX^1D$ (SEQ ID NO:38), where $X^1$ is selected from the group consisting of G and A. In another embodiment, the hydrophilic region comprises, and preferably consists of, in order, amino acid residues of $GPGX^1DGPGX^1D$ (SEQ ID NO:38), where $X^1$ is selected from the group consisting of G and A. In a further embodiment, the hydrophilic region comprises, and preferably consists of, in order or in any order, amino acid residues of $GPGX^2DGX^3X^2X^2D$ (SEQ ID NO:39), where each $X^2$ is individually selected from the group consisting of A, G, V, I, and L, and $X^3$ is selected from the group consisting of P, A, G, V, I, and L. In yet another embodiment, the hydrophilic region comprises amino acid residues of $GPGX^2D$ (SEQ ID NO:40), where $X^2$ is defined above. Furthermore, the hydrophilic region could be selected from the group consisting of amino acid residues of $[GPGX^2DGX^3X^2X^2D]_n$ (SEQ ID NO:39) and $[GPGX^2D]_n$ (SEQ ID NO:40), where n is from 1 to 10, and more preferably from 1 to 5, and $X^2$, and $X^3$ are defined as above.

Alternative hydrophilic regions comprise (consist essentially or even consist of): Group 1. Substitution with W at any location in $GPGX^7DGX^8X^7X^7D$ (SEQ ID NO:56)

replacing the $X^7$ and $X^8$, G or P. W could also be inserted at either end of the segment (SEQ ID NO:57 or (SEQ ID NO:58). The use of W can be used to provide florescence tracking properties, which would be useful for drug or cell or bioactive compounds delivery applications. W can also be used to promote hydrophobic interaction with hydrophobic drugs or molecules and compounds.

Group 2. GPGX$^7$DGX$^8$X$^7$X$^7$D (SEQ ID NO:56), in any order, where each $X^7$ can be selected from K, E, R, Y or S group or K, E, R, Y and S containing segments, and $X^8$ is selected from the group consisting of P, A, G, V, I, and L. K and E can be used to create peptides with other metal ion binding abilities (beyond calcium), such as Na, Mg, Zn. S can be used to promote hydrogen bonding and interaction with selected molecules. K can also be used to promote adhesion.

Group 3. GPGX$^9$DGX$^{10}$X$^9$X$^9$D (SEQ ID NO:59), in any order, where each $X^9$ is individually selected from the group consisting of A, G, V, I, H, and L, and $X^{10}$ is selected from the group consisting of P, A, G, V, I, H and L. In one or more embodiments, the order of residues 1 and 2 (GP) can be switched to PG (SEQ ID NO:60). In one or more embodiments, the order of residues 2 and 3 (PG) can be switched to GP (SEQ ID NO:61). In one or more embodiments, the order of residues 5 and 6 (DG) can be switched to GD (SEQ ID NO:62).

Group 4. GPGX$^{11}$D (SEQ ID NO:63), where $X^{11}$ is selected from the group consisting of A, G, V, I, L, K, E, S, R, Y, H and W.

Group 5. GPGX$^{12}$DGX$^{13}$X$^{12}$X$^{12}$D (SEQ ID NO:64), where each $X^{12}$ can be selected from K, E, R, Y or S group or K, E, R, Y and S containing segments, and D can be replaced by K, E, W, or S individually, and $X^{13}$ is selected from the group consisting of P, A, G, V, I, H and L. In one or more embodiments, D can be switched with any amino acid in the hydrophilic segment.

Group 6. GPGGDGPGGDX$^{14}$X$^{15}$X$^{16}$X$^{17}$ (SEQ ID NO:65), where $X^{14}$ can be selected from G, S, Y, K, E, D, H, V, and A, where $X^{15}$, can be selected from R, Y, S, Y, E, and where $X^{16}$ can be selected from A, G, V, where $X^{17}$ can be selected from D, R, S, H, V, and A, individually. In one or more embodiments, D can be switched with any amino acid in the hydrophilic segment.

Group 7. GPGGDGPG X$^{18}$X$^{19}$X$^{20}$X$^{21}$ (SEQ ID NO:66), where $X^{18}$ can be selected from G, S, Y, K, E, D, H, V, and A, where $X^{19}$, can be selected from R, Y, S, Y, E, and where $X^{20}$ can be selected from A, G, V, where $X^{21}$ can be selected from D, R, S, H, V, and A, individually. In one or more embodiments, D can be switched with any amino acid in the hydrophilic segment.

In one or more embodiments, the most preferred hydrophilic region comprises GPGGDGPGGD (SEQ ID NO:4) (in any order, but preferably in this order), or a fragment or variant having at least about 60% homology to this sequence, and retaining the functional characteristics thereof. More preferably, the % homology to this sequence is at least about 80% and even more preferably at least about 90%, and retaining the functional characteristics thereof.

For a functional hydrogel-forming peptide in this design, the hydrophobic region is not directly connected to the hydrophilic region, but includes a turning region in-between. The turning region provides structural flexibility which allows the potentially charged side-chains of the hydrophilic residues to come in proximity and help the segregation of hydrophobic and non-hydrophobic side-chains. Thus, it will be appreciated that the central region is considered a "turning" region in the context of the present disclosure because it is comprised of amino acids with small side chains allowing for flexibility and "turning" in that region of the peptide.

Preferred turning regions comprise from about 1 to about 12 amino acid residues, preferably from about 4 to about 8 amino acid residues, and preferably 4 amino acid residues. The turning region of the inventive peptides preferably comprises amino acids residues selected from the group consisting of G, L, I, V, A, S, and T, where the turning region preferably includes at least G, and more preferably at least G and S. In one or more embodiments, the turning region is selected from the group consisting of G, GG, GGG, GGGG (SEQ ID NO:41), GSX$^4$X$^4$ (SEQ ID NO:42), X$^4$GSX$^4$ (SEQ ID NO:43), X$^4$X$^4$GS (SEQ ID NO:44), SGX$^4$X$^4$ (SEQ ID NO:45), X$^4$SGX$^4$ (SEQ ID NO:46), X$^4$X$^4$SG (SEQ ID NO:47), GX$^4$SX$^4$ (SEQ ID NO:48), X$^4$GX$^4$S (SEQ ID NO:49), SX$^4$GX$^4$ (SEQ ID NO:50), X$^4$SX$^4$G (SEQ ID NO:51), GX$^4$X$^4$S (SEQ ID NO:52), and SX$^4$X$^4$G (SEQ ID NO:54), where each $X^4$ is individually selected from the group consisting of G, I, V, A, L, S (and where S could be replaced by T in all sequences listed). One preferred turning region comprises, and preferably consists of, amino acid residues of X$^5$SX$^6$X$^6$ (SEQ ID NO:54), in any order (even more preferably in this order), where $X^5$ is selected from the group consisting of G, I, and V, with G being particularly preferred, and each $X^6$ is individually selected from the group consisting of G, I, V, A, and L, with I being particularly preferred. Preferably, at least one of $X^5$ or $X^6$ is G, with it being particularly preferred that at least $X^5$ is G. In one embodiment, S of X$^5$SX$^6$X$^6$ (SEQ ID NO:54) could be replaced with T. In one or more embodiment, the turning region is GSII (SEQ ID NO:3).

The peptides are preferably short peptides. That is, it is preferred that the peptides have less than about 30 amino acid residues, more preferably less than about 20 amino acid residues, and even more preferably 19 amino acid residues. The most preferred peptide according to the invention comprises (consists essentially or even consist of) the amino acid sequence FLIVIGSIIGPGGDGPGGD (SEQ ID NO:1), or a fragment or variant thereof having at least about 60% homology to this sequence, more preferably at least about 80% homology to this sequence, and even more preferably at least about 90% homology to this sequence, and retaining the functional characteristics thereof.

Finally, the peptides will have a weight average molecular weight of from about 600 Da to about 4,500 Da, more preferably from about 1,000 Da to about 3,000 Da, and more preferably about 1,740 Da.

The peptides can be prepared by microwave synthesizer, microbiosynthesis, fermentation, or genetic engineering technologies. A preferred method involves combining two native sequences from an elastic segment of spider silk and a trans-membrane segment of human muscle L-type calcium channel. More specifically, the most preferred hydrophilic region, GPGGDGPGGD (SEQ ID NO:4), is preferably designed from a β-spiral motif of spider flagelliform silk protein, while the most preferred hydrophobic region FLIVI (SEQ ID NO:2) and turning region GSII (SEQ ID NO:3), are derived from the third trans-membrane segment of subunit IV in the dihydropyridine sensitive human muscle L-type calcium channel. After precipitation and washing, the peptides can be freeze-dried (lyophilized) for storage until use.

It will be appreciated that hydrogels can be developed using a mixture of two or more different peptide sequences, including mixtures of any two or more of the peptides disclosed herein. The synthesized peptides can also be modified by attaching a functional amino acid, peptide segments, or molecules to the either end, or in between. The synthesized peptides can also be modified by attaching a functional amino acid, peptide segments, or molecules to the side as branching peptides.

The hydrogels can also include the peptides with built-in extracellular matrix (ECM) ligands. For example the peptide can be synthesized or blended with ECM ligands and functional proteins, lipids, and biopolymers, such as GRGD (SEQ ID NO:70), RGDS (SEQ ID NO:71), RGD, HAV, RGDSY (SEQ ID NO:72), KYRGDS (SEQ ID NO:73), and laminin proteins (i.e., YIGSR (SEQ ID NO:74) or α1 epitope IKVAV (SEQ ID NO:75)). The mechanical and surface properties of the hydrogel system can be easily modulated in a large range by controlling the variation of the peptide backbone structure in addition to hydrogel formulation. A desirable system can be rationally designed to adapt specific growth factors, functional ECM ligands, and chemical compounds to promote cell adhesion and differentiation of a specific cell type, particularly stem cells. ECM ligands such as integrin or cadherin or laminin can be built-in the backbone of the peptide structure or blended with the nanofiber during hydrogel formation.

The peptide hydrogels are injectable into biological system (e.g. muscle, fat pad, and under the skin) or can be applied to wounds without causing any inflammatory effects. This property makes the hydrogel useful in regenerative medicine, such as drug delivery, cell therapy, gene therapy etc.

The peptide hydrogel allows drugs, small molecules, compounds, growth factors, and nutrients to diffuse through the hydrogel. This property makes the hydrogel useful for many applications, such as in vitro 3-D assay for drug toxicity and efficacy screening, disease diagnosis and treatment development, cell performance testing.

The peptide hydrogel allows oxygen transfer (OT) through the hydrogel. This property is important property for in vitro tissue and organ regeneration process. The OT rate of the h9e hydrogel at 0.5% peptide concentration was about 3,984 cc/m$^2$ per day. The OT rate can be changed by altering the hydrogel formulation and modification.

The peptide hydrogel can also be used as a cell culture. More specifically, the peptide hydrogel can be used store and grow stem cells without differentiation for more than 20 passages, preferably at least about 25, and even more preferably at least about 30 passages. Expanding undifferentiated stem cells, such as pluripotent stem cells (PSCs) embryonic stem cells (rESCs), mesenchymal stem cell (MSC), in a synthetic 3D microenvironment in vitro has been challenging. Regular h9e hydrogel was used to allow stem cells to remain undifferentiated after several passages. This property is has potential applications for regenerative medicine, cell therapy, and tissue engineering, as well as drug toxicity testing using stem cells as sensors in vitro.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example I

Peptide-Albumin Hydrogel Formation and Properties

Introduction

Because of its distinct three-dimensional network, peptide hydrogel not only provides an in vitro environment that mimics the extracellular matrix conditions for 3D cell culture but also acts as an auxiliary carrier for targeted drug or gene delivery and biomolecular controlled release. With the rapid development of peptide hydrogels for biomedical applications, the mild method to trigger the peptide solution into hydrogel has attracted more attentions to apply these materials. In our recent study, we found that the h9e peptides could spontaneously organize into an injectable hydrogel material under the trigger of Bovine Serum Albumin (BSA) or Human Serum Albumin (HSA) without adding any other metal ions or adjusting environmental pH or temperature. This is the first time a rationally designed peptide has been found to self-assemble into hydrogel through binding with albumin molecules. The objective of this study is to understand how albumin triggers h9e peptide self-assembly into hydrogel. The storage modulus of hydrogel as well as the hydrogel forming rate are affected by peptide and albumin concentration. Because albumin is the most abundant protein in human serum and is considered one of the most important proteins for molecular transportation, pH balance, and maintaining osmotic pressure, hydrogel formed through albumin binding has great potential for a wide range of applications.

Methods and Materials

1. Peptide Synthesis and Hydrogel Preparation

Peptides were synthesized on a CEM Liberty microwave peptide synthesizer (CEM Corporation, Matthews, N.C.) based on the automated base-labile 9-fluorenylmethoxycarbonyl (Fmoc) strategy with Fmoc-protected amino acids (EMD Biosciences, San Diego, Calif.). Peptides were cleaved with 95% trifluoroacetic acid (Sigma-Aldrich, Milwaukee, Wis.), 2.5% triisopropylsilane (Sigma), and 2.5% deionized water. The crude peptides were washed three times with anhydrous ether (Fisher Biotech, Fair Lawn, N.J.). After that, peptides were dissolved in acetonitrile and distilled (DI) water (50/50 v/v). The peptide solution was frozen in a −80° C. refrigerator overnight and then was freeze-dried for 48 hours by using the Labconco freeze dry system (Labconco, Kansas City, Mo.). The pH value of the peptide in water solution was 3.6. Molecular weight of the synthesized peptide was confirmed by matrix-assisted laser desorption/ionization time-of-flight mass spectroscopy on an Ultraflex II instrument (Bruker Daltronics, Billerica, Mass.). The peptide purity was confirmed by a Beckman System Gold high performance liquid chromatography (HPLC, Beckman Coulter, Inc., Fullerton, Calif.) on a phenomenex synergi 4μ Hydro-RP column (Phenomenex, Inc., Torance, Calif.) with the following gradient: 10-90% B in 20 min (A: 99.9% H2O, 0.1% TFA; B: 90% acetonitrile, 9.9% H2O, 0.1% TFA).

For albumin triggered hydrogel formation, 10 mM (1.74 wt %) peptide was first dissolved in 100 mM NaHCO$_3$ solution. BSA and HSA were dissolved in water with 5 wt % concentration. The peptide solution and albumin solution were then mixed at different ratios for final mixtures of 1, 2, 3 mM h9e peptide with albumin from 0.1 to 5 wt %.

2. Transmission Electron Microscopy (TEM)

Peptide solutions were prepared by a negative strain method in which 20 μl peptide solution was placed on Formvar/carbon-coated 200-mesh copper grids (Electron Microscopy Sciences, Fort Washington, Pa.) for 1 min. The extra solution was removed and the TEM grids were floated on the top surface of 2% (w/v) uranyl acetate (Ladd Research Industries, Inc., Burlington, Vt.) for 60 s at ambient conditions. The TEM grids were removed and dried before imaging. The samples were observed with a CM100 TEM (FEI Company, Hillsboro, Oreg.) at 100 kv.

3. Rheology

The storage (G') and loss (G") moduli of h9e hydrogels with different peptide/albumin ratios were measured on a rheometer system C-VOR 150 (Malvern instruments, Malvern, Worcestershire WR141XZ, United Kingdom) with a 20 mm diameter parallel plate test system. All rheological tests were carried out at 37° C. To determine the hydrogel forming rate, the peptide and albumin mixture was placed on the measuring system immediately after preparation and tested by a single frequency (1 Hz) method with steady shear strain (1%) for 1 hour 4. Hydrogel Properties We found serum in the cell medium was an important factor to help hydrogel formation: without any additional chemical or environmental adjustment, h9e peptide solution could be directly added into Minimum Essential Medium (MEM) with 10% serum and transformed into a self-supporting hydrogel matrix within 1 min. However, using MEM without serum did not stimulate this solution to hydrogel transitions effectively. This phenomenon was further exploited in other cell culture medium like Dulbecco's modified Eagle's medium (DMEM), Roswell Park Memorial Institute medium (RPMI), and Leibovitz medium (L-15). Because serum is an extremely complex composition, determining the major factors that triggered hydrogel formation was difficult. After screening the abundant serum compounds, we concentrated on one of the most abundant proteins in serum, albumin, which contains charged groups and several surface binding domains. Interestingly, the hydrogel formation of h9e peptide in a serum-free N2B27 supplemented 2i medium with 1 wt % albumin confirmed our hypothesis.

Figure 2A:
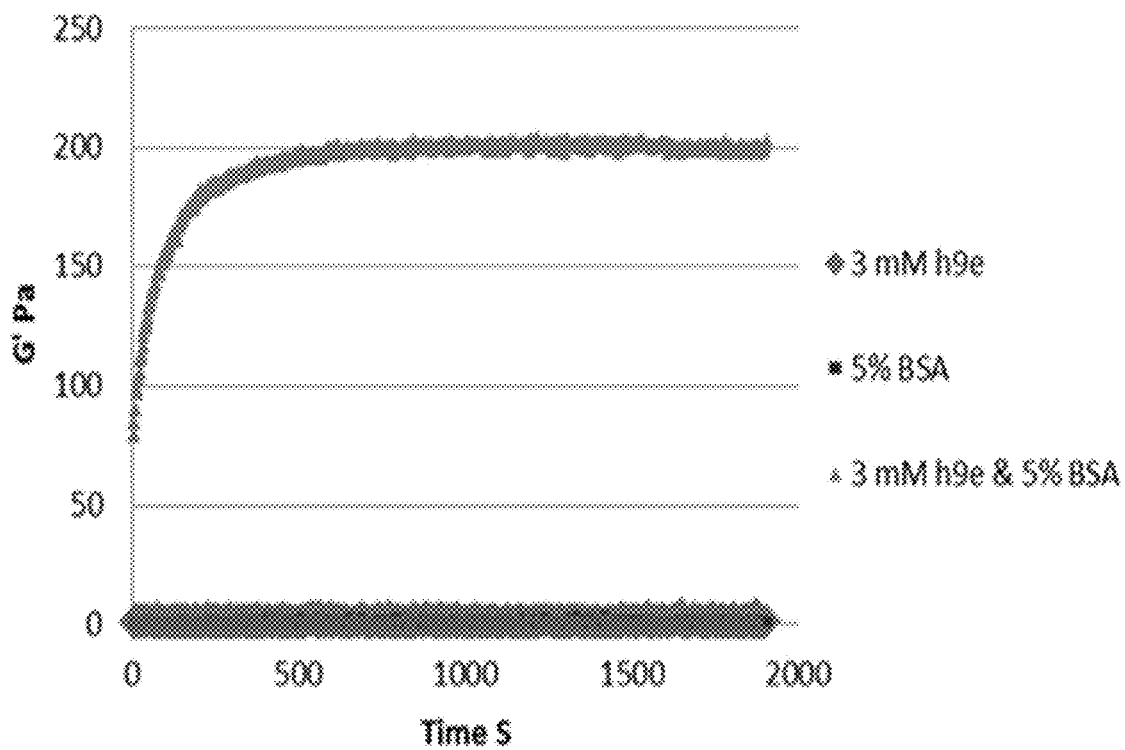
FIG. 2A shows a graph illustrating the mechanical properties of h9e/BSA hydrogel.

To demonstrate this albumin-induced peptide self-assembly pathway, we prepared h9e/BSA and h9e/HSA mixtures and observed them under TEM. FIG. 1 shows that peptide nanofibers bind on the surface of both albumins. FIG. 1a shows the BSA attached to the peptide nanofibers and settled along the fiber growth direction. Similarly, FIG. 1b shows peptide nanofibers touched the surfaces of HSA from one point to another. These visible data confirm the interactions of h9e peptide and albumin molecules. In addition, the hydrogel-forming process was monitored by rheological testing. FIG. 2a presents the storage modulus (G') change of 3 mM h9e peptide solution right after mixing with 5% BSA. In contrast to a 3 mM h9e solution or 5% BSA solution, which performed as Newtonian liquid during the 30 min test, the mechanical strength of the h9e/BSA mixture kept increasing within the first 500 s and reached a stable G' around 200 Pa.

Figure 2B:
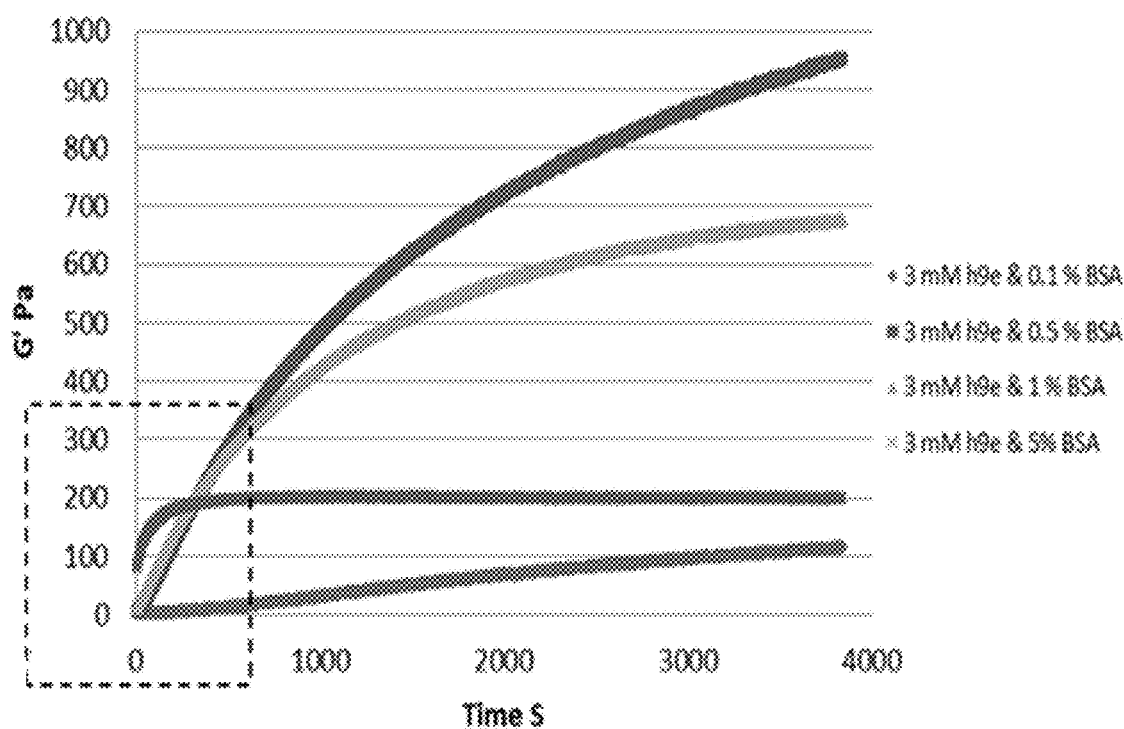
FIG. 2B shows a graph illustrating the mechanical properties of h9e/BSA hydrogel.
Figure 2C:
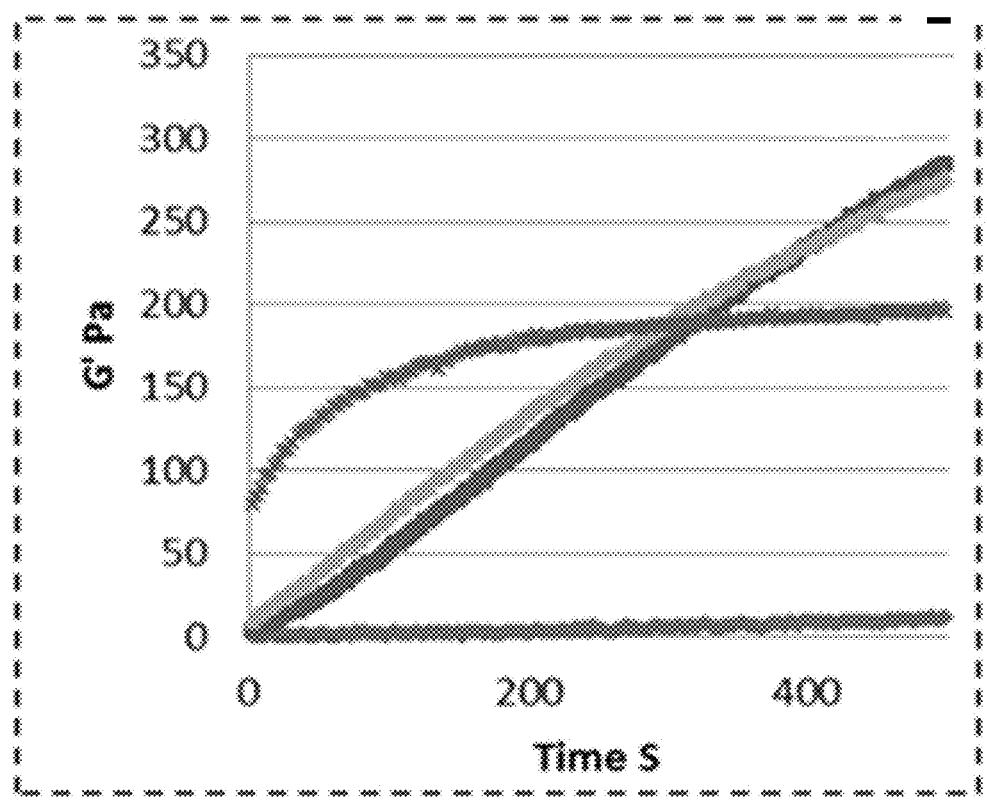
FIG. 2C shows a graph illustrating an enlarged section of FIG. 2B.
Figure 2D:
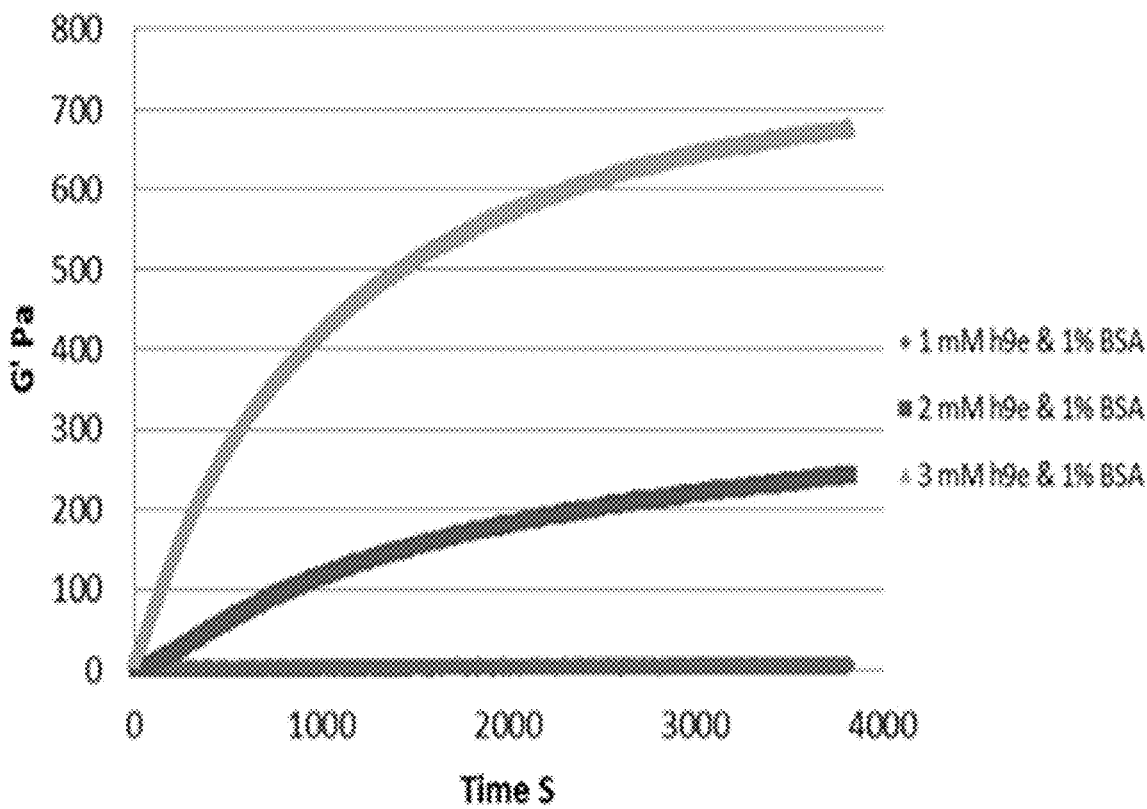
FIG. 2D shows a graph illustrating the mechanical properties of h9e/BSA hydrogel.

The relationship of h9e peptide and BSA was further explored by testing the mechanical strength and hydrogel forming rate of 3 mM h9e with BSA ranging from 0.1 wt % to 5 wt %. FIG. 2b shows an interesting phenomenon: the final strength of the h9e/BSA hydrogel with the same peptide concentration does not correspond to the BSA concentration. For example, after 2 hours of testing, the G' of peptide with 0.1 wt % BSA is about 110 Pa. The G' increased to over 900 Pa for peptide hydrogel with 0.5 wt % BSA but reduced in gradient to 680 Pa and 200 Pa for peptide with 1 wt % and 5 wt % BSA, respectively. On the other hand, the enlarged screen (FIG. 2c) of the first 500 s data shows the increasing rate of G' is consistent with the BSA concentration, which indicates that albumin helps peptide molecules self-assemble into hydrogel; while, as we suggested in our previous study that kinetics is a key factor for peptide self-assembly, relatively lower BSA concentration would allow slower assembling rate for peptide and lead to better nanostructural arrangement for stronger mechanical strength.

Figure 3A:
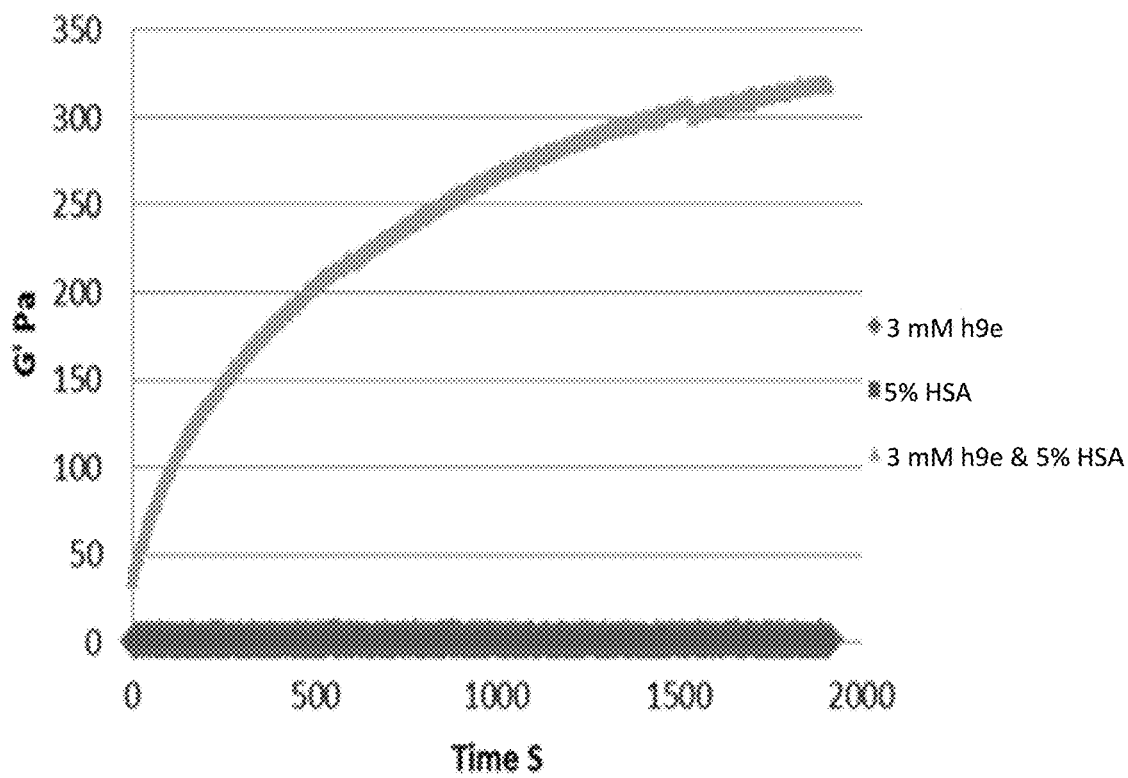
FIG. 3A shows a graph illustrating the mechanical properties of h9e/HSA hydrogel.
Figure 3B:
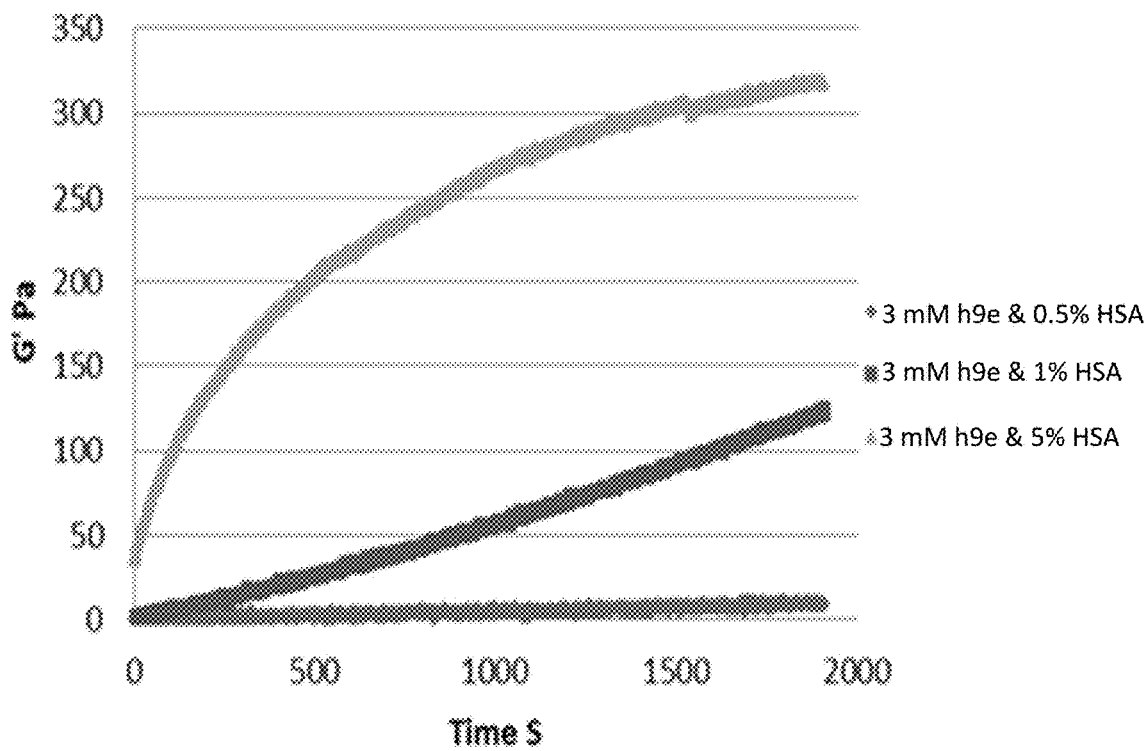
FIG. 3B shows a graph illustrating the mechanical properties of h9e/HSA hydrogel.
Figure 3C:
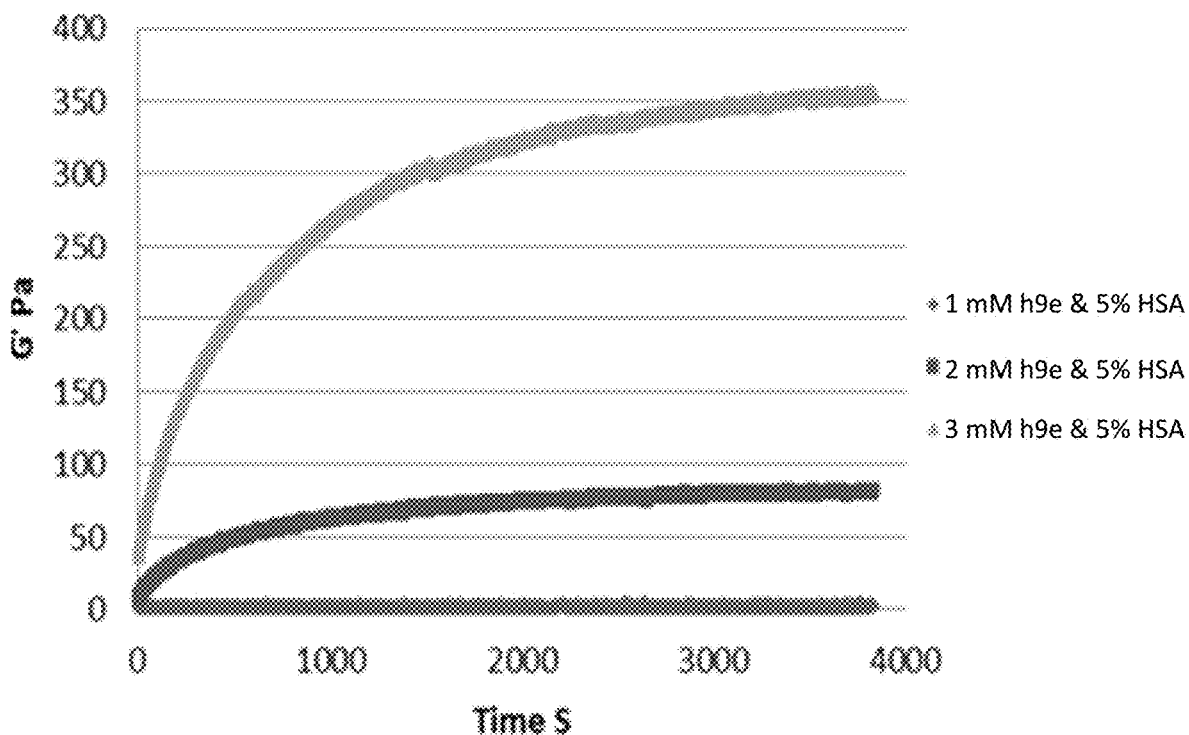
FIG. 3C shows a graph illustrating the mechanical properties of h9e/HSA hydrogel.

The mixtures of different peptide concentration (1-3 mM) with constant BSA concentration (1 wt %) were also studied. Higher peptide concentration leads to stronger and faster hydrogel growth. Solution of 1 mM peptide with 1 wt % BSA performed like a Newtonian liquid after a 2 hour test suggesting an important peptide and BSA concentration may exist for this hydrogel forming process. Similar phenomenon has been found in h9e/HSA mixture (FIG. 3): hydrogel was formed when 3 mM h9e peptide was mixed with 5 wt % HSA (FIG. 3a), and the hydrogel strength and forming rate were more sensitive to HSA concentration compared to h9e/BSA mixture. Hydrogel did not form when peptide concentration was 1 mM or HSA concentration was 0.5 wt %, which again suggested the requirement of the critical concentration of both compounds for h9e/HSA hydrogel formation (FIG. 3 b, c).

Example II

Hydrogel Properties of Peptide h9e in Various Cell Mediums

Background

Two-dimensional (2D) substrates, such as tissue culture polystyrene and the surface of tissue analogs, make an enormous contribution to modern in vitro cell studies; however, traditional 2D platforms cannot accurately mimic the complex 3D architecture of the extracellular matrix (ECM) where native cells reside. In 2D culture, the monolayer cells experience homogenous concentration of nutrients and growth factors which induce unnatural cell environments and cell-cell interactions, yielding a flat and stretched morphology. Recent studies have shown that the morphological differences of cells cultured in 2D and 3D can exhibit several striking differences in subtle cellular processes such as proliferation, apoptosis, differentiation, gene expression, migration, and drug sensitivities. On the other hand, the biological in vivo 3D systems, such as animal models, are expensive and time-consuming. Therefore, advanced in vitro 3D model systems are needed to fill the gap between the inaccurate 2D systems and the animal models to mimic the complexity of the ECM and the physiological relevance of an in vivo biological system.

In the last few decades, hydrogel scaffolds, cross-linked networks that possess high water contents, have attracted more and more attention in an attempt to mimic in vivo conditions for cell culture. The reticulated structure of cross-linked polymer chains with high water contents introduces a number of desirable cellular microenvironment characteristics: 3D spatial support for cell growth; porosities for cell migration; and facile transportation of oxygen, nutrients, waste, and soluble factors. Hydrogels can be formed from a range of natural sources and synthetic materials. Natural gels derived from ECM components and other biological sources such as collagen, fibrin, hyaluronic acid, chitosan, and alginate are biocompatible and inherit bioactivities that promote cell survival, proliferation, differentiation, and cellular function of many cell types. However, natural hydrogels have varying biochemical presentations and material properties that are difficult to control, which increases the risk and complexity of cellular study in this culture system. On the other hand, synthetic gels are highly reproducible with consistent composition and predictable manipulation of properties. However, synthetic polymers such as polyactide and polyglycolide have too large fiber diameter and porous size, which present poor scaffold structure and mechanical properties to accurately mimic the full complexity of the natural environment of cell growth. With the rapid development of rationally designed peptides as biological materials, peptide based hydrogel was considered as one of the most promising materials for 3D cell culture because of its amino acid composition and the structural and mechanical similarity to natural ECM.

In addition, for in vitro 3D cell culture, cell encapsulation and isolation are two critical steps to introduce 3D spatial support for cell growth and to recover embedded cells from the scaffold matrix for downstream studies respectively. For a convenient, effective, and safe encapsulation, cells should be added simultaneously with the initialization of hydrogelation. Therefore, mild and cyto-compatible hydrogel-forming conditions are preferred, to ensure that cells survive comfortably during gel formation. However, the sol-gel transformation of currently used peptide/protein hydrogels (i.e., puramatrix gel, hydromatix peptide hydrogel, and matrigel) is triggered by adjusting pH or temperature (Table 1).

TABLE 1

Comparison of material properties, cell encapsulation/recovery, and handling of different 3D cell culture hydrogels

| Characteristics | h9e | Puramatrix gel (BD Biosciences) [a] | Matrigel (BD Biosciences) [b] | Alginate hydrogel (ALgimatrix) [c] |
|---|---|---|---|---|
| Material | Peptide (19 unit) | peptide (16 unit) | Reconstituted basement membrane extracted from EHS mouse tumor | Polysaccharides (dried sponge) |
| Porosity | 50-200 nm | 50-200 nm | 50-400 nm | 50-200 pm |
| Solution pH | Neutral | Acidic pH 3 | Various during the storage (acidic to physiological pH) | Dry |
| Gel trigger | Hydrogel could be triggered by directly mixing cell medium containing serum or albumin or solution containing Ca2+, Na+ or albumin, or (no pH or temperature adjustment) | Starts gel at pH higher than 4.5-5 (change medium at least 3 steps within first 30 min to equilibrate the sample to physiological pH). | Starts gel at temperature higher than 10° C. | Add gel firming buffer containing Ca2+ |
| Cell encapsulation | Directly mix (pipette), cells suspended in cell medium before the peptide solution is added in a relaxed working environment. Cells are surrounded by medium and nanofibrils network during hydrogelation | Directly mix (pipette, has to be very fast, within 1 min, to shorten the contact time of cell with acidic peptide solution); cells is isolated from medium and prepared in 10% sucrose solution before peptide solution is added | Directly mix with chilled pipette (need to chill everything before experiment because temperature is the trigger for gelation | Immediately centrifuge after the firming buffer added (for better cell distribution) |
| Cell recovery | Pipette, dilute the hydrogel with cell medium 1:15 folds and centrifuge | Pipette to disturb the gel structure and centrifuge | Add cell recovery solution or lowing temperature or centrifugation to disrupt the gel matrix | Add dissolving buffer |

The undesirable low pH or cold temperature of the pre-gel solutions may cause cell death when they are directly mixed. Hydrogel preparation procedures become complex when changing cell medium for pH balance or chilling experimental tools are required (Table 1). Cells kept in sucrose solution or a gel-forming buffer struggle with lack of nutrients up to several hours during gel formation before cell medium can be added. Moreover, isolating cells from the hydrogel matrix is another challenge for 3D cell culture. In most cases, changing the environmental factors back to extreme conditions or adding undesirable buffer for hydrogel degradation are required to initialize the gel-sol transformation before cells can be separated out (Table 1). This process threatens the survival of cultured cells and may cause the failure of the whole downstream studies. Therefore, it is necessary to develop a hydrogel which not only presents a convenient and effective process for cell encapsulation, but also provides an easy and safe cell isolation for further cell physiological and pathophysiological studies.

Materials and Methods

A. Peptide-Medium Hydrogels in Cancer Cell Mediums

A solution of h9e was prepared at neutral pH (~7) and mixed with Minimum Essential Medium (MEM, with 10% FBS (source of albumin)) at room temperature. After mixing, h9e peptides self-assemble into a hydrogel matrix with a final peptide concentration as low as 1 mM (0.17%). Without introducing any additional gel forming buffer or adjusting environmental pH or temperature, this peptide provides a convenient and mild hydrogel forming process and allows cells to be surrounded by their culture medium during cell encapsulation (Table 1). More interestingly, the mechanical strength of this hydrogel matrix exhibits special deformability and reassembly capability, which allow the gel-sol transformation through repeated pipetting.

A breast cancer cell line, MCF-7, was selected as a model to grow in 3D in the h9e-MEM hydrogels. Studies of cell morphology, viability and proliferation showed that cells exhibited 3D cyto-architecture in the hydrogel matrix and kept high bioactivities for further studies after isolation.

1. Peptide Synthesis and Hydrogelation

The h9e peptide was synthesized according to a previously published protocol. Briefly, peptides were synthesized on an automated CEM Liberty microwave peptide synthesizer (CEM Corporation, Matthews, N.C.) according to the base-labile 9-fluorenylmethoxycarbonyl (Fmoc) strategy with Rink amide resin and Fmoc-protected amino acids. After final N-terminal Fmoc group deprotection, the resin-bound peptides were side-chain-deprotected and cleaved using TFA/TIS/water (95/2.5/2.5 v/v). Peptides were precipitated and washed three times with anhydrous ether, dissolved in acetonitrile and deionized water (50/50 v/v), then freeze-dried. Molecular weight and purity of the synthesized peptides were confirmed by matrix-assisted laser desorption/ionization time-of-flight mass spectroscopy and high-performance liquid chromatography.

Lyophilized peptide was added to 100 mM sodium bicarbonate and completely dissolved by magnetic stirring for 3 hours with a final peptide concentration of 10 mM. For hydrogelation, peptide solution was added into MEM with 10% FBS and the mixture was hand-shaken for about 10 seconds. The peptide hydrogel formed within 15 minutes at room temperature with final peptide concentrations of 1, 2, and 3 mM.

2. Rheological Tests

The storage and loss moduli (G' and G", respectively) of h9e hydrogels were determined on a C-VOR 150 rheometer system (Malvern instruments, Malvern, Worcestershire WR141XZ, United Kingdom) with a 20-mm diameter parallel plate geometry and 500 μm gap size. To mimic cell physiological conditions, all rheological tests were performed at 37° C. unless otherwise specified. The peptide and MEM mixture was placed on the measuring system immediately after mixing for a gel-forming rate test. Single frequency (1 Hz) and steady shear strain (1%) were selected for a 1 hour test. To determine the hydrogel reassembly capability, the peptide and MEM mixture was incubated at room temperature overnight for hydrogelation, then transferred to a lower measuring plate for a 10 minute, single-frequency test (1 Hz, 1% strain) for stabilization. The hydrogel was broken using 1 Hz frequency and 500% shear strain for 1 minute. Resetting the instrument parameters took 1 minute, and the hydrogel moduli during the reassembly period were measured under 1 Hz frequency and 1% shear strain for 1 hour. The amplitude sweep test (strain from 1 to 500%, 1 Hz frequency) was conducted multiple times to determine hydrogel reassembly capability after each time it was destroyed. Four testing cycles were applied in this measurement and the hydrogel recovery time between every two cycles was 1, 5, and 10 minutes. Furthermore, to test the response to different environmental temperatures, the peptide hydrogel was measured under a temperature profile test with steady oscillatory frequency (1 Hz) and strain (1%). The temperature was adjusted from 4° C. to 50° C. for two testing cycles. For each cycle, the instrument's heating or cooling processes took 5 minutes, then another 5 minutes to arrive at the setting temperature (4° C. or 50° C.). To determine the G' and G" of hydrogel during cell isolation, 3 mM peptide hydrogel was diluted 15 times with MEM. After thorough mixing, the diluted solution was tested under 1 Hz frequency and 1% shear strain at 4° C. for 1 hour.

3. Scanning Electron Microscopy (SEM)

The nanofiber network of hydrogel scaffolds, as well as surface characteristics of the 3D cultured cells, were observed under SEM. The hydrogel samples were dehydrated with increasing concentrations of ethanol from 50% (v/v) to 100% (v/v) at 5% per step and 15 minutes for each step. The ethanol was then removed by a critical point dryer (Samdri-790B, Tousimis Research Corp., Rockville, Md.). The hydrogel samples with cells were fixed in a 2% paraformaldehyde and 2% glutaraldehyde mixture for 30 minutes before dehydration and critical point drying. Samples were then sputter-coated (Desk II Sputter/etch Unit, Denton Vacuum, Moorestown, N.J.) 3 times (12 seconds each time) with 100% Pt. The SEM observation was carried out with an FEI, Nova NanoSEM 430 (Hillsboro, ON) at 5 kV and through a lens detector.

Results and Discussion

1. Peptide Hydrogelation in MFM

Figure 4A:
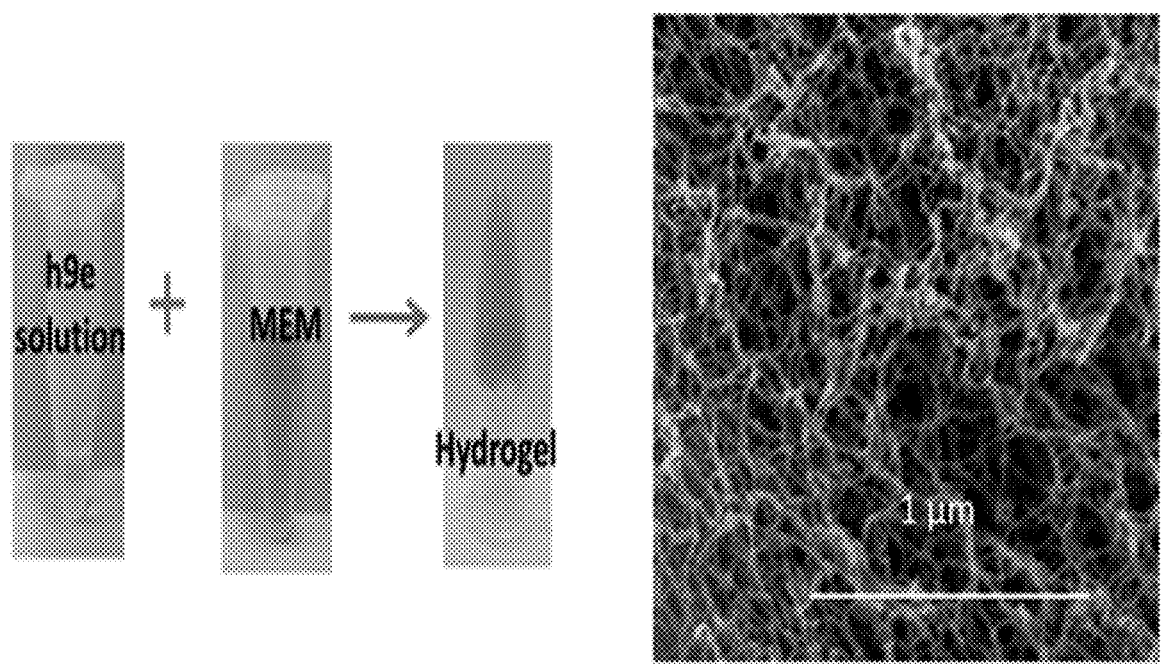
FIG. 4A illustrates a proposed mechanism of MEM-induced h9e peptide self-assembling hydrogelation (SEM image showing the nanofiber scaffold of the hydrogel matrix)

To initiate gel-formation, 100 μl of 10 mM h9e peptide solution (pH 7-8) was added to 900 μL Minimum Essential Media (MEM, with 10% FBS (source of albumin)) to form 1 mL mixture with 1 mM (0.17% w/v) peptide concentration (FIG. 4A). The nanoscale morphology of the hydrogel matrix is presented by the SEM image (FIG. 4A). Peptide hydrogelation induced directly by mixing neutral pH peptide solution with MEM not only avoids the complex chemical gel cross-linking processes, but also utilize a medium commonly used in biological and medical research, providing a physiological condition to cell encapsulation.

Figure 4B:
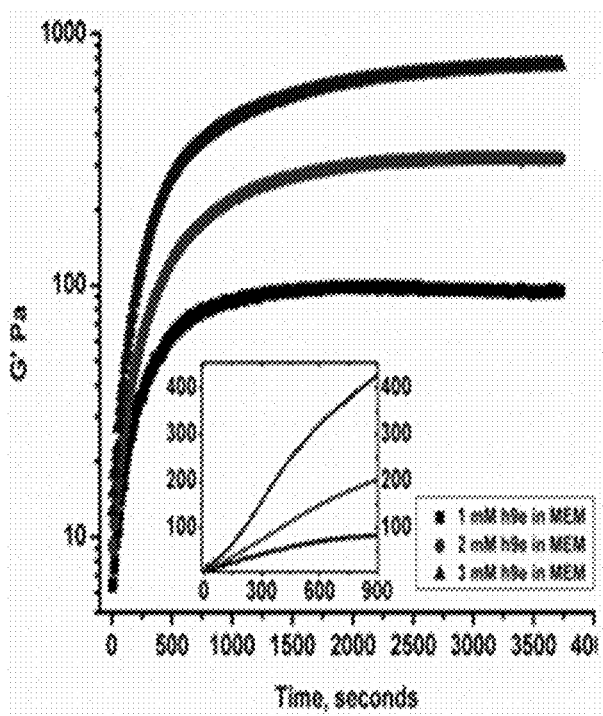
FIG. 4B shows a graph illustrating a storage modulus G' of 1, 2, and 3 mM peptide hydrogel during the hydrogelation at 37° C.
Figure 4C:
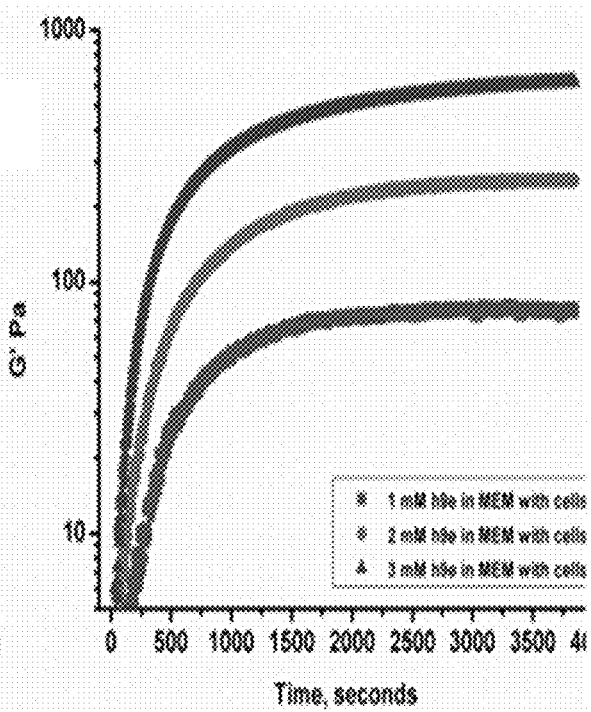
FIG. 4C shows a graph illustrating a storage modulus G' of 1, 2, and 3 mM peptide hydrogel during the hydrogelation at 37° C.

Direct loading of drugs, proteins, or cells during gel formation is one of the most convenient and effective ways for encapsulation. To ensure homogenous distribution of embedded molecules, peptides should assemble as a nanofiber network in a relatively short period with reasonable strength to hold the suspended molecules before their precipitation. To determine the peptide gel-formation rate, we prepared hydrogels with three concentrations, 1 mM (0.17% w/v), 2 mM (0.34% w/v), and 3 mM (0.51% w/v), in MEM. The storage modulus of the solution was measured at 37° C. immediately after thorough mixing. FIG. 4B shows the h9e peptide hydrogel formations with stable storage modules around 100, 400, and 700 Pa, respectively. The gel-formation rates increase with peptide concentrations (inset of FIG. 4B), and all three hydrogels reached a self-supporting strength (close or above 100 Pa) within 15 minutes. SEM images (FIG. 4C, D) indicate that the hydrogel architecture is built by entanglement of 20 nm width nanofibers; however, the lower-concentration hydrogel (1 mM, FIG. 4C) shows a relatively looser matrix structure compared with the compact structure of the higher-concentration hydrogel (3 mM FIG. 4D). This visual evidence further supports the strength differences of different concentration hydrogels.

2. Dynamic Rheological Study of h9e Hydrogel

Figure 4D:
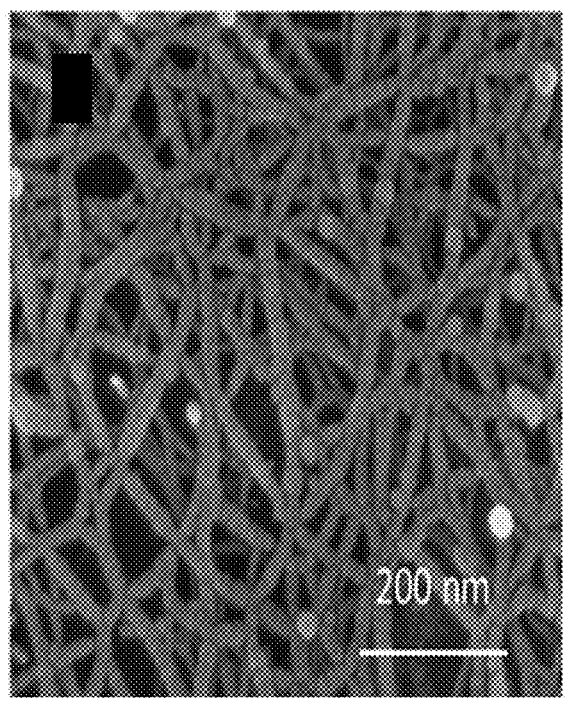
FIG. 4D shows a SEM image of 1 mM peptide hydrogel.
Figure 4E:
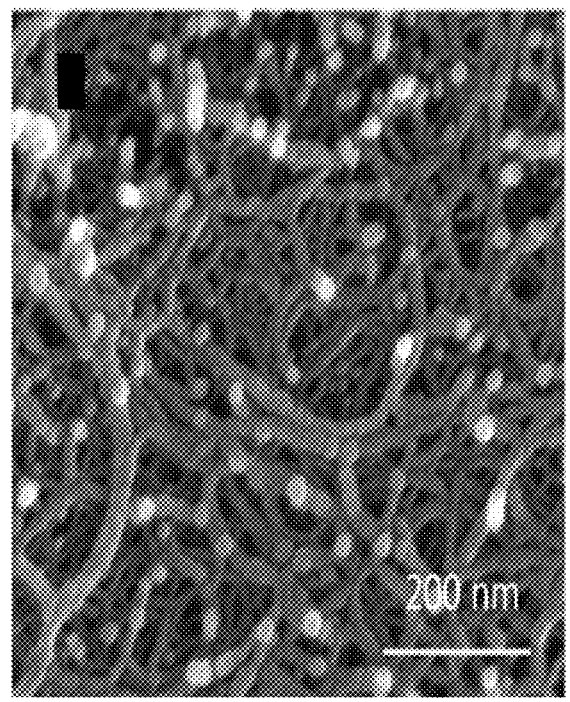
FIG. 4E shows a SEM image of 3 mM peptide hydrogel.
Figure 5A:
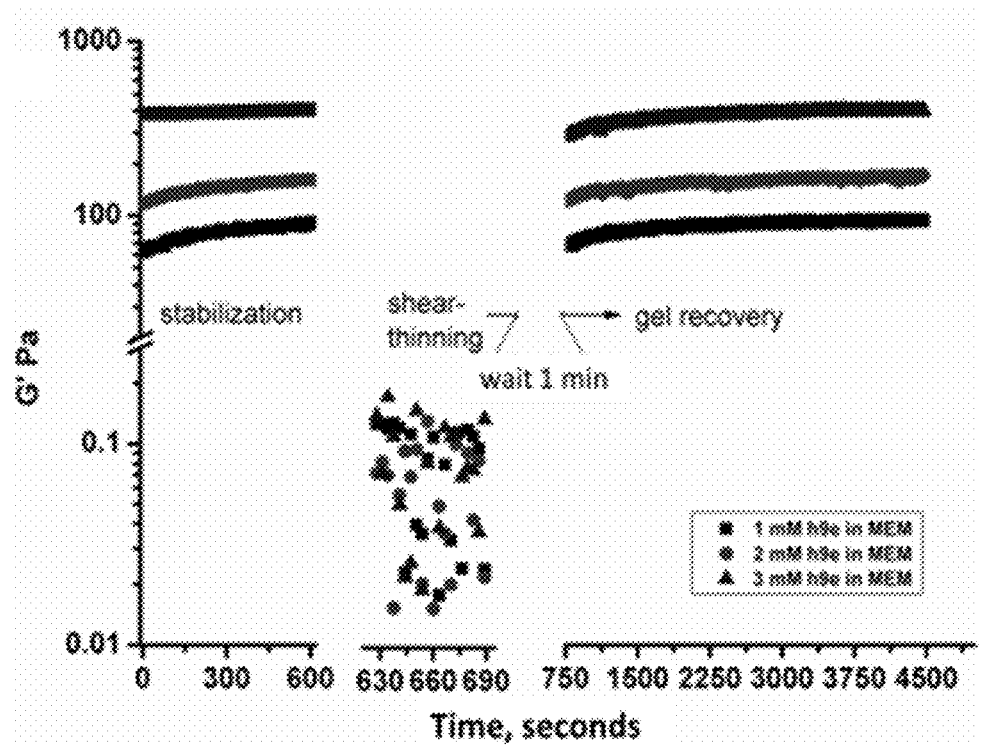
FIG. 5A shows a graph illustrating a storage modulus G' of shear-thinning and recovery test of 1, 2, and 3 mM peptide hydrogel.
Figure 5B:
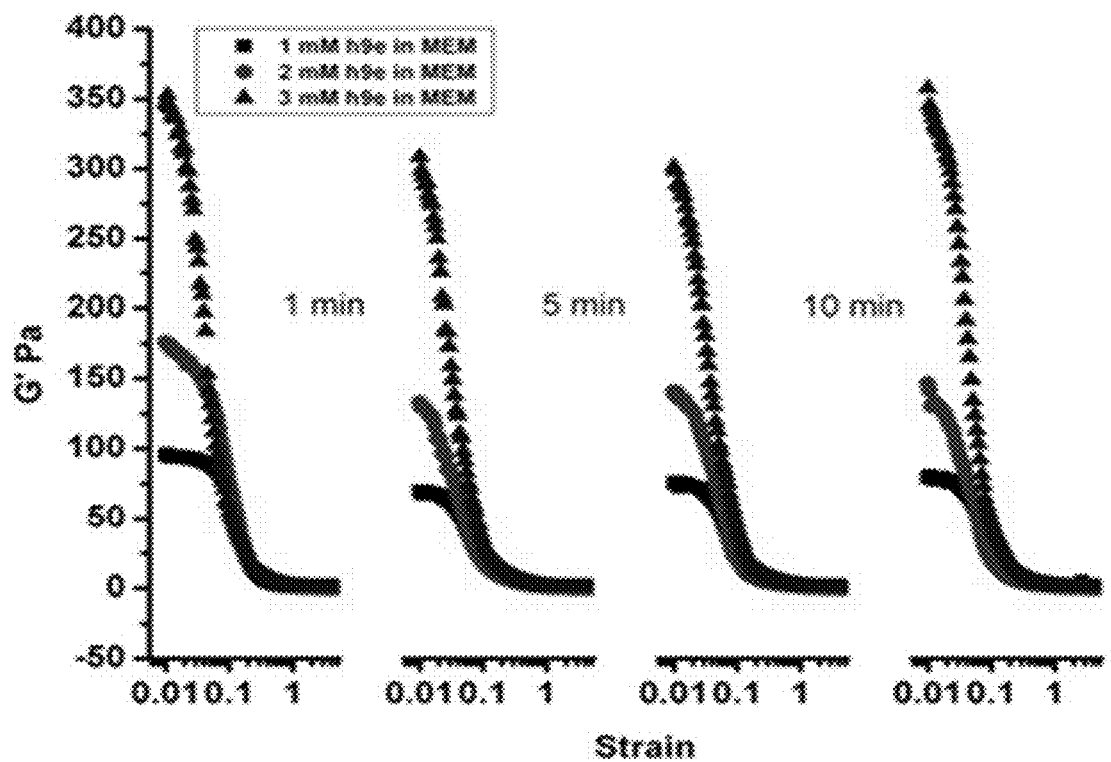
FIG. 5B shows a graph illustrating four times amplitude sweep test with shear strain from 1% to 500% and 1-5-, and 10-min breaks.
Figure 5C:
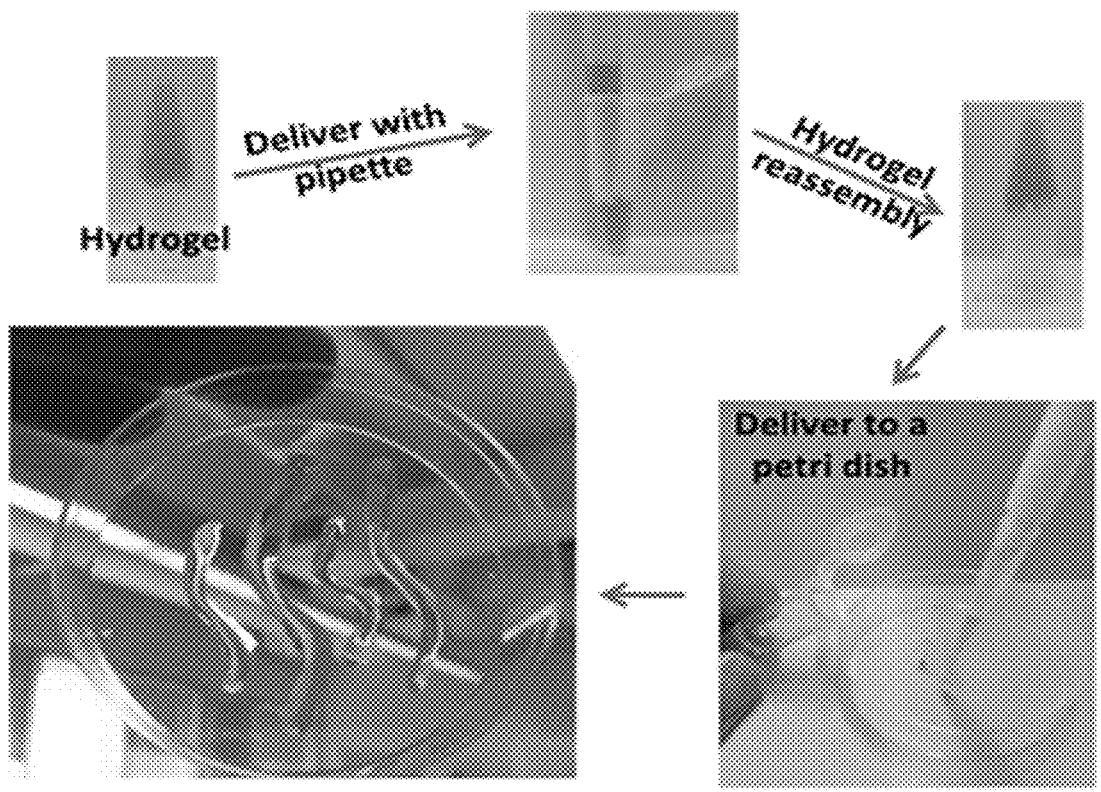
FIG. 5C illustrates multiple times delivery of peptide hydrogel via pipette; hydrogel was shear thinning but reassembled quickly without permanently destroying hydrogel architecture.

The deformability and reassembly ability of MEM-induced h9e hydrogel were assessed by a dynamic rheological test: 1-3 mM peptide hydrogels were stored at room temperature overnight, then transferred to a measuring system and stabilized for 10 minutes. By shear-thinning at 500% strain for 1 minute, all three hydrogels were converted to liquid state, showing a G' lower than 0.2 Pa (FIG. 5A). After shear-thinning stopped, instrument parameters were reset after 1-min waiting time and the hydrogel recovery was monitored using 1% shear strain for 1 hour. The data in FIG. 5A shows the G' of hydrogel recovery during this 1 hour test. To determine whether the hydrogel could maintain this reassembly capability even after shear-thinning many times, the hydrogel was measured under an amplitude sweep test conducted multiple times. Four testing cycles were applied in this measurement and shear strain was increased from 1% to 500% within 5 minutes for each cycles. After that, for hydrogel recovery, the waiting time of 1, 5, and 10 minutes were applied, respectively. FIG. 5B suggests that although the hydrogel architecture was completely broken into liquid form at the end of each cycles, quick reassembly persisted even after shear-thinning multiple times. The results also show that the percentage of recovery G' increased with waiting time and that the hydrogel reassembly rate related to hydrogel concentrations. For example, with a waiting time of 1 min, about 73%, 76%, and 88% of the gel strengths were recovered for 1, 2, and 3 mM hydrogel, respectively, but after three shear-thinning cycles and 10 min waiting, 83% (1 mM), 84% (2 mM), and 100% (3 mM) of the gel strength was recovered (FIG. 5B). The higher reassembly rate is most likely caused by the more compact matrix structure of hydrogel due to higher peptide concentration (3 mM) (FIG. 4D). In the solution with high peptide concentration, some non-covalent gel network cross-links remain intact and the broken nanofiber groups are close to each other, making rebuilding the cross-links easy. Based on these rheological properties, the MEM-induced h9e hydrogel could be delivered via pipette multiple times without permanently destroying the hydrogel architecture (FIG. 5C). This special shear-thinning and recovery property of the hydrogel also provides an alternative method for cell isolation from hydrogel matrix through a mechanical shearing and dilution.

Figure 5D:
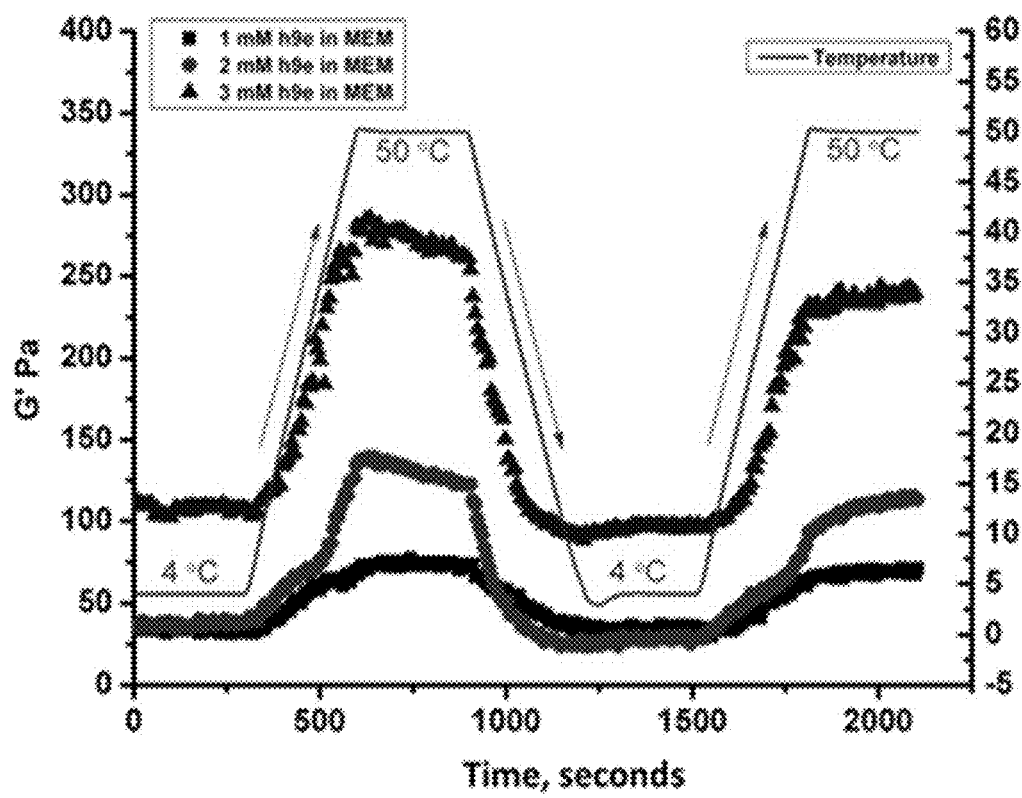
FIG. 5D shows a graph illustrating a temperature profile test of 1, 2, and 3 mM peptide hydrogel between 4° C. and 50° C.

For biological study, temperatures between 4° C. and 37° C. are commonly applied for many standard operational procedures in vitro; therefore, understanding the response of the hydrogel materials to these temperature variations has a large impact on their practical applications. The rheological temperature profile test was performed to address this challenge. The temperature was adjusted from 4° C. to 50° C. for two testing cycles. FIG. 5D shows that the G' of hydrogels moves along with temperature and performs 2-3 times higher at 50° C. than that at 4° C. This thermal response is reversible according to the hydrogel heating and cooling cycles (FIG. 5D). The results provide support for using this peptide hydrogel as a matrix for 3D cell culture: the hydrogel matrix is stiffened for cell encapsulation when it remains at 37° C., but is weakened at 4° C. for cell isolation using standard centrifuge method.

B. Peptide-Medium Hydrogels in Stem Cell Mediums

Two different types of stem cell mediums were selected for this test. One is a low glucose DMEM medium with 2% (v/v) Fetal Bovine Serum (FBS) for Mesenchymal Stromal Cell (MSC medium). The other one is a N2B27 supplemented serum-free 2i medium with 0.5% (v/v) Bovine Serum Albumin (BSA) for rat Embryonic Stem Cell (ESC, 2i medium). The hydrogel formation process was monitored under a time sweep rheological test for 1 hour. The special shear-thinning and self-healing property of h9e peptide hydrogel was also tested. After hydrogel was stable, more cell medium was added to dilute the hydrogel 20 fold; the data of storage modulus (G') was used to demonstrate the cell recovery capability of this hydrogel system. In addition, the stability of hydrogel as well as the peptide solution before the hydrogel formation was also tested.

1. Peptide Synthesis and Hydrogelation

The h9e peptide was synthesized according to the method mentioned above. Lyophilized peptide was added to 100 mM sodium bicarbonate and completely dissolved by magnetic stirring for 3 hours with a final peptide concentration of 10 mM. For hydrogelation, peptide solution was added into MSC medium or 2i medium and the mixture was hand-shaken for about 10 seconds or gently pipette mixed 3 times. The final peptide concentrations were 1, 2, and 3 mM.

2. Rheological Tests

The storage and loss moduli (G' and G", respectively) of h9e hydrogels were determined on a C-VOR 150 rheometer system (Malvern instruments, Malvern, Worcestershire WR141XZ, United Kingdom) with a 20-mm diameter parallel plate geometry and 500 μm gap size at 37° C. The methods for hydrogel formation test and shear-thinning and self-healing test were the same as the methods of cancer cell medium mentioned above. After 24 hours of hydrogel formation, 2 mM peptide hydrogel was diluted 20 fold by adding cell culture medium and thorough mixing by pipette. The diluted solution was transferred to rheometer system and tested under 1 Hz frequency and 1% shear strain at 4° C. for 1 hour.

The stability of h9e-2i medium hydrogel was tested. A plastic tray was placed on the bottom of the well plate. Next, 1 wt % h9e solution was mixed with 2i medium at 1:1 (v:v) ratio in a centrifuge tube and then transferred into the well plate. There was 500 μl peptide hydrogel for each well. The well plate was then placed in an incubator for 1 hour. After hydrogel was stable, another 500 μl of 2i medium was slowly added on the top of hydrogel. The top medium was replaced every other day. For mechanical testing, the top 2i medium was removed and hydrogel was transferred to a dynamic rheometer using the tray. The stability of the peptide solution was also tested using 1 wt % peptide solution stored in 4° C. refrigerator for up to 24 days. Part of the peptide solution was taken out and mixed with 2i medium with 1:1 (v:v) ratio on days 1, 6, 18 and 24. The hydrogel formation process was monitored under the single frequency (1 Hz) rheological test with 1% shear strain for 1 hour.

Results and Discussion

1. Peptide Hydrogel Formation in MSC Medium

Figure 6A:
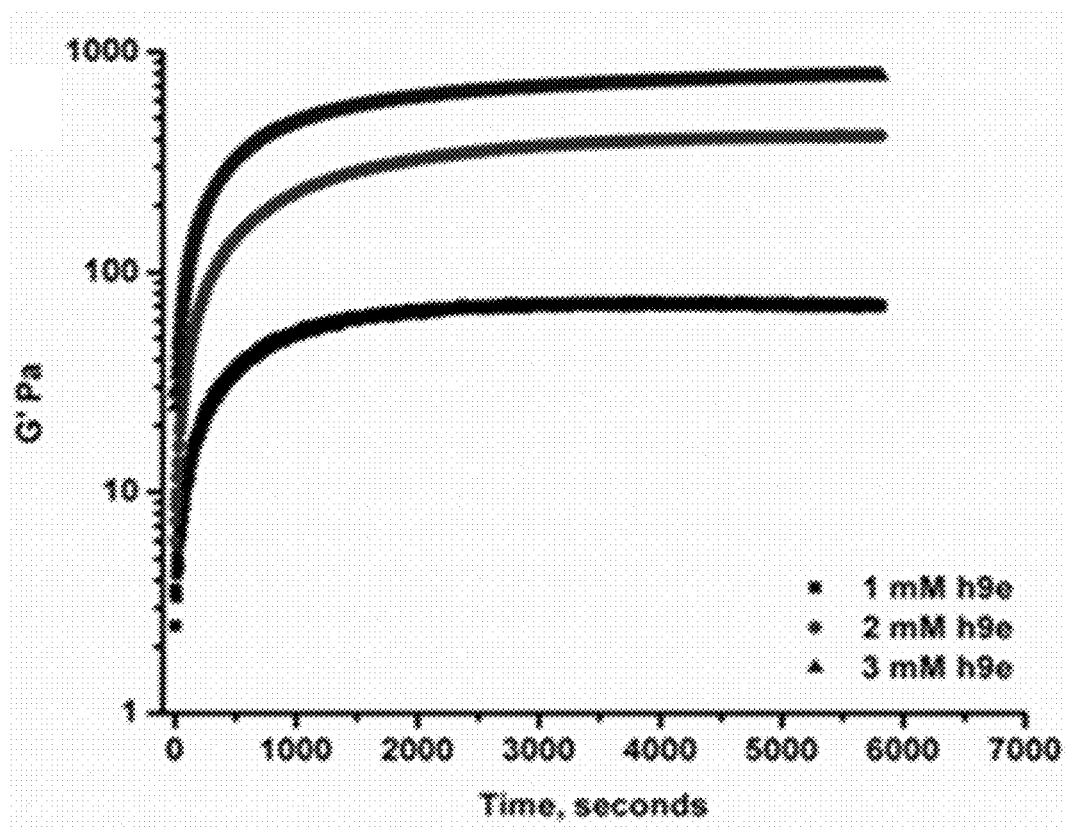
FIG. 6A shows a graph illustrating a storage modulus G' of 1 mM, 2 mM and 3 mM h9e-MSC hydrogel during hydrogel formation.
Figure 6B:
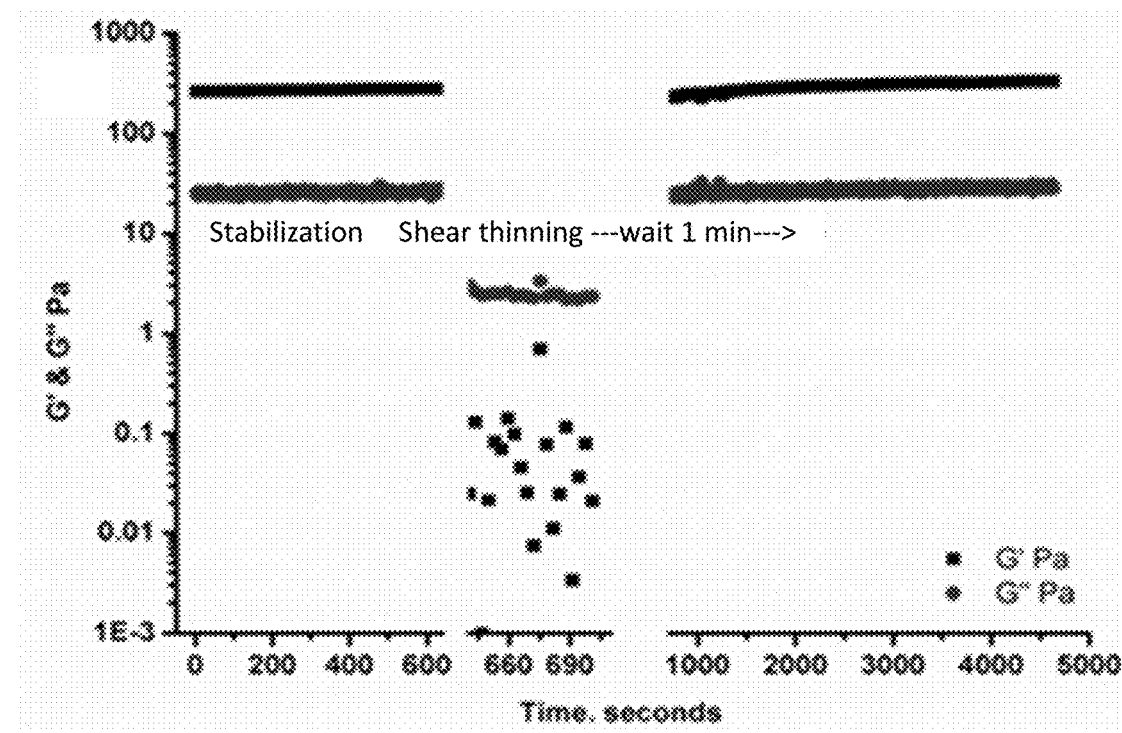
FIG. 6B shows a graph illustrating a storage modulus G' and G" of shear-thinning and recovery test of 2 mM h9e-MSC hydrogel.
Figure 6C:
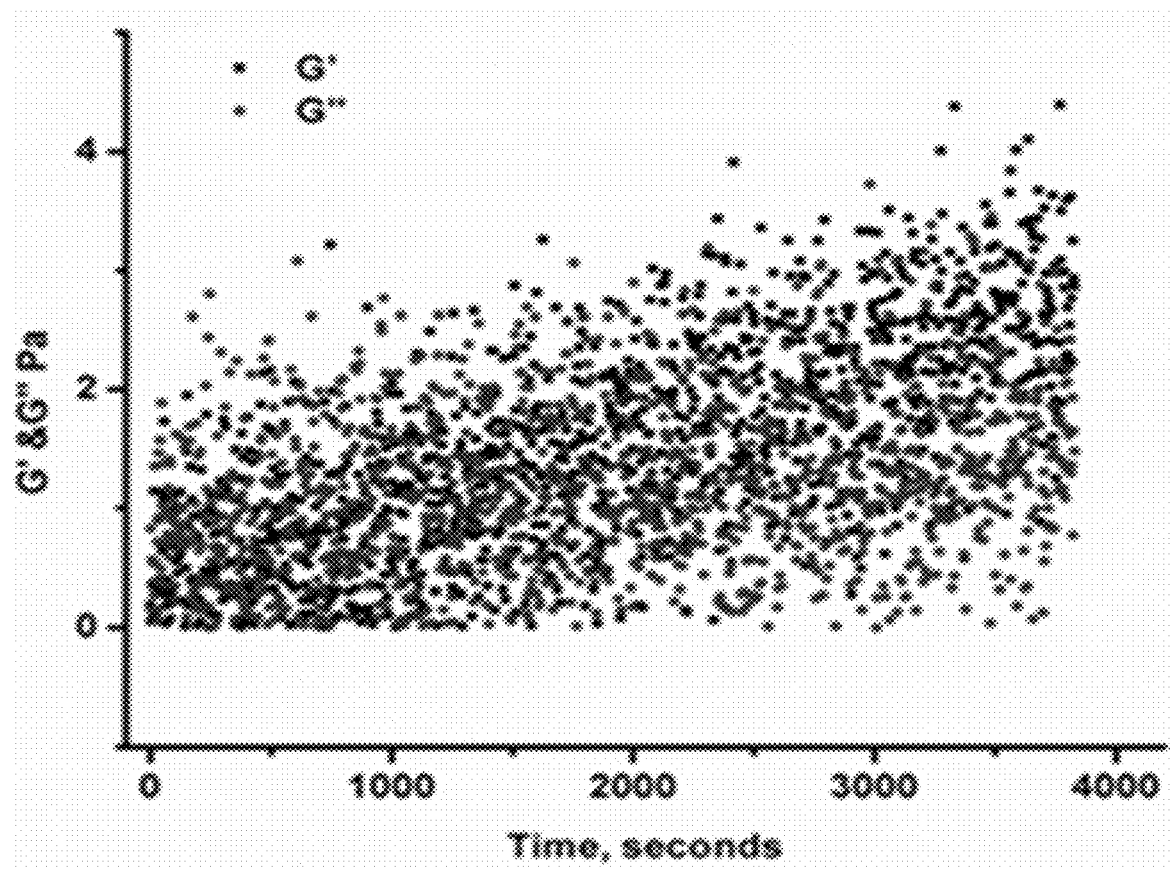
FIG. 6C shows a graph illustrating G' and G" of 2 mM h9e-MSC hydrogel after 20 fold dilution.

Three concentrations (1 mM, 2 mM and 3 mM) of h9e-MSC hydrogel were prepared by mixing 10 mM h9e solution with MSC cell culture medium at 1:9, 2:8 and 3:7 (v/v) ratios. The G' of the peptide-medium mixture was measured right after mixing. FIG. 6a shows that G' of the hydrogel was increase with peptide concentration. The stable G' of 1 mM, 2 mM and 3 mM h9e-MSC hydrogel was 70 Pa, 350 Pa and 800 Pa respectively. The 2 mM h9e-MSC hydrogel was selected for shear-thinning and re-healing test (FIG. 6b). A sample was stored at room temperature overnight and stabilized on the measuring system for 10 min. Under the 500% shear strain, the hydrogel was disturbed into liquid form with G' lower than 0.2 Pa. After the shear ceased for 1 min, greater than 90% of gel strength was recovered. In the following one hour 1% shear strain recovery test, 100% of the hydrogel mechanical strength was recovered within a few minutes (FIG. 6b). To determine the cell recovery capability of this h9e-MSC hydrogel, cell medium was added to a stable hydrogel. After thorough mixing by pipette, the peptide concentration of the hydrogel was diluted 20-fold from 2 mM to 0.1 mM. The diluted solution was then transferred to a rheometer for single frequency testing. FIG. 6c shows that during the 1 hour test, both the G' and G" of the solution was lower than 4 Pa, presenting as a very low viscous solution. This phenomenon ensures h9e-MCS hydrogel can be converted into liquid form and allows cell isolation after 3D cell culture.

2. Peptide Hydrogel Formation in 2i Medium

Figure 7A:
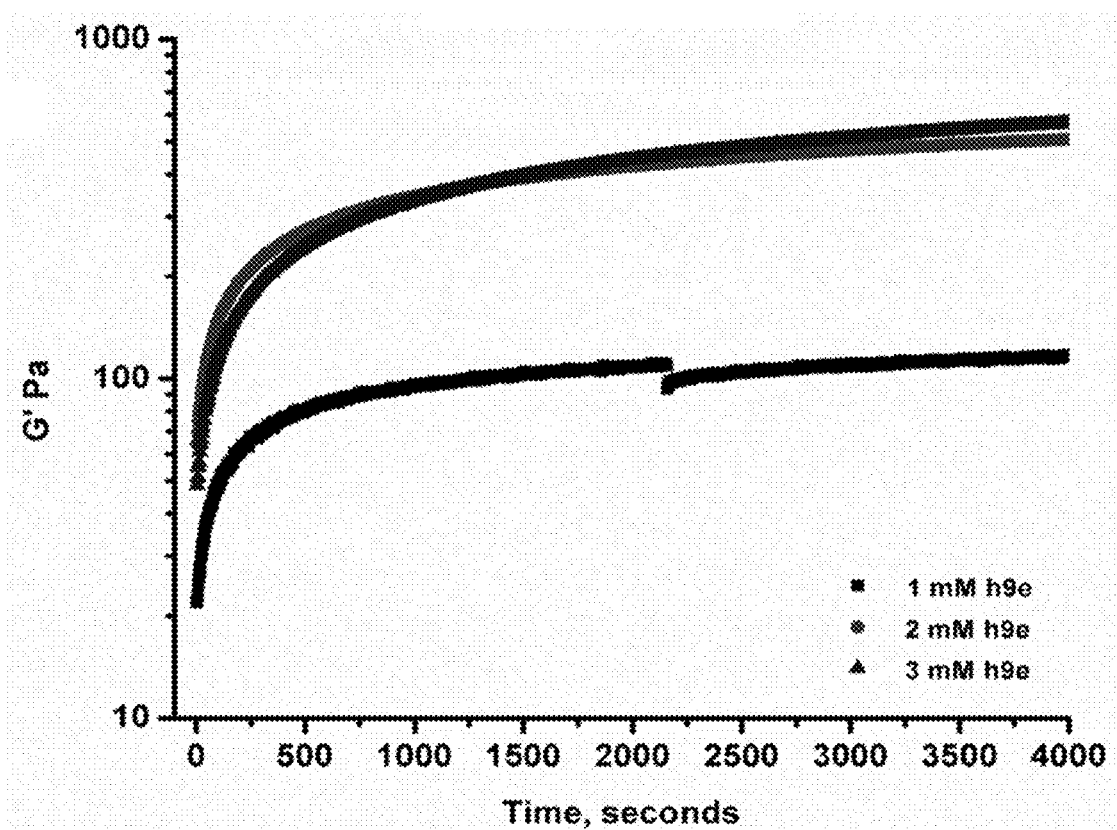
FIG. 7A shows a graph illustrating a storage modulus G' of 1 mM, 2 mM and 3 mM h9e-2i hydrogel during hydrogel formation.
Figure 7B:
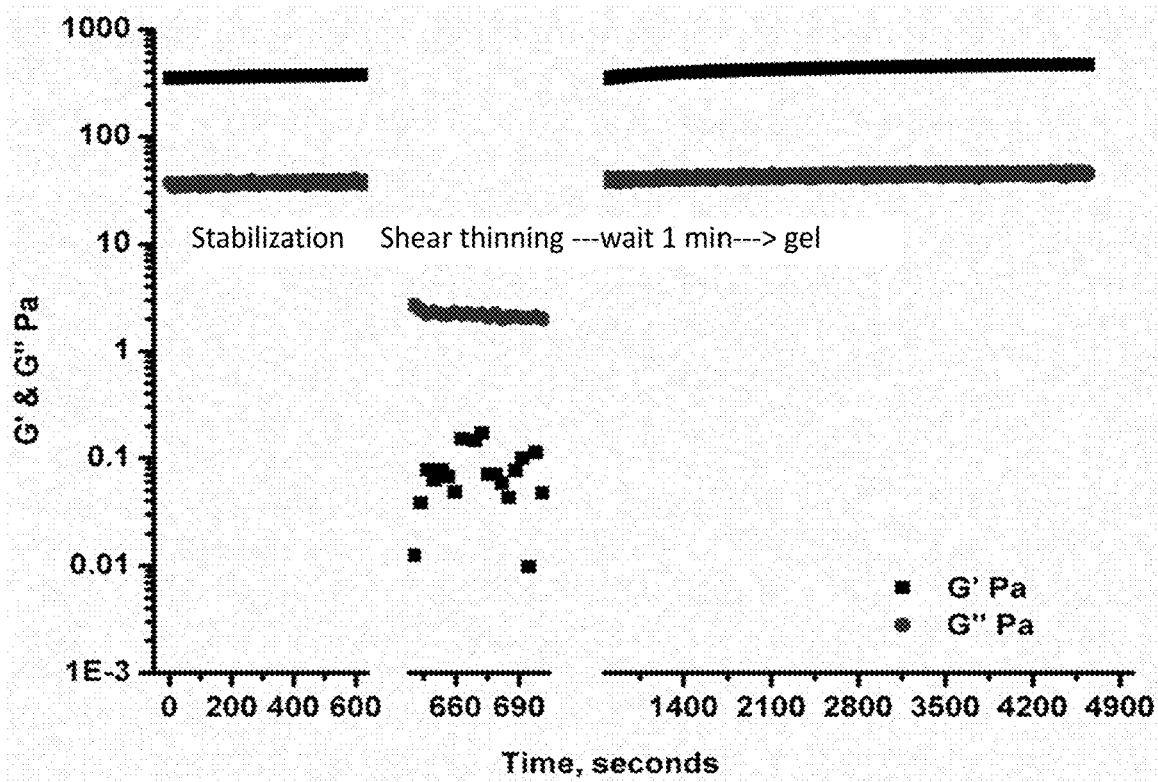
FIG. 7B shows a graph illustrating a storage modulus G' and G" of shear-thinning and recovery test of 2 mM h9e-2i hydrogel.

Three concentrations (1 mM, 2 mM and 3 mM) of h9e-2i hydrogel were prepared in the same way as h9e-MSC hydrogel. FIG. 7a shows that G' of 1 mM is about 100 Pa. Hydrogels with 2 mM and 3 mM peptide concentration in 2i medium each have similar stable G' of 600 Pa. The 2 mM h9e-2i hydrogel was selected for shear-thinning and re-healing test (FIG. 7b) by using the same method described for the h9e-MSC hydrogel. After the hydrogel was sheared into a liquid state (G'<0.2 Pa), the G' of hydrogel was rapidly recovered after shear force was ceased. The mechanical strength of the hydrogel was 100% restored within a few minutes of the 1 hour 1% shear strain recovery test (FIG. 7b). Furthermore, we also diluted the 2 mM h9e-2i hydrogel to a 0.1 mM concentration and demonstrated this method could be used to convert h9e-2i hydrogel into liquid form for cell recovery (FIG. 7c).

Moreover, the stability of h9e-2i hydrogel was also tested. FIG. 8a shows the G' of h9e-2i hydrogel was stable around 130-160 Pa during 7 days. On the other hand, the stability of h9e solution was tested by monitoring the hydrogel formation of h9e-2i mixture after the h9e solution was stored at 4° C. for 1, 6, 18 and 24 days. FIG. 8b shows that after 24 days storage, the h9e solution could still form a hydrogel when mixed with 2i medium and presented the same rate of hydrogel formation and stable G' value. A recent study indicated that the stability of h9e solution could exceed 2 months.

Example III

Peptide Hydrogel and Hemostasis (In Vitro Analysis)

Figure 9:
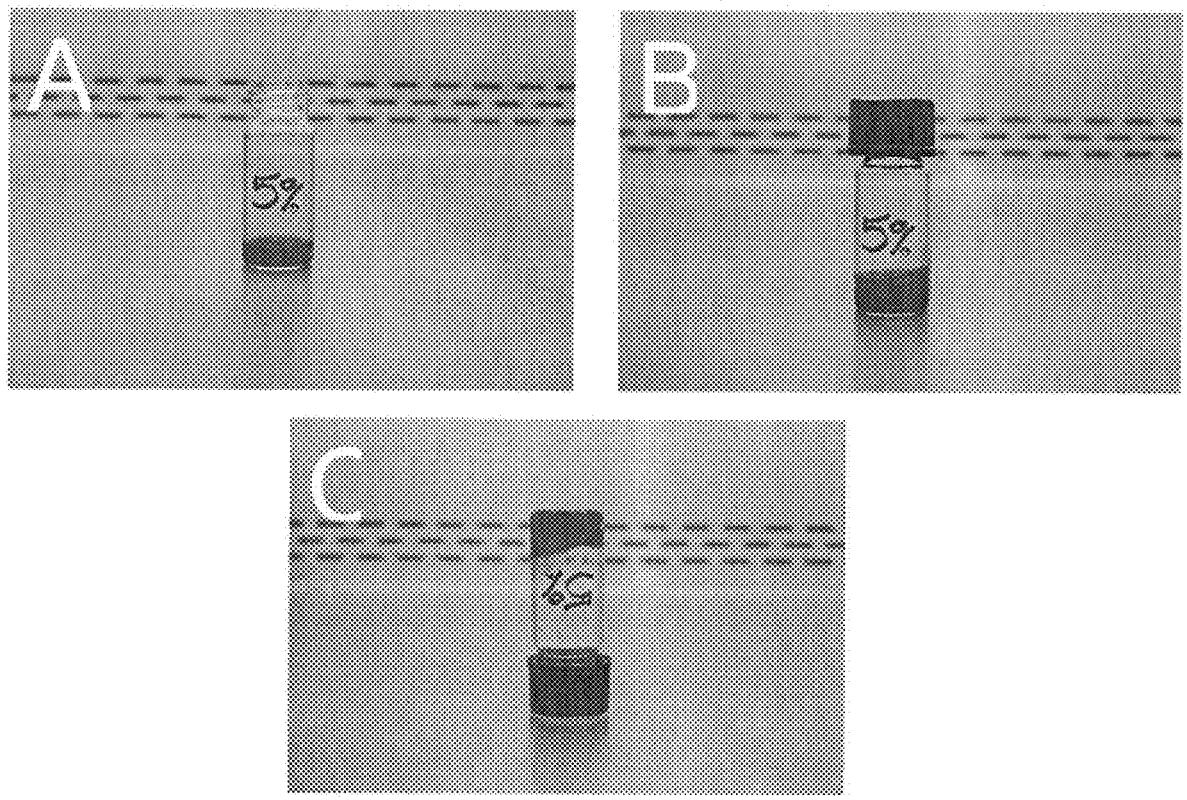
FIG. 9 are photographs showing visual hydrogel formation of blood with 5% h9e peptide solution. A. Commercial mouse blood only. B. Commercial mouse blood and h9e peptide solution. C. Commercial mouse blood and h9e peptide solution three seconds after homogenization.

Visual Hydrogel formation: We demonstrated the ability of the novel h9e peptide to form a stable hydrogel with commercial mouse blood at the following wt % concentrations of h9e peptide solution: 1%, 2%, 3%, 4%, and 5%. About 150 µL of the appropriate wt % of peptide solution was added to 150 µL of commercial mouse blood in a small vial. The mixture was pipetted 5 times to ensure continuity and observed for visual hydrogel formation. Visual observation of hydrogel formation was recorded via a Nikon Coolpix L22 camera (FIG. 9).

Hydrogel gelation time sweep (instantaneous): A time sweep was conducted on the hydrogel and commercial mouse blood mixture. 150 µL of the appropriate wt % of peptide solution was added to 150 µL of commercial mouse blood in a small vial. The mixture was pipetted about 5 times to ensure continuity and added to the rheometer for evaluation. Both storage and loss moduli, G' and G" respectively, of the h9e/blood hydrogel were determined using a C-VOR 150 rheometer (Malvern Instruments, Malvern, Worcestershire, United Kingdom). A plate 20 mm in diameter was used with 1% strain and frequency of 1 Hz at a 37° C. temperature for 30 minutes.

Hydrogel stability gelation time sweep (24 hours post gelatinization): A time sweep was conducted on the hydrogel and commercial mouse blood mixture. 24 hours post gelation. 150 µL of the appropriate wt % of peptide solution was added to 150 µL of commercial mouse blood in a small vial. The mixture was pipetted about 5 times to ensure continuity and stored in a $CO_2$ incubator for 24 hours (Nuaire, Plymouth, Minn., United States). After 24 hours of a hydrogel formation, the hydrogel was added to the rheometer for evaluation. Both storage and loss moduli, G' and G" respectively, of the h9e/blood hydrogel was determined using a C-VOR 150 rheometer (Malvern Instruments, Malvern, Worcestershire, United Kingdom). A plate 20 mm in diameter was used with 1% strain and frequency of 1 Hz at a 37° C. temperature for 30 minutes Results Visual Hydrogel formation: All concentrations of h9e tested formed a visible hydrogel with the commercial mouse blood. The 4% and 5% wt concentration mixtures were stable hydrogels instantly and the 1% and 2% wt concentrations form a stable hydrogel within a few min.

Figure 10:
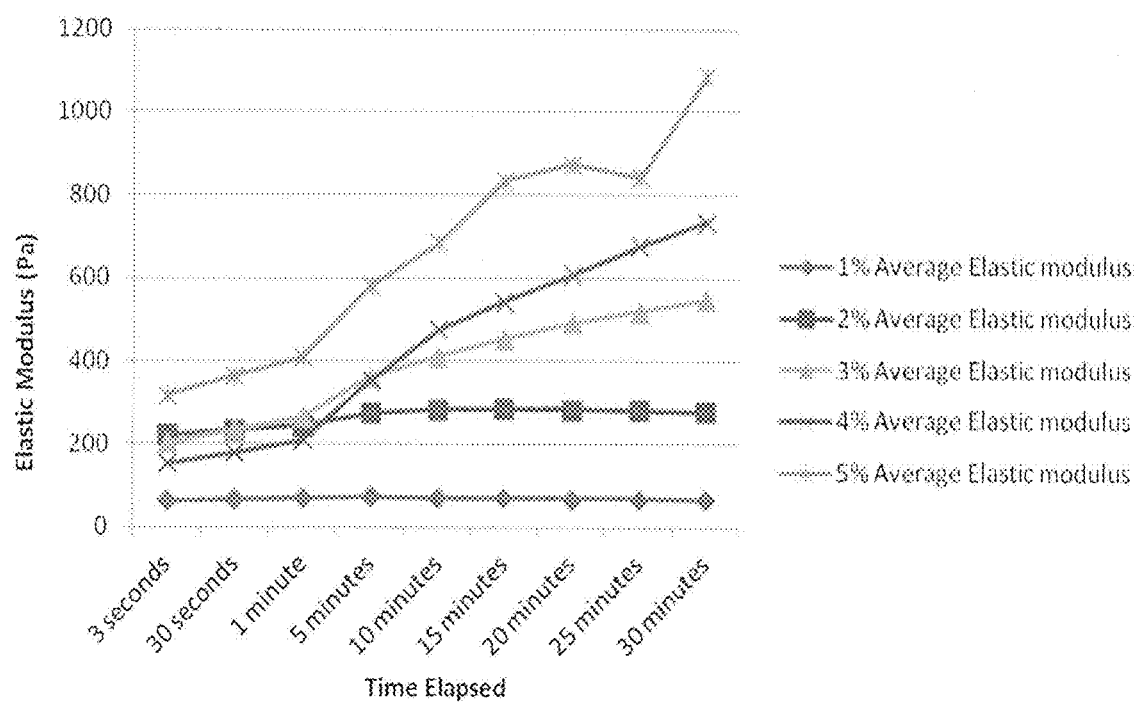
FIG. 10 shows a graph of the Gelation Kinetics of instantaneous blood with h9e solution at varied h9e concentration.

Hydrogel gelation time sweep (instantaneous): All h9e % wt concentrations formed gel with strength above 100 Pa within 1-3 seconds except the 1% wt concentration. Overall, hydrogel formation and time sweep results are a direct measurement of the strength of the interactions within the h9e/blood hydrogel. The 1% and 2% wt concentration mixtures took longer time to form the gel with lower Pa strengths due to the weaker interactions between h9e and albumin molecules. The 4% and 5% wt concentration mixtures formed gel in a few seconds with higher Pa strengths due to stronger interactions between h9e and albumin molecules. FIG. 10.

Figure 11:
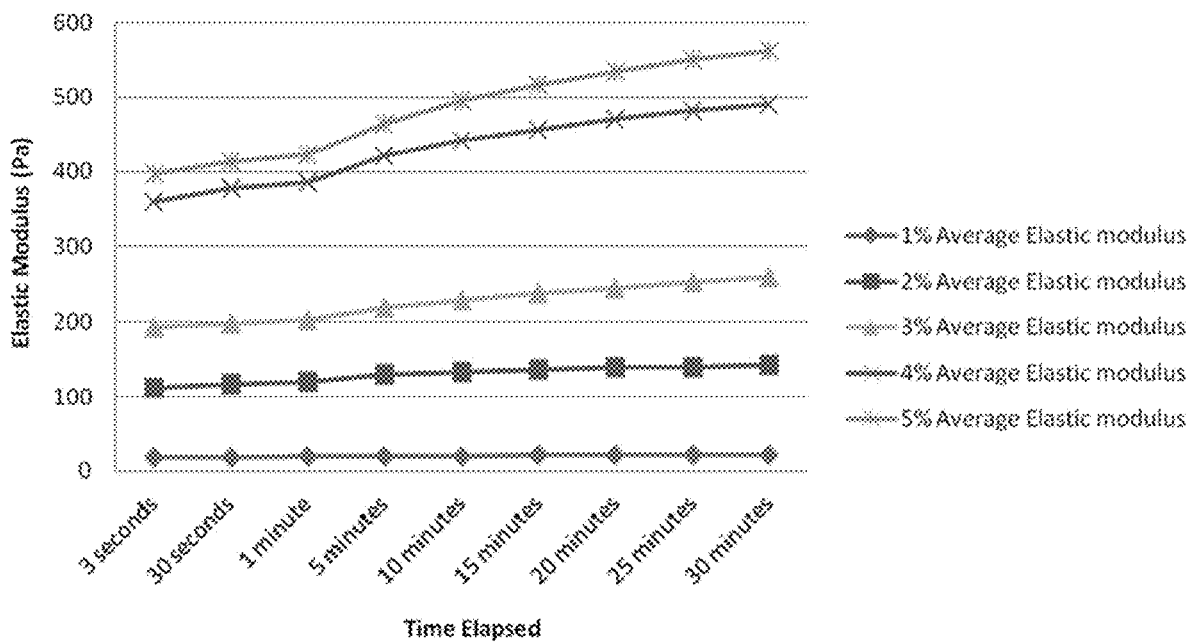
FIG. 11 shows a graph of the Gelation kinetics of blood with h9e solution after 24 hours post gelation at varied h9e concentration.

Hydrogel stability and gelation time sweep (24 hours post gelation): Compared to the instantaneous hydrogel gelation time sweep, the viscosity, strength, and stability of all concentrations, with the exception of the 1%, of h9e/blood hydrogel increased when allowed to sit 24 hours post gelation, then leveled off. The post strength stability property should be desirable for hemostatic agent uses. It is important to note that, compared to the instantaneous hydrogel gelation time sweep the points plotted on the graph are more parallel with the X axis. This indicates that within 24 hours, the h9e/blood hydrogels may be reaching or may have reached their maximum Pa strength. FIG. 11.

Discussion: H9e peptide at 3% to 5% wt can form soft gels in a few seconds with commercial mouse blood. The gel strength is in the range of 100 pa to 800 pa, which has great potential for hemostatic applications. The 1% and 2% wt h9e can also form gels with the mouse blood but need a few minutes to form and resulted in lower gel strength.

Example IV

In Vivo Hemostatic Efficiency in Rat Model

Similar to the method used by Mortazavi et al., in this study 30 rats were divided randomly into 5 groups of 6 animals each. FIG. 10 shows the scheme procedure of the in vivo experiment. Male Wistar rats were kept on AIN-93 diet with free access to water, under 12-h light-dark cycles, for one week. Before excising the tail, the rats were first anesthetized and maintained with 3% isoflurane until the eyelid closure reflex was lost and there was no reactive reflex in response to a toe pinch. In order to maintain an appropriate body temperature during anesthesia, a circulating water blanket was used at a temperature of 41-43° C. Following anesthesia, animals' tails were cut off at a thickness of 5 mm using a pair of mortuary scissors. The cut tail was immediately inserted into a small vial containing the appropriate treatment. The 1st group received topical saline solution (negative control) and the $2^{nd}$ to $4^{th}$ groups received topical h9e peptide solution at 1, 3, or 5 wt %, respectively. The $5^{th}$ group received a topical application of a commercially available hemostatic agent as a positive control (Moore Medical CELOX* Hemostatic Granules). After treatment with above mentioned agents, the volume of blood lost was measured using a scaled test-tube. The bleeding time was measured using a stop watch. At the conclusion of the study, the rats were sacrificed using a $CO_2$ chamber.

Results: The in vivo experiment with rats demonstrated that at 5% h9e solid content, by dipping the cut-rat tail into the h9e solution for a few seconds, the rat tail stopped bleeding in 94 seconds which is a much shorter time than for those tails that were treated with the commercial hemostasis Celox (~225 seconds) and when compared to the rat tails with no treatment (~521 seconds). In terms of blood loss: the rats with 5% h9e treatment lost only 0.75 g blood, compared to the rats treated with Celox (~1.53 g), and the rats without treatment (~2.8 g).

Discussion: All percent concentrations of h9e peptide solution were effective in controlling hemorrhage in comparison to the sterile saline negative control (see table below). The 5% h9e solution was able to outperform the negative control and the commercial, hemostatic agent (Celox™ granules). In conclusion, h9e can be a powerful hemostasis agent in various forms, such as external, internal, solution injection, wound healing patch or bandage.

TABLE 2

| Test Group | Animal Body weight ± SD (grams) | Blood Lost ± SD (mL) | Bleeding Time ± SD (seconds) |
| --- | --- | --- | --- |
| Saline (Negative Control) | 245.85 ± 10.36 | 2.76 ± 0.66 | 521.33 ± 54.67 |
| 1% h9e solution | 239.33 ± 12.22 | 2.20 ± 0.81 | 203.33 ± 57.39 |
| 3% h9e solution | 252.05 ± 9.42 | 1.87 ± 0.90 | 226.00 ± 58.79 |
| 5% h9e solution | 253.45 ± 17.39 | 0.75 ± 0.29 | 94.00 ± 37.05 |
| Celox | 254.91 ± 14.31 | 1.53 ± 0.87 | 225.20 ± 56.21 |

Example V

Additional Sequences

Peptide sequences were as follows:

```
                                            (SEQ ID NO: 1)
Sequence 1: FLIVIGSIIGPGGDGPGGD (SEQ ID NO: 67)
Sequence 3: FLIVIGSIIPGGGDGPGGD (SEQ ID NO: 68)
Sequence 4: FLIVIGSIIGPGVDPGGAD
```

Sequence 1 is the regular h9e sequence. To form sequences 3 and 4, the hydrophilic segment (eD2) of the original h9e peptide was modified. In sequence 3, the Glycine (G) and Proline (P) amino acids, closest to the hydrophobic segment, are reversed. To form sequence 4, four amino acid substitutions were made including a Valine (V) in place of a Glycine (G), a Proline (P) in place of a Glycine (G), a Glycine (G) in place of a Proline (P), and an Alanine (A) in place of a Glycine (G).

Peptide synthesis: Similar to the methods published by Huang et al., experimental peptide sequences 1 as the regular h9e peptide; sequence 3 is the one with GP switched into PG of the hydrophilic segment; sequence 4 is the one by replacing the 4th G with V and 9th G with A. These sequences were synthesized on a CEM Liberty microwave peptide synthesizer (CEM Corporation, Matthews, N.C.). After synthesis was complete, peptides were washed three times with anhydrous ether, dissolved in acetonitrile and distilled (DI) water (50/50 v/v), and then freeze-dried.

Sequence 3 and 4 were synthesized commercially by Peptide 2.0 (Chantilly, Va.). Hydrogel preparation and Instantaneous gelation time sweep Similar to the methods used in U.S. 2013/0018004. Hydrogels were prepared with peptide 1, 3, and 4 alone, or mixture of peptide sequence 1 and 4 at 1:1 ratio. Hydrogels were triggered by calcium ions and BSA alone or co-trigger (calcium ions+BSA).

Figure 12:
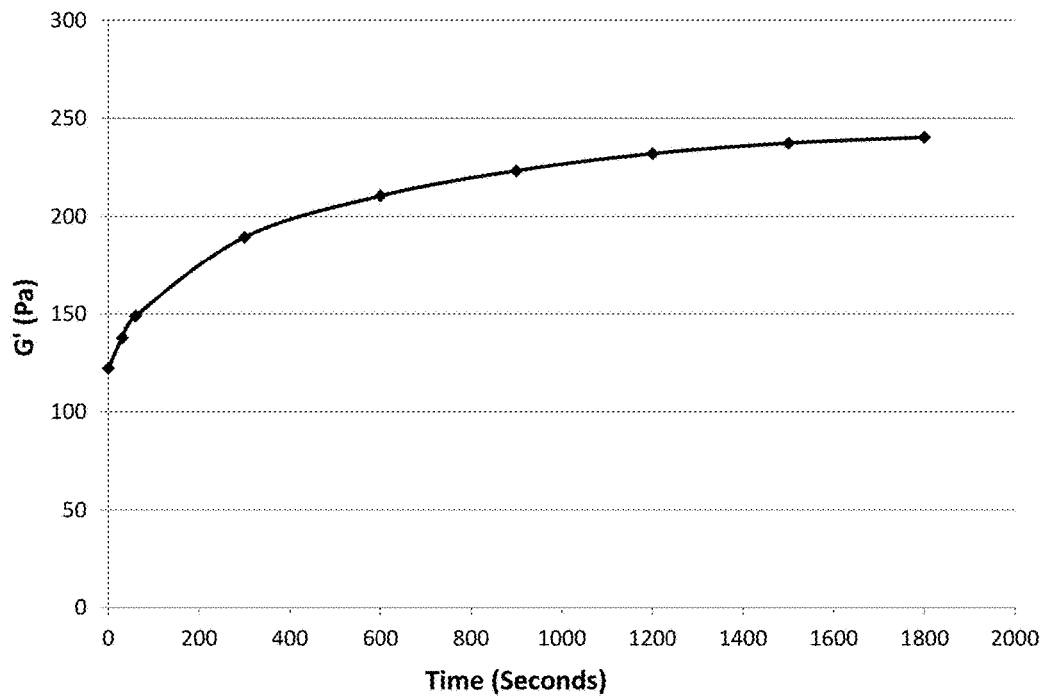
FIG. 12 shows a graph of instantaneous gelation time sweep test: Storage modulus vs time of regular h9e sequence 1, triggered with 100 mM $CaCl_2$) solution.
Figure 13:
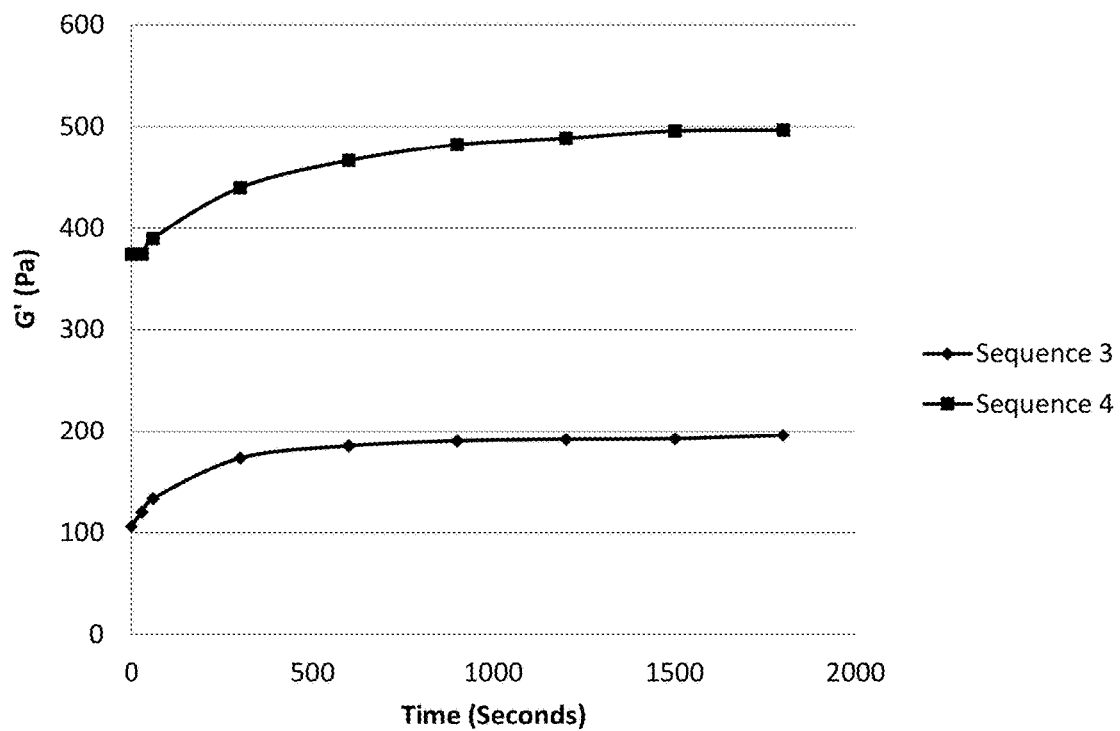
FIG. 13 shows a graph of instantaneous gelation time sweep test: Storage modulus vs time of sequence 3 (SEQ ID NO:67) and sequence 4 (SEQ ID NO:68), triggered with 100 mM $CaCl_2$) solution.
Figure 14:
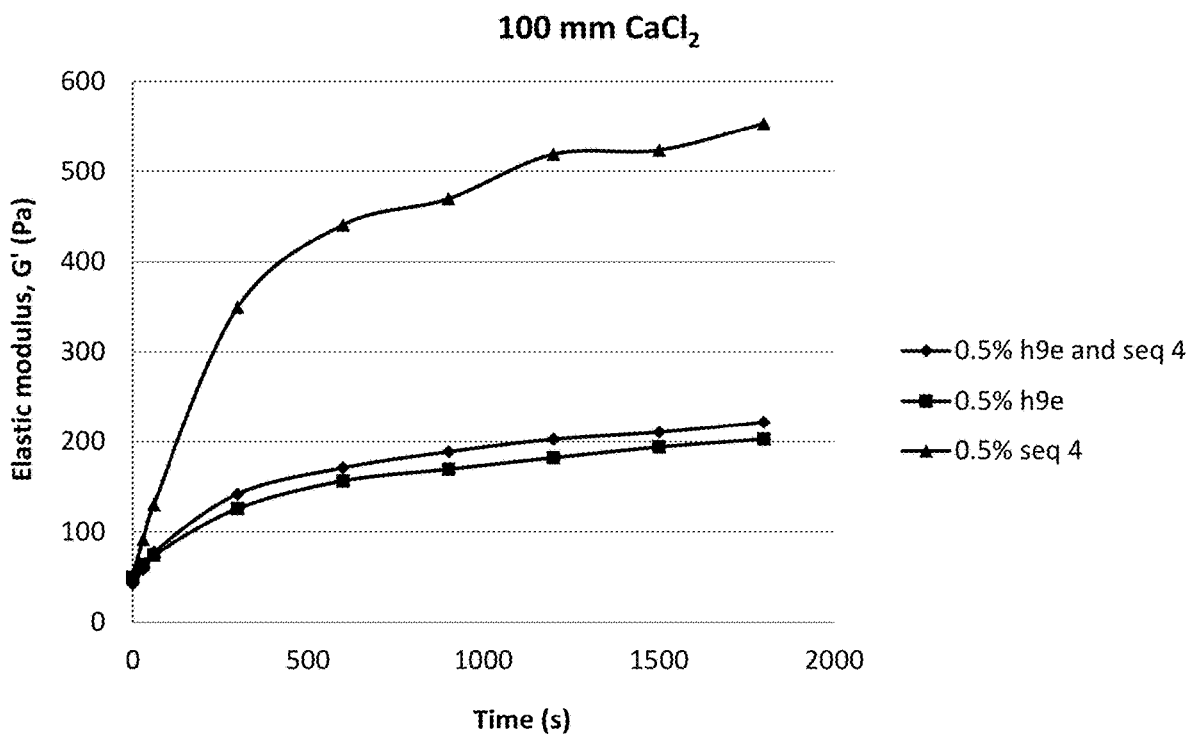
FIG. 14 shows a graph of instantaneous gelation time sweep test: Storage modulus vs time of sequence 1 and 4 alone and mixture at 1:1 ratio, triggered with 100 mM $CaCl_2$) solution.
Figure 15:
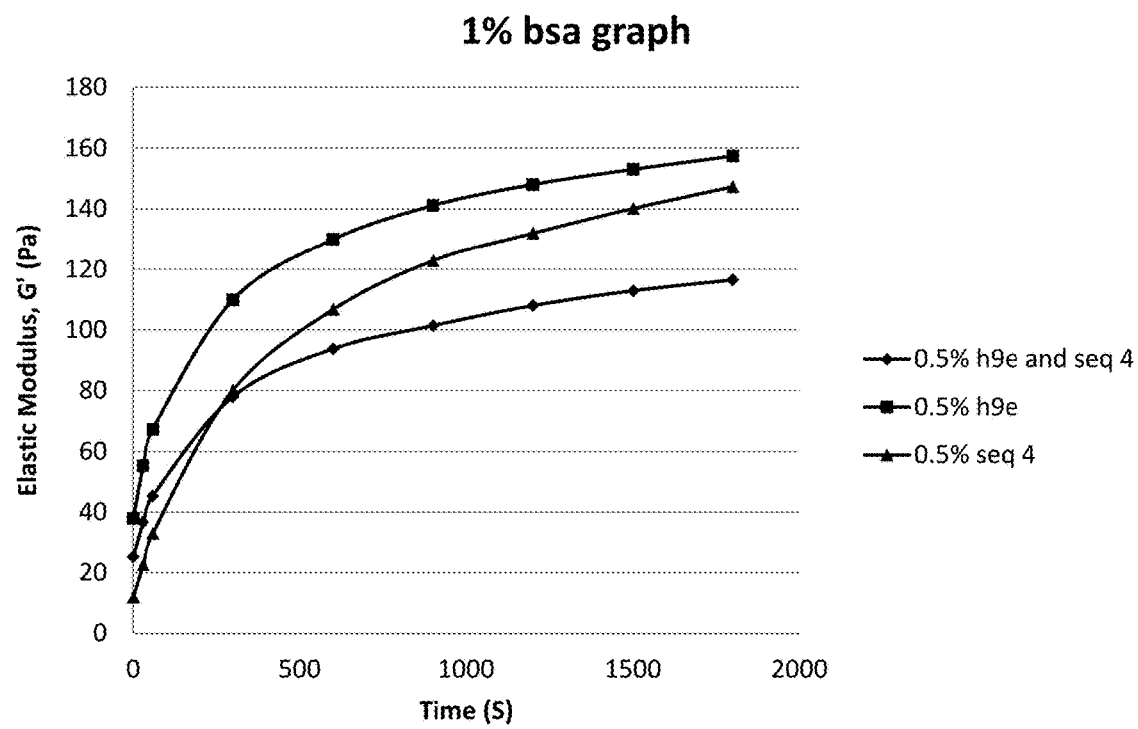
FIG. 15 shows a graph of instantaneous gelation time sweep test: Storage modulus vs time of sequence 1 and 4 alone and mixture at 1:1 ratio, triggered with 1% BSA albumin solution.
Figure 16:
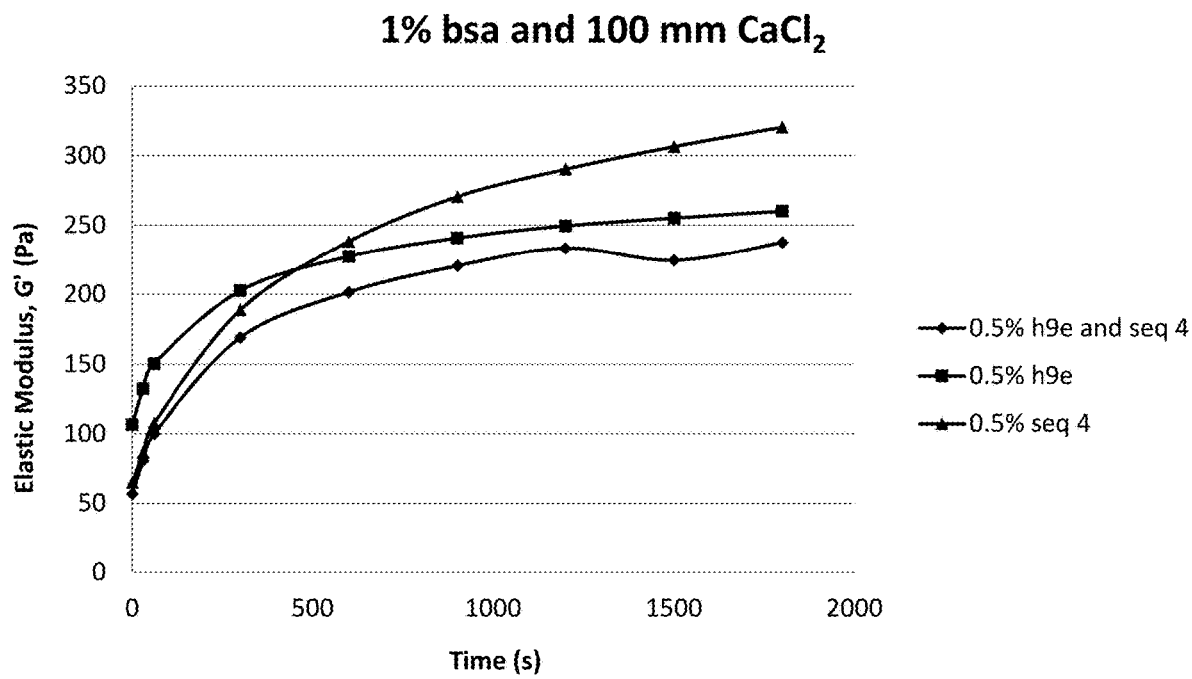
FIG. 16 shows a graph of instantaneous gelation time sweep test: Storage modulus vs time of sequence 1 and 4 alone and mixture at 1:1 ratio, co-triggered with 100 mM $CaCl_2$) solution and 1% BSA albumin solution.
Figure 17:
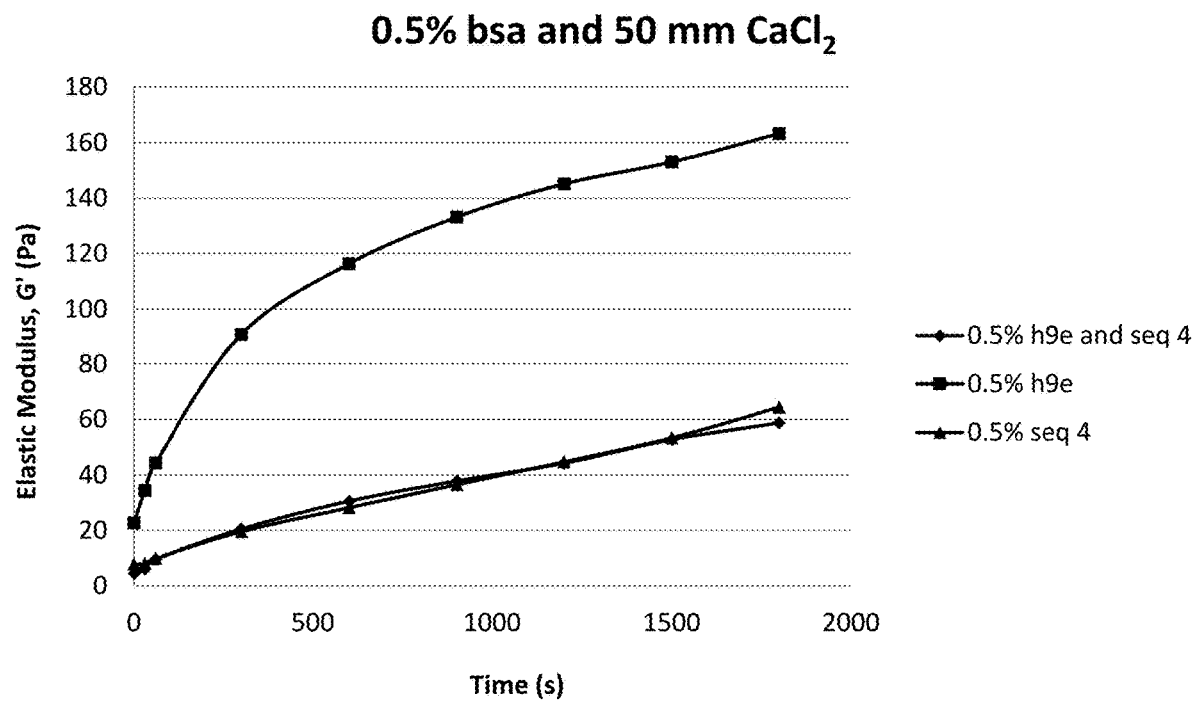
FIG. 17 shows a graph of instantaneous gelation time sweep test: Storage modulus vs time of sequence 1 and 4 alone and mixture at 1:1 ratio, co-triggered with 50 mM $CaCl_2$) solution and 0.5% BSA albumin solution.

The results are shown in FIGS. 12-17. FIG. 12 showed the gel strength of the regular h9e sequence triggered by calcium ions. Modified sequences 3 and 4 yielded a peptide hydrogel. After the 30 minute gelation time sweep, sequence 3 had a final gel strength of 196 Pa (FIG. 13), and sequence 4 had a final gel strength of 496 Pa (FIG. 13). The gel strength of sequence 3 was slightly lower than the gel strength of h9e (240 Pa) under the same conditions and sequence 4 had a final gel strength that was double the strength of h9e (FIG. 13). The data also demonstrates that a hydrogel can be developed by using one or the mixture from two or more different peptide sequences disclosed herein. FIG. 14 shows the instantaneous gelation time sweep test: Storage modulus vs time of sequence 1 and 4 alone and a mixture of the two different sequences at a 1:1 ratio, triggered with 100 mM CaCl2 solution. The mixture gel strength is closer to that of the h9e regular, and lower than the sequence 4 alone. FIG. 15 also presents the mixture use of sequence 1 and 4 triggered with 1% BSA albumin solution. In this case, the gel strength of regular h9e is the higher than sequence 4, and the mixture of 1 and 4 is the lowest in gel strength. Sequence 4 triggered with calcium had a gel strength about 550 Pa, while the gel had about 150 Pa when it was triggered with BSA. Therefore, the properties of the hydrogel can be modified depending on the initiator used to trigger gel formation, as well as by modifying the selected peptides themselves. The data also demonstrates that h9e and its derivatives can be triggered by one or more trigger agents (co-triggering systems) to obtain desirable properties. For example, FIGS. 16 and 17 present the gel strength of peptides 1 and 4 alone, and then mixed at a 1:1 ratio and co-triggered using different concentrations of CaCl2 solution and BSA albumin solution (mixture of triggers).

Example VI

ECM Ligand Built-in Hydrogels

Figure 18:
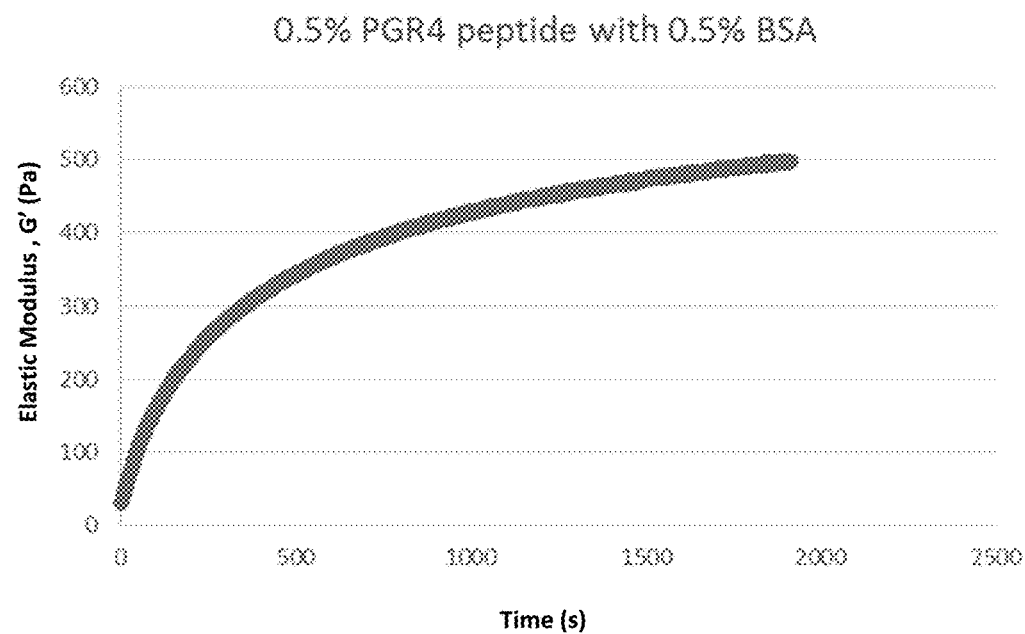
FIG. 18 shows a graph of the gelation of modified h9e hydrogel with ECM ligand RGD, for example, FLIVI-GSII-GPGGDGPGGDGRGD (SEQ ID NO:69) at 0.5% peptide solution triggered by 0.5% BSA solution.

In this Example, an ECM ligand RGD built-in peptide (i.e., FLIVI-GSII-GPGGDGPGGDGRGD (SEQ ID NO:69)) was formulated into a hydrogel at 0.5% peptide solution triggered with 0.5% BSA solution. Gelation test was performed at 37° C. for 30 min. Gel strength was about 500 Pa, similar as the regular h9e hydrogel (FIG. 18.). Peptide synthesis followed the same procedure described in Example V.

Rheology Measurements: The hydrogel samples were characterized for mechanical properties. Gelation was determined right after the peptide solution triggered using either metal ion (i.e., Ca++) or albumin proteins (i.e., BSA) using C-VOR 150 rheometer system at both room temperature and 37° C. following our previous procedure. The maximum gel strength after 24 hours was used as the gel strength. The hydrogel samples after 24 hours was used and loaded in the probe system, and examined at a single frequency (1 Hz) and steady shear strain (1%). For shear-thinning experiments, the samples were subjected to shear and then observe the strain of the storage (G') and loss (G") modulus as a function of time following our previous procedures.

Example VII

Peptide Hydrogel Blends with ECM Ligands and Functional Biopolymers

Figure 19:
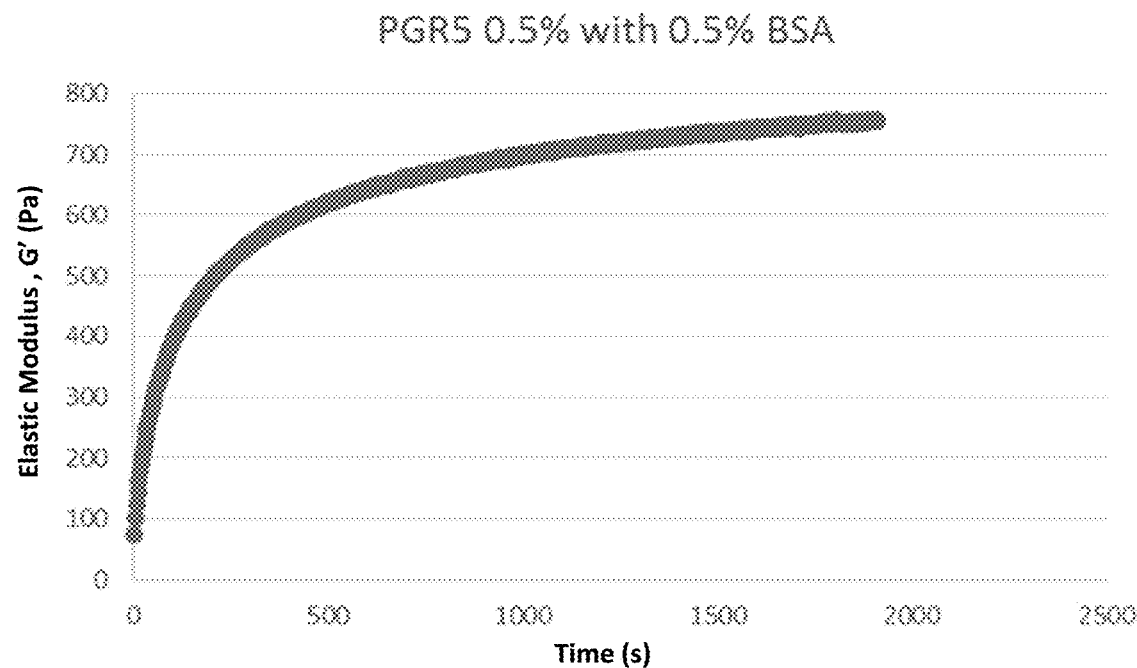
FIG. 19 shows a graph of the gelation of 1% h9e hydrogel blended with 0.1% ECM ligand GRGD (SEQ ID NO:70) triggered by 0.5% BSA solution at 37° C.
Figure 20:
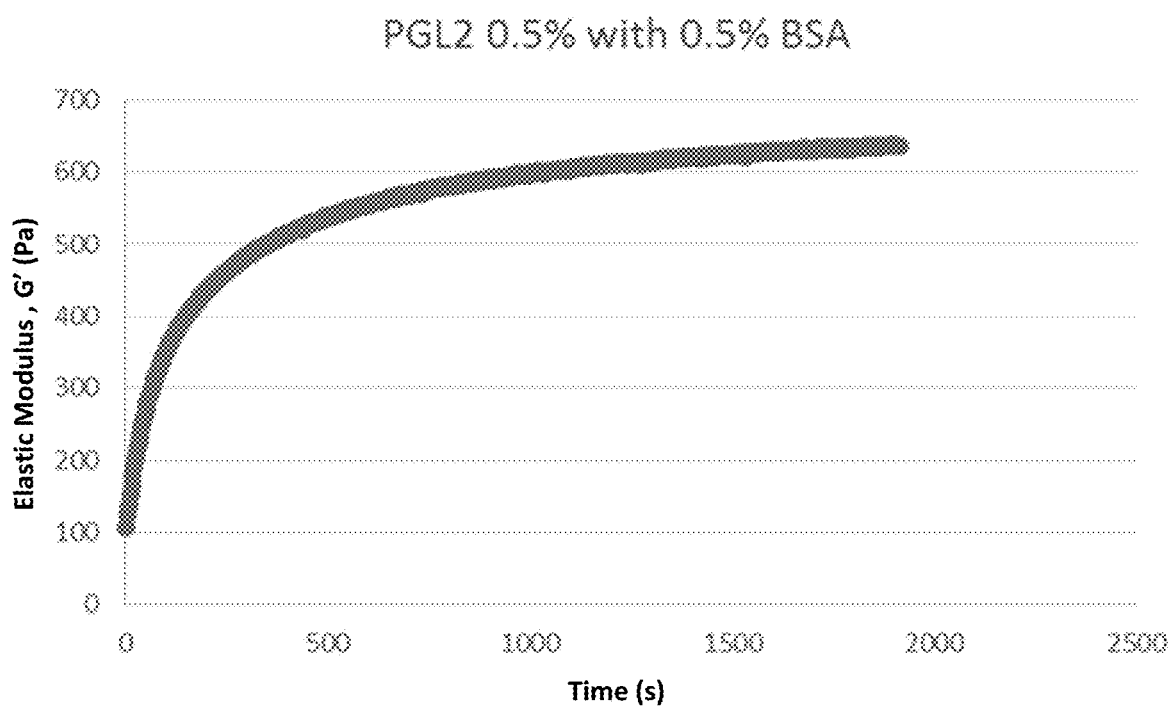
FIG. 20 shows a graph of the gelation of 1% h9e hydrogel blended with 0.1% laminin pentapetite (YIGSR(SEQ ID NO:74)) triggered by 0.5% BSA solution at 37° C.

Regular h9e peptide described in Example VI can be blended with ECM ligands and functional proteins. In this example, ECM ligands (i.e., GRGD (SEQ ID NO:70) and RGDS (SEQ ID NO:71)) at 0.1% loading level and laminin proteins (i.e., YIGSR (SEQ ID NO:74), and a1 epitope (IKVAV (SEQ ID NO:75)) at 0.1% loading level were blended with 1% h9e peptides solution. Gelation of the blend samples were triggered with 0.5% BSA solution. Gelation test was performed at 37° C. for 30 min. Gel strength was 760 Pa for the 0.1% GRGD (SEQ ID NO:71) (FIG. 19), and 640 Pa for the 0.1% laminin pentapeptide (FIG. 20). Peptide synthesis followed the same procedure described in Example V. Rheology properties were determined following the methods described in Example VI.

Example VIII

Diffusion of Small Molecules, Compounds, Drugs, Growth Factors, Nutrients

Hydrogel preparation: Hydrogel matrix at a concentration of 2 wt % h9e peptide (SEQ ID NO:1) was used. For hydrogelation, h9e solution was added into 100 mM sodium bicarbonate solution or DMEM (Sigma Chemical, St. Louis, Mo.) containing 5% of BSA solution or DMEM containing 10% newborn calf serum (FBS). The hydrogel formed within 15 min at room temperature with a final peptide concentration of either 0.25, 0.5, or 1 wt %.

Camptothecin diffusion test: Drug diffusion was accomplished by measuring drug release from the gel to the outer solution. Camptothecin was dissolved in dimethyl sulfoxide (DMSO) to prepare 50 mM of stock solution, and aliquots of the drug stock solution were added to the hydrogel-forming solution to make a final concentration of 2.5 mM for camptothecin and 5% (v/v) for DMSO. 0-mM camptothecin samples were prepared using DMSO without camptothecin. A Float-a-Lyzer (1000 KD MWCO, 1-mL capacity, regenerated cellulose membrane) was purchased from Spectrum Labs (Rancho Dominguez, Calif.). The 1000 KD MWCO membrane selected as the MWCO is sufficiently large to allow passage of h9e peptide and camptothecin. 1 mL of 0.25, 0.5, and 1 wt % hydrogel containing 2.5 mM camptothecin in 100 mM sodium bicarbonate was introduced into the inner tube of the dialyzer, which was then placed into a 500-mL glass cylinder containing 300 ml phosphate-buffered saline (PBS) as release media (outer solution). The outer solution was continually stirred at 130 rpm using a small magnetic stir bar to prevent the formation of an unstirred water layer at the membrane/outer solution interface. The drug diffusion to the outer solution at 23, 30, and 37° C. was assessed by sampling the contents of the outer solution at periodic intervals. At certain time intervals, 1 ml of solution was taken from each release system (i.e., the outer solution) for UV absorbance measurements, and the same volume of a PBS buffer, which was previously kept at the same temperature as the individual release system, was added to maintain a constant volume of outer solution.

UV absorbance measurements were carried out on a UV-1650PC spectrophotometer (Shimadzu, Kyoto, Japan). The absorbance peak at 370 nm was recorded for all measured solutions.

Cell culture and drug efficacy/diffusion tests: HeLa cells were grown in the hydrogel in 3D. Aliquots of HeLa cells solution were added into h9e hydrogel with DMEM containing 10% FBS with a final peptide concentration of 0, 0.25, 0.5 and 1 wt %. 100 µl of cell mixture solution ($3 \times 10^4$ cells per well) was seeded into a 96-well culture plate (Becton Dickinson Labware, Franklin Lakes, N.J.) and placed in an incubator (Nuair, Playmouth, Minn.) in a humidified 5% $CO_2$ atmosphere at 37° C. for about 30 min. After complete hydrogelation, 10 µl of DMEM containing 0, 50 uM, 100 uM, or 200 uM camptothecin was added on top of the hydrogel to obtain camptothecin concentrations of 0 µM, 3.125 µM, 6.25 µM, and 12.5 µM, respectively, upon total diffusion in the hydrogel. Then, 50 ul of DMEM was carefully added to the top of the hydrogel to prevent drying during long-term incubation. All measurements were made at least in triplicate, and the plates were incubated for 3 days.

A CCK-8 assay was used to determine cell viability after each treatment. 10 µL of CCK solution was added to each well. After 4 h of incubation, the absorbance at 450 nm was collected on a microplate reader (mQuant, Bio-Tek) and corrected by subtracting the background signal from a wall containing only 160 ul DMEM containing 10% FBS. Absorption intensities were averaged from 3 replicates for each sample and normalized by cells seeded in cell culture solution containing no hydrogels and camptothecin (negative control) to obtain cell viability.

Figure 21:
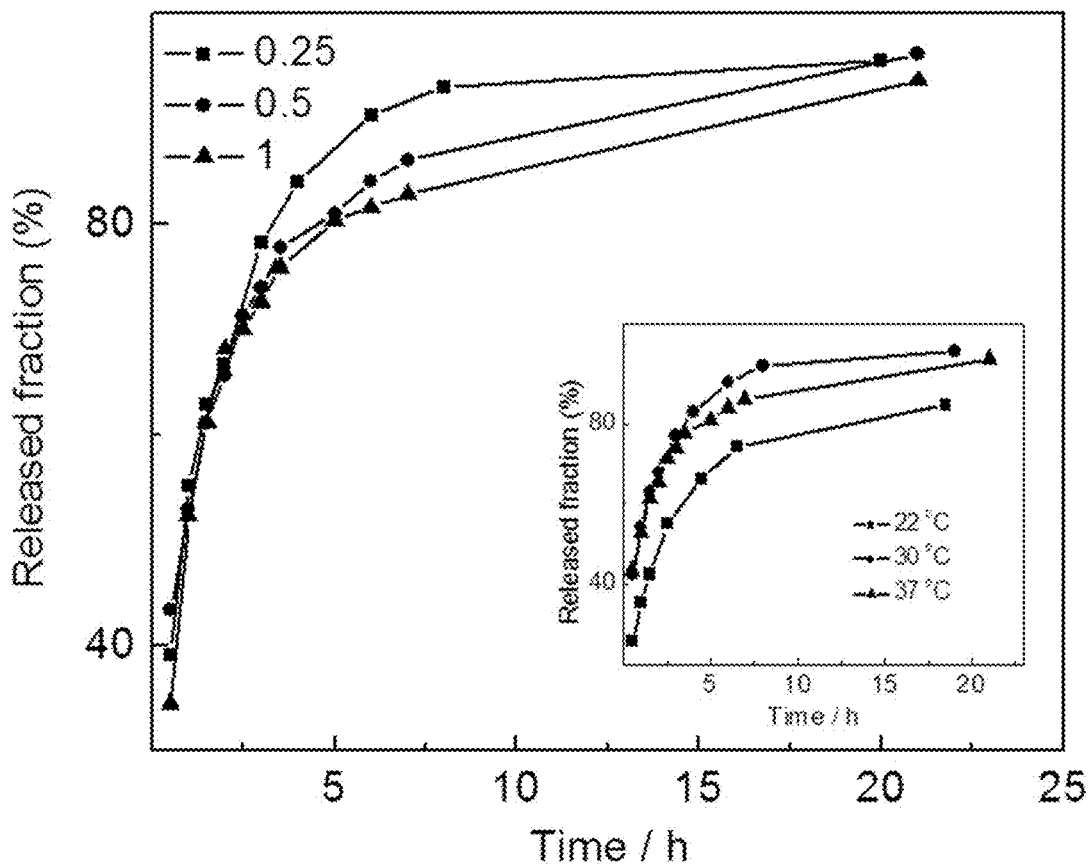
FIG. 21 shows a graph of the fraction release of camptothecin as a function of time from different concentrations of h9e hydrogel at 37° C., where the inset graph shows the fraction release of camptothecin from 0.5 wt % h9e hydrogel at different temperatures.

Results: Fluorescence spectroscopy was used to study the microenvironment changes of camptothecin in PGmatrix hydrogel. The fluorescence shows a negligible shift when PGmatrix was introduced into the system, which means the interaction between camptothecin and PGmatrix fibers is minor. Camptothecin diffusion from h9e hydrogel concentration 0.5% was performed at 22, 30, and 27° C. (inset, FIG. 21). The diffusion rate was in the order of 30° C.>37° C.>22° C. The mole diffusion rate is mainly determined by the matrix mobility, which is enhanced by temperature and peptide fiber concentration.

Figure 22:
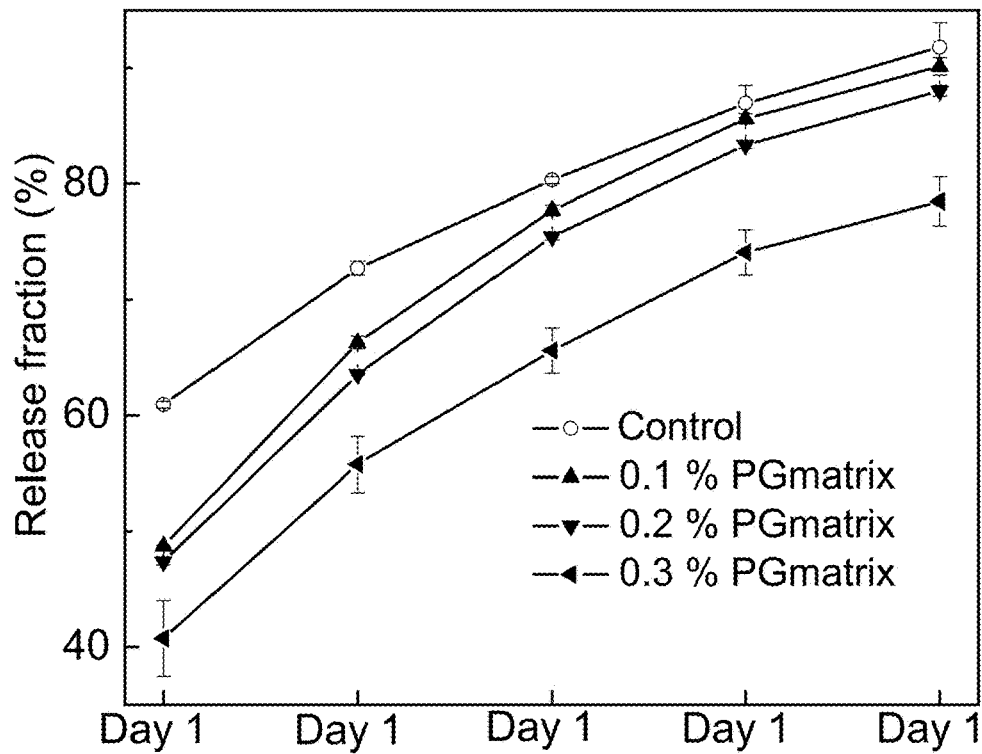
FIG. 22 shows a graph of the fraction release of cisplatin in peptide-albumin hydrogel as a function of time from 0, 0.1, 0.2, and 0.3 wt % PG matrix hydrogel at 37° C.

Hela cancer cell viability was used to evaluate drug diffusion effectiveness. After a 3-day treatment with various concentrations of camptothecin, we found a dose-dependent decrease in cell viability in camptothecin. Although different concentrations of the h9e hydrogel were treated with the same amount of camptothecin, cell viability was comparable, which implies the hydrogel also has sustained release effects of camptothecin on killing HeLa cells. This result was in accordance with our fluorescence measurement and diffusion results, which demonstrated that h9e hydrogel also perform as sustained release agent of camptothecin. The diffusion of Cisplatin cancer drug in hydrogel was also studied, and diffusion rate was presented in FIG. 22.

Example IX

Oxygen Transfer Rate of Peptide Hydrogel

Hydrogel: 1% h9e peptide was prepared in sodium bicarbonate solution, and 1% BSA was prepared in PBS solution as trigger solution. The h9e peptide solution and BSA solution was mixed at 1:1 volume ratio, and incubated at 37 C for 30 min to prepare hydrogel with 0.5% h9e peptide concentration and 0.5% BSA with a gel strength of about 450 Pa.

Oxygen transmission rate (OTR): The OTR of hydrogels is another important property for in vitro tissue and organ regeneration process. Standard PGmatrix hydrogels was used in this experiment. OTR is the steady state rate at which oxygen gas permeates through a material at specified conditions of temperature and relative humidity. Values are expressed in cc/m2/24 hr in metric units determined by MOCON, Inc. (Minneapolis, Mo.) for OTR measurement using OX-TRAN instrument according to the standard method. Both challenge gas (oxygen) and sweeper gas (nitrogen) was held at relatively humidity of 100% to avoid gel drying, and temperature will be kept at ambient. 3.75 ml hydrogel was used and spread into thin film to cover the 5 cm$^2$-area. Experiments were duplicated twice.

Results: OTR of the hydrogel was reported to be 3,984 cc/m$^2$-day. High density polyethylene (HDPE) has OTR ranging from 2300 to 3100 cc/m$^2$-day, and oriented polystyrene (OPS) has OTR ranging from 4350 to 6200 cc/m$^2$-day. Materials with OTR of 1500 to 3000 cc/m$^2$-day are considered as low oxygen transfer materials, and OTR of 3000 to 8000 cc/m$^2$-day as medium oxygen transfer materials.

Example X

Stem Cell 3D Culture in Hydrogel

Rat PSCs: Animal use was approved by the KSU Institutional Animal Care and Use Committee (protocol #3168). Rat ESCs were derived in-house from Dark Agouti rats (line 52) and characterized following the methods described in previous studies. Low passage ESCs were thawed, expanded one passage in 2D on MEF feeders, and then used in these experiments. Rat iPSCs were generated from Fischer 344 rat embryonic fibroblasts using a mouse OKSM STEMCCA lentiviral reprogramming vector according to the manufacturer's protocol (Millipore, SCR513).

2D cell culture: Rat ESCs and iPSCs were cultured in N2-B27 media with 2i inhibitors on MEFs as previously described.

3D cell culture: We adapted the techniques used previously to encapsulate breast cancer cells in 3D described in previous studies. This was done by using the regular h9e peptide hydrogel (1% wt=6 mM) in an aqueous solution. The peptide hydrogel-medium was prepared by directly mixing the aqueous h9e peptide solution with concentrated 2i plus LIF medium at 1:1 ratios for a final peptide concentration of 3 mM (600 Pa). This required that the 2i plus LIF base medium be made up at higher concentration such that after mixing with h9e solution, it resulted in a 1× concentration of medium components. Specifically, medium was made at 1.2× concentration for the 1:5 dilution, 1.33× for the 1:2 dilution and 2× for the 1:1 dilution in the three h9e hydrogel concentrations. After mixing, the cells were added and the mixture was immediately added to the dish slowly to avoid air bubbles. The plates were then incubated for 30 min at 37° C. to permit gelation. To feed, 1× concentration 2i plus LIF medium was added slowly to the top of the hydrogel. To pass, the media was pipetted up and down by adding 1-2 ml of PBS more forcefully to shear the gel, and the liquefied contents were then added to a tube and diluted to a concentration that was below that which permitted gelation. The colonies were pelleted by low speed centrifugation (100×g for 5 min at room temperature), washed with calcium and magnesium free PBS, and then trypsinized to single cells by addition of trypsin EDTA for 5 min. Enzymatic reaction was terminated by dilution with PBS and 2 washing steps. The PSCs were suspended in a small volume of medium, added to the 1× hydrogel-medium solution, and re-plated at the desired concentration. Alkaline phosphatase staining, Immunofluorescence staining: Karyotyping, Embryoid body formation, Gene expression analysis were performed to determine the differentiation properties.

Figure 23:
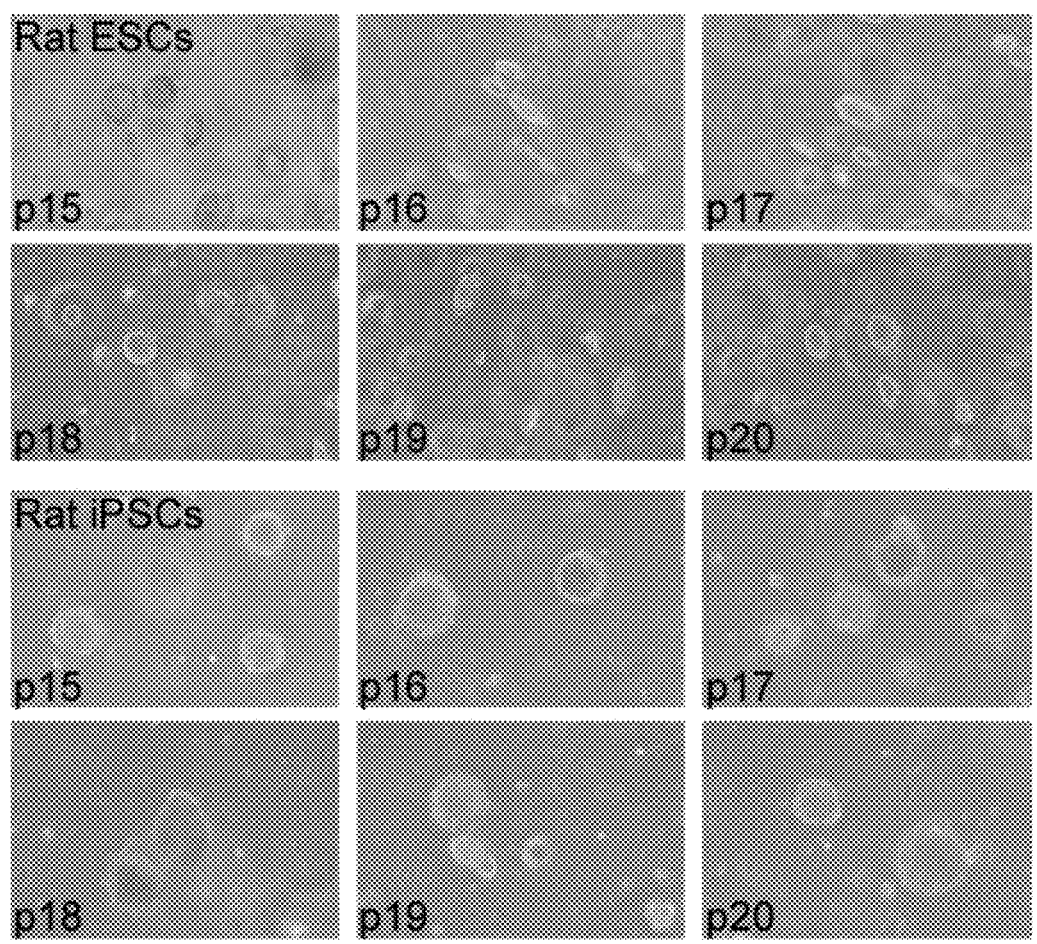
FIG. 23 shows phase contrast images of DA 52 Rat ESCs and iPSCs in 0.5% h9e hydrogel matrix for 20 passages.

Results: Colony morphology in 3D culture: rat pluripotent stem cells encapsulated within the 3 mM hydrogel proliferated well. The rat ESC and iPSC colonies became visible as small colonies usually two days after plating (FIG. 23). There were no obvious differences between the rat ESC and rat iPSC colonies in terms of morphology in culture, when observed in phase contrast. When starting from dissociated single cells, the colonies in a particular passage were generally of a consistent size. The colonies maintained the appearance of undifferentiated morphology as compact, smooth, highly refractile spherical colonies or ovoid colonies. The colonies increased in size (grew) over time in culture and usually became ready for passage by day 4-5. Spontaneous differentiation on the colony edges was never observed in rat ESC or rat iPSC cultures. Following immunocytochemical staining, the rat ESC and iPSC colonies appeared to be hollow.

Alkaline phosphatase staining results showed consistent AP staining in rat ESC and iPSC colonies following expansion and passage in 3D within the hydrogel. AP staining was not affected by more than 25 passages in 3D culture. Immunocytochemical staining (Oct4, Nanog, Sox2, and for the pluripotency marker SSEA-1) suggested that the rat ESCs and iPSCs were maintained in the undifferentiated state since the staining was consistent after at least 25 serial passages, and as many as 30 serial passages in 3D culture.

Example XI

Immune Response Properties of Peptide Hydrogel

Hydrogel: 1% h9e peptide was prepared in sodium bicarbonate solution, and 1% BSA was prepared in PBS solution as trigger solution. The h9e peptide solution and BSA solution was mixed at 1:1 volume ratio, and incubated at 37° C. for 30 min to prepare hydrogel with 0.5% h9e peptide concentration and 0.5% BSA with a gel strength of about 450 Pa.

Experiment: In trials #1 and #2, healthy female mice of FVB 6-15 week old were injected subcutaneously in the inguinal region with 100 or 200 uL of the hydrogel or control solutions in a blinded study. Weight and external body temperature were measured daily for up to 2 weeks.

Mammary fat pads from the inguinal region were removed at necropsy. Tissues were fixed with 10% formalin and processing for a 5 um thickness sectioning. Samples were stained with hematoxylin and eosin (H&E). Hydrogel trial 3 was completed in the same manner described above with the following exceptions. 200 uL of hydrogel or control solutions were injected subcutaneously on the back of the animal. No tissues were removed at necropsy due to a complete absorption of hydrogel.

Microscope slide preparation: Samples of the control, and hydrogel treated tissues were submitted for histopath processing at Diagnostic Laboratory at KSU Veterinary School in Mosier Hall. Slides and paraffin blocks were labeled 1 as control and 4 as hydrogel treated, respectively. Adipose tissue samples were processed on the Sakua Tissue-Tek VIP 6, model #VIP6-A1. Then, the samples were then embedded using the Sakura Tissue-Tek Tissue Embedding Console System model #4710. For microscope slide preparation, the paraffin blocks were cut on a 1215 Leitz Rotary Microtome and sectioned at 5 microns. Sections were then mounted on a microscope slide from a water bath. H&E staining of the slides done on an automated stainer, Leica Autostainer XL, model #ST5060. Lastly, the stained slides are covered slipped by an automatic coverslippper, Leica CV5030.

Microscopes: 1000× images and 40× images of samples were visualized by Nikon Eclipse 80i with 100× and 4× objective lenses, respectively, and analyzed with NIS Elements computer program. 1000× images were taken 10/1/14, and 40× images on 10/23/14 with white balance effect applied.

Inflammatory analysis: The fixed tissues of animals without treatment, treated with PBS buffer and h9e hydrogel were further analyzed for inflammatory effects including VWF8 (blood vessel), Arginase I (wound healing macrophage), Fsp1 and α-smooth muscle actin (fibroblast), CCL2 (pro-inflammatory cytokine), and TGF-beta (immunosuppressive cytokine). 796 (FVB normal mammary gland) was used as negative control. Image J arbitrary unit was used to evaluate these tests using Image J software.

Results: The hydrogel treated animals had the same normal daily activity as those controls. Body temperature and body weight of all treated and control animals were fluctuated in the expected ranges. The histological images indicating that no significant difference was observed between the hydrogel treated and control samples. H&E staining showed up under microscope as purple and denotes proteins on membrane of the cells (e.g. collagen) and as a result gives outline of adipose cells and is concentrated along lining of blood vessels in tissue. No significant inflammatory effects were observed compared to controls (Table 3).

TABLE 3

Inflammatory analysis (image J arbitrary unit) of fixed tissues isolated from the mice: 1F = without treatment, 2F = treated with PBS buffer, 7F = treated with 0.5% h9e hydrogel triggered with 0.5% BSA solution.

|  | 1F | 2F | 7F | 796 FVB normal mammary gland |
|---|---|---|---|---|
| VWF8 | 0.015 | 0.020 | 0.030 | 0.050 |
| Arginase I | 0.027 | 0.02 | 0.008 | 0.034 |
| Fsp1 | 0.042 | 0.015 | 0.014 | 0.036 |
| α-smt | 0.038 | 0.042 | 0.026 | 0.020 |
| CCL2 | 0.038 | 0.028 | 0.025 | 0.024 |
| TGF-beta | 0.050 | 0.030 | 0.022 | 0.020 |

Example XII

Wistar Rat Red Blood Cell Viability in h9e Hydrogel

The goal of this experiment was to determine viability and morphology of red blood cells from seeding in prepared hydrogel at 3 different final h9e peptide concentrations (0.5%, 1%, and 2%) and also to determine gelation of these prepared gels all monitored over 10 days (evaluated on days 0, 1, 3, 7, and 10.

Materials and Methods

1. Preparation of Hydrogel Samples with Red Blood Cells (RBCs)

Hydrogel solutions were prepared for 0.5% h9e gel, 1% h9e gel, 2% h9e gel (w/v), each having a final volume of 3 mL, a final concentration of 1% BSA (w/v), and 10% of RBC sample (v/v). The recipe for each solution is provided in Table 4 below.

TABLE 4

| Final product | 0.5% h9e hydrogel w/RBCs | 1% h9e hydrogel w/RBCs | 2% h9e hydrogel w/RBCs |
|---|---|---|---|
| Peptide solution | 1.5 mL of 1% h9e sol. | 1.5 mL of 2% h9e sol. | 1.5 mL of 4% h9e sol. |
| 2.5% BSA solution | 1.2 mL | 1.2 mL | 1.2 mL |
| RBC sample | 0.3 mL | 0.3 mL | 0.3 mL |
| Total volume | 3 mL | 3 mL | 3 mL |

To make the above solutions, we prepared 4 mL (0.4 mL extra) of 2.5% BSA solution, 1.5 mL of 1% h9e sol., 1.5 mL of 2% h9e sol., and 1.5 mL of 4% h9e sol. To prepare 4 mL of 2.5% BSA solution, 100 mg of BSA crystals (Sigma, Cat #A7906) was dissolved in 4 mL of PBS 1× Solution (Fisher Scientific, Cat #BP2438-4). The h9e solutions were prepared as indicated in Table 5 below.

TABLE 5

| h9e solution concentration | 1% | 2% | 4% |
|---|---|---|---|
| H9e powder (mg) [PepGel LLC] | 15 | 30 | 45 |
| 100 mM NaHCO$_3$ solution (mL) | 1.5 | 1.5 | 1.5 |
| Stirring time needed (hrs) | 2 | 4 | 5* |

H9e solutions were mixed at room temperature for their prescribed stirring time until the peptide powder was dissolved. However, the 4% h9e solution was stirred for ~10 hours and still not completely clear, and thus the 4% h9e solution was determined to be characteristically unclear. All solutions were then transferred to 8° C. to store overnight.

For all h9e solutions, magnetic stir bars were removed, and vials were covered with stoppers and clamped. H9e solutions (along with a syringe and an empty vial for filtered BSA) were placed in a large autoclaveable container sealed and autoclaved at 121° C. for 20 minutes (without drying step). The container, BSA solution, and fresh RBC sample (10 mL vial of Wistar Rat RBCs, Innovative Research Inc., Cat #IC05-3065-16114) was then transferred to a sterile hood. BSA solution was drawn into the autoclaved syringe with needle then filtered into the autoclaved vial through a 200 μm pore size syringe filter attachment. Then 1 mL of RBC sample was pipetted into filtered BSA solution and pipetted up and down slowly to form a homogenous mixture. 1.5 mL of BSA+RBC mixture was then pipetted into each vial containing h9e solutions. These were pipetted slowly up and down to create a homogenous mixture (careful not to introduce bubbles).

Hydrogel preparation and evaluation was conducted according to the following schedule: Solution Prep, Day 0, Day 1, Day 3, Day 7, and Day 10. After testing for each evaluation day, samples were returned to 8° C. for storage until next day of evaluation.

2. Microscopes, RBC Imaging, and Slide Preparation

RBC imaging was done at Nguyen Lab of Molecular Toxicology (0229 Mosier) with Nikon Eclipse 80i with DS-Fi1 camera, using CFI 10×/22 binocular lenses and 100× objective power with oil immersion. (Total 1000× magnification). NIS-Elements program was used to capture images.

On Day 0, to prepare slides, RBCs were diluted with PBS, 1:50, and pipetted vigorously to mix. Then 3 uL where used for imaging on a standard slide and glass coverslip. All subsequent days, it was found easier to image by pipetting about 5 uL of hydrogel+RBC sample directly on to slides for imaging, as the cells seemed to lyse easier in PBS preparation.

3. Viability Measurements to Assess RBC Viability in Hydrogel.

All viability measurements were taken with Cellometer Mini (Nexcelom). 10 μL of cell-containing sample was mixed with 10 μL of Trypan blue stain and incubated at RT for 2 min. and transferred to cell counting chamber (Nexcelom, Cat #CHT4-SD100-002) well for measurement. Dilution factor was set to 2.

Viability measurements on the RBC/hydrogel suspension were taken on Day 0, 1, 3, 7, and 10. Because of excessive cell crowding resulting in inability to perform test, a diluted sample was prepared with 1 μL of the RBC/hydrogel suspension with an addition of 50 μL of PBS. The diluted sample was pipetted vigorously on Day 0, 1, and 3 and mixed with syringe needle on Day 7 and 10 to better break up clustered RBCs/hydrogel for more accurate cell viability measurements. The diluted sample was then measured for cell viability. Two (2) tests were performed and the results averaged.

4. Rheometer Measurements to Assess RBC/Hydrogel Gelation

All Rheometer measurements were done with Bohlin Instruments CVOR 150 Rheometer. 200 μL of each sample was used per gelation test. Two (2) trials were done per day. The first trial for each sample of Day 0 was done for 30 min. All other trials were done for 10 min.

Sample preparation: Gel was sheared by pipetting and mixing. 200 uL was drawn and placed on rheometer stand for testing. Rheometer Settings: Oscillation test, 37° C., with Gap Size of 500. Elastic modulus was tested over time and recorded for the time points 0, 30, 60 seconds and also at 5 and 10 minutes. For Trial 1, Day 0: time points 15, 20, 25, and 30 min w also recorded)

Results

1. RBC Morphology

RBC morphology was evaluated using the images taken on Day 0, 1, 3, 7, and 10 at Nguyen Lab with Nikon Eclipse 80i at 1000×.

Figure 24:
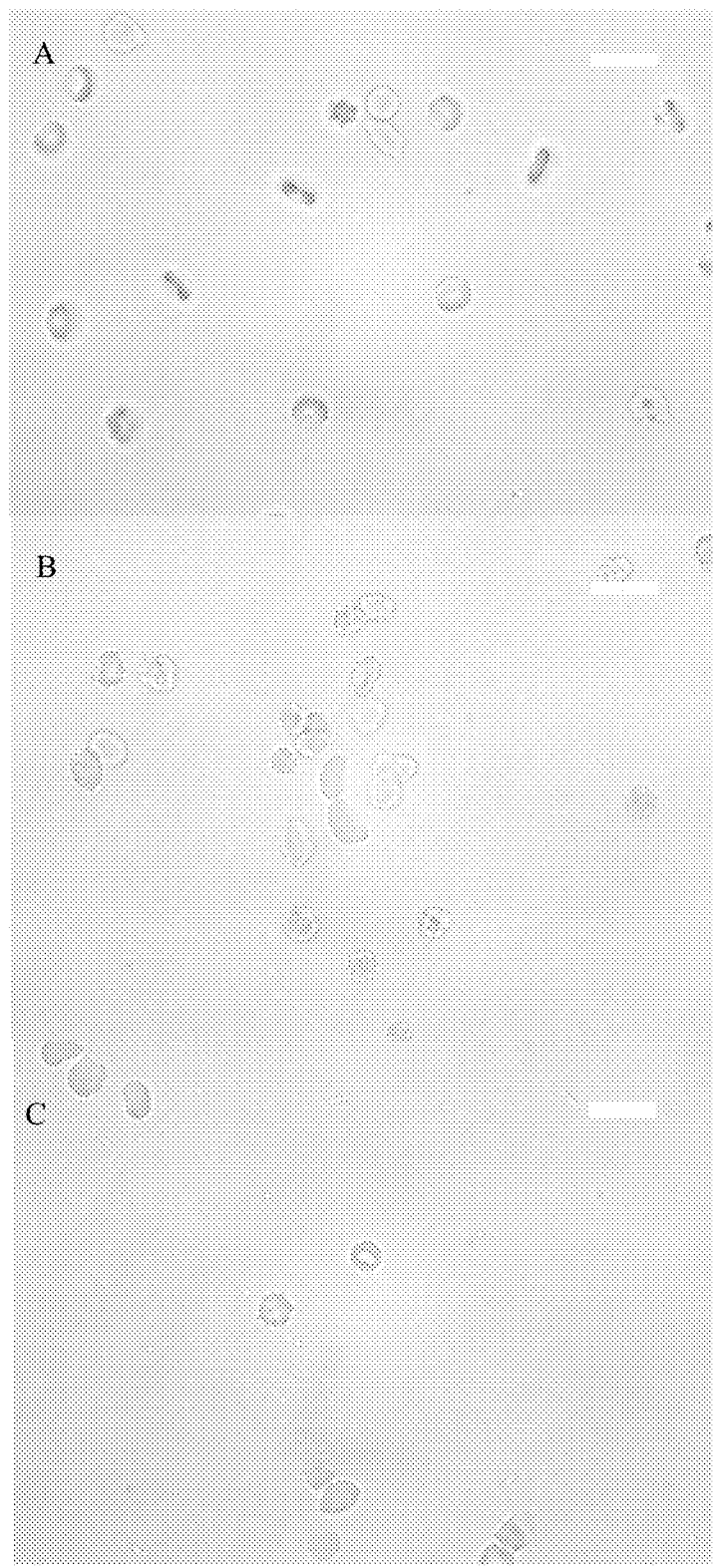
FIG. 24 are images showing RBC morphology in RBS/h9e hydrogels on Day 0 of testing. A, B, and C show hydrogels having h9e concentrations of 0.5%, 1%, and 2%, respectively.
Figure 25:
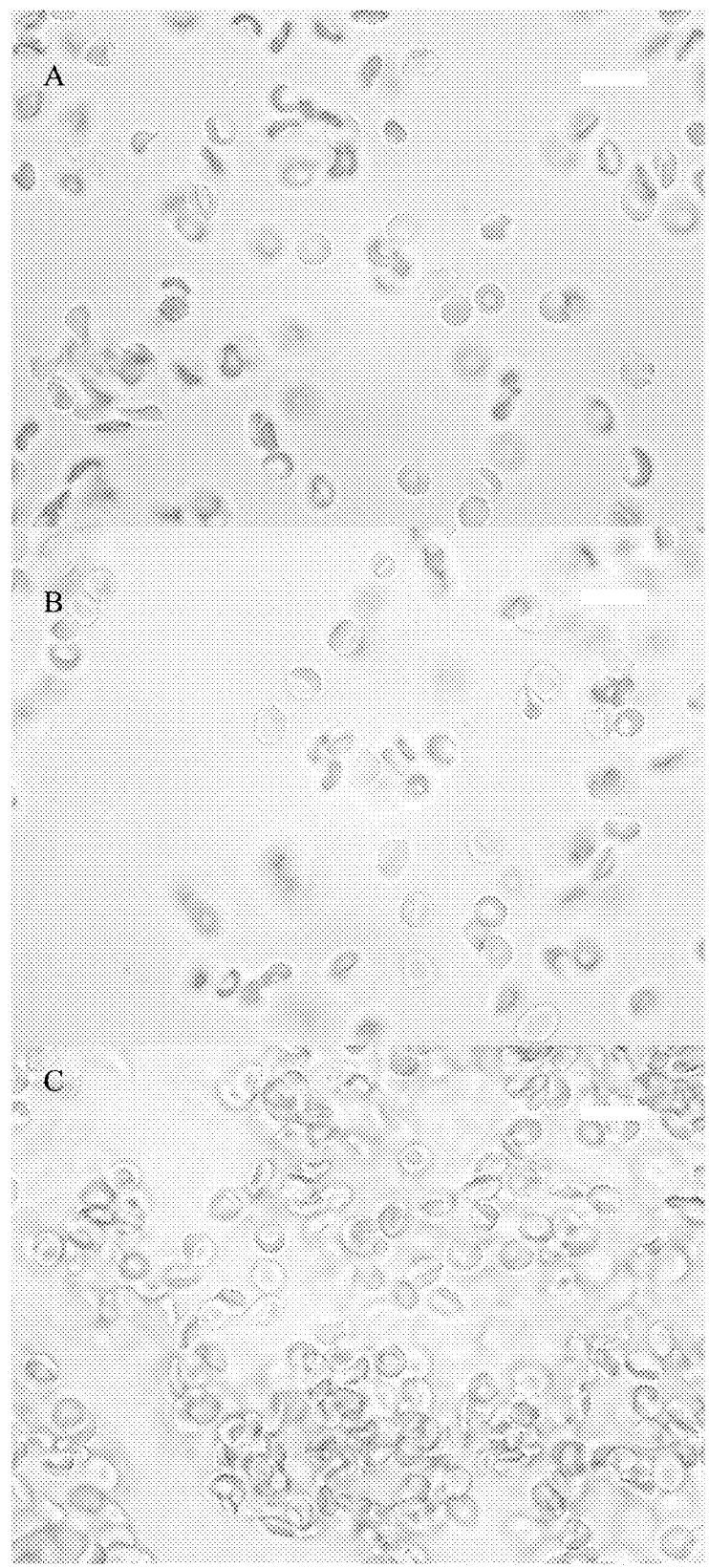
FIG. 25 are images showing RBC morphology in RBS/h9e hydrogels on Day 1 of testing. A, B, and C show hydrogels having h9e concentrations of 0.5%, 1%, and 2%, respectively.
Figure 26:
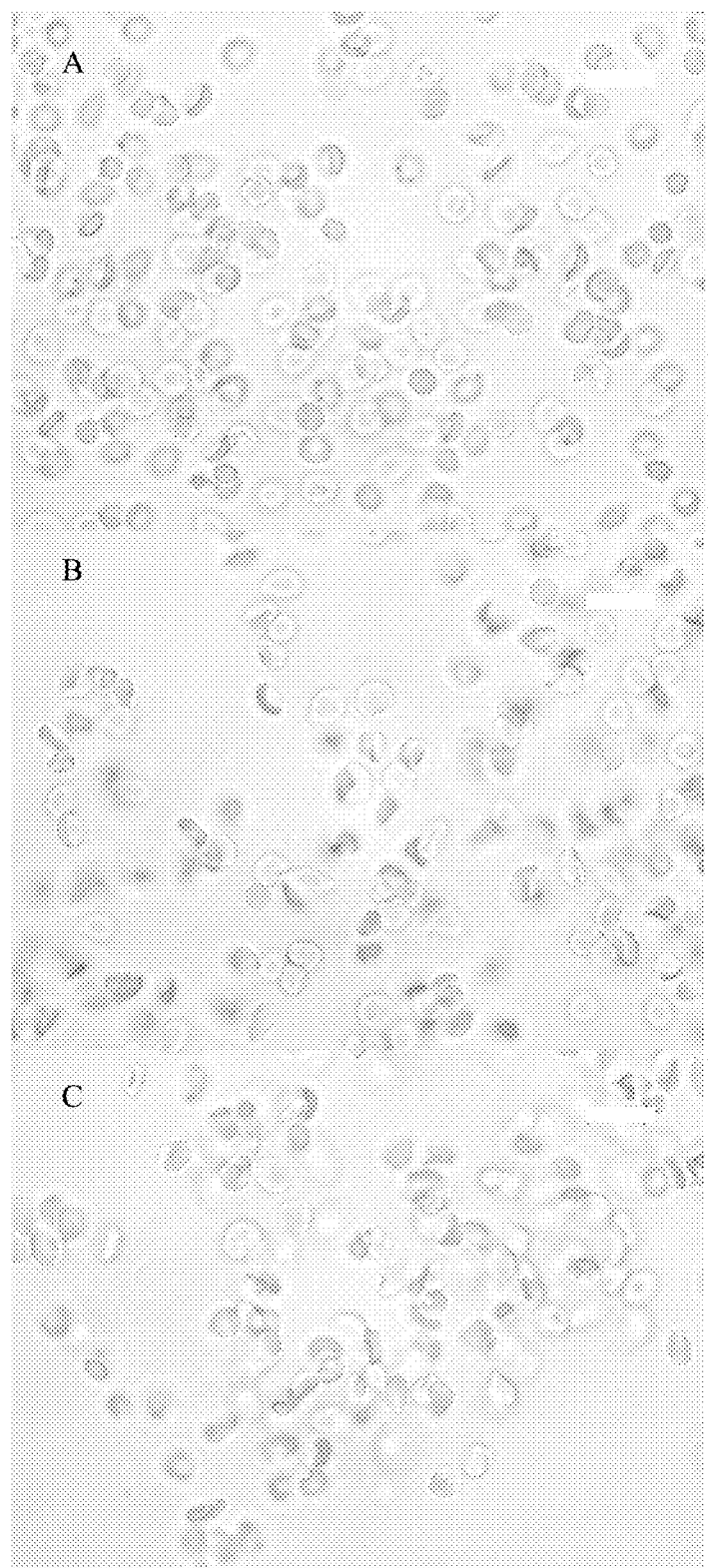
FIG. 26 are images showing RBC morphology in RBS/h9e hydrogels on Day 3 of testing. A, B, and C show hydrogels having h9e concentrations of 0.5%, 1%, and 2%, respectively.
Figure 27:
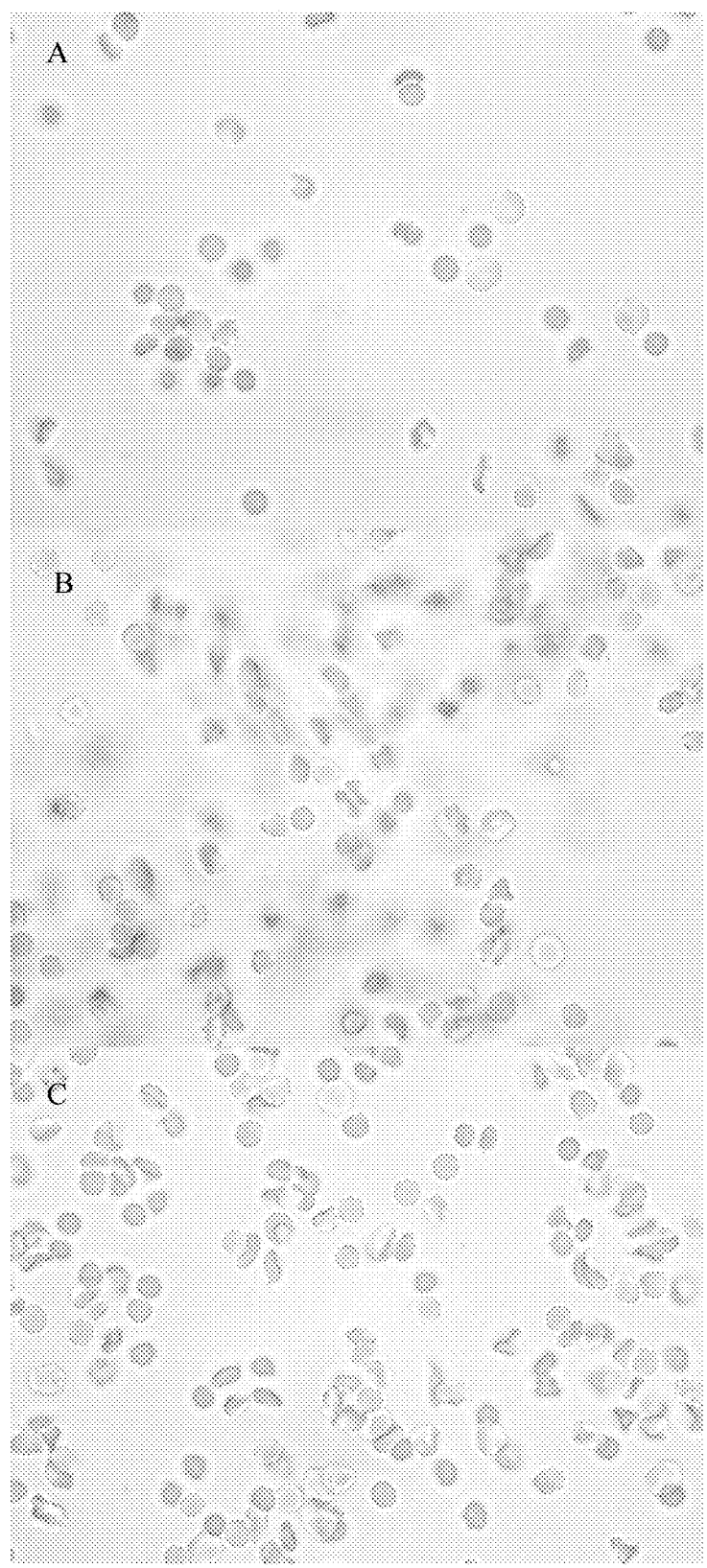
FIG. 27 are images showing RBC morphology in RBS/h9e hydrogels on Day 7 of testing. A, B, and C show hydrogels having h9e concentrations of 0.5%, 1%, and 2%, respectively.
Figure 28:
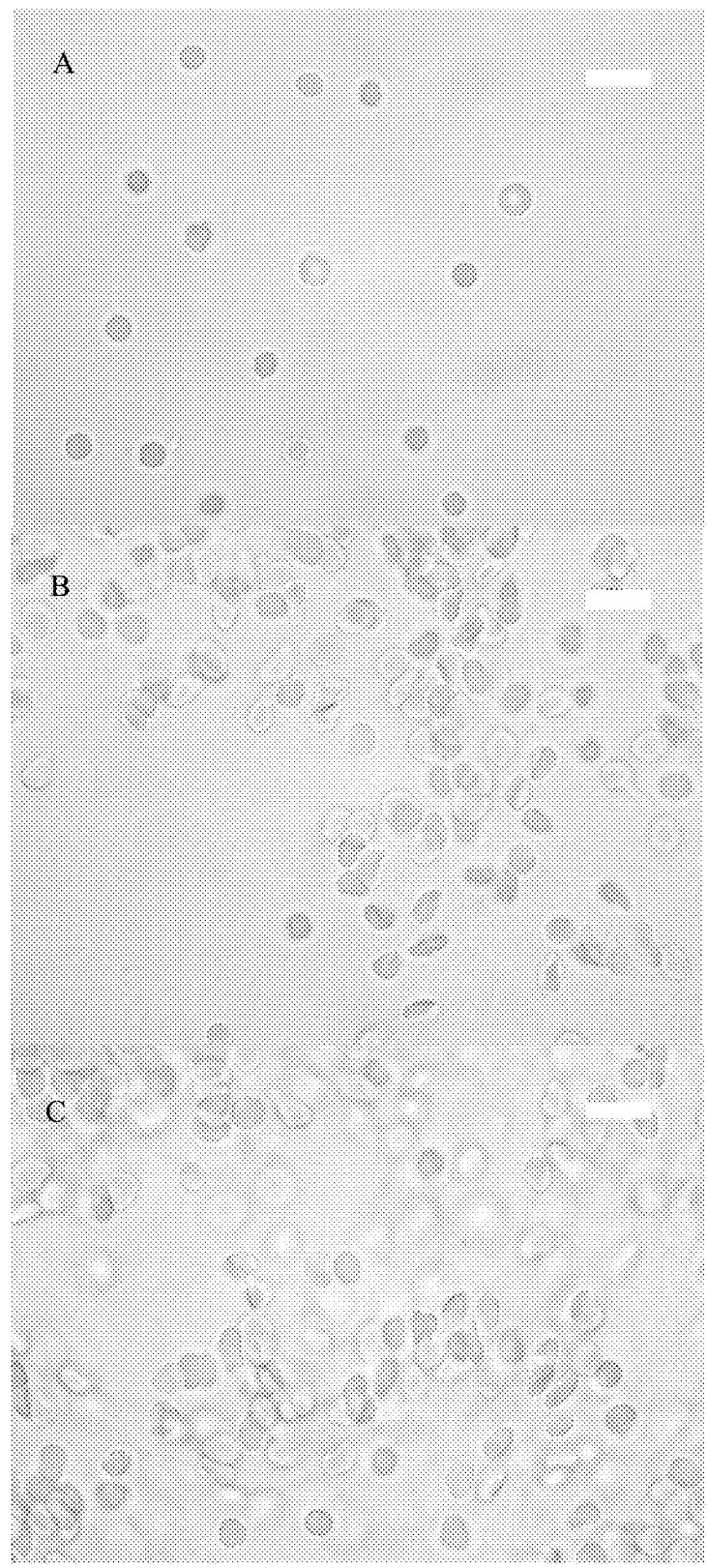
FIG. 28 are images showing RBC morphology in RBS/h9e hydrogels on Day 10 of testing. A, B, and C show hydrogels having h9e concentrations of 0.5%, 1%, and 2%, respectively.

As shown in FIG. 24, on Day 0 RBC/hydrogels were diluted with PBS 1:50 uL and visualized at 1000×. RBCs seemed to be present (round cells—donut shaped), and some white blood cells ('spiky' appearance) were also present in the sample. There were healthy RBCs found in the samples, but the 1% h9e gel cells seemed to be misshapen or lysed. This was most likely because of PBS dilution preparation, which required vigorous pipetting. On Day 1 healthy RBCs were seen in all RBC/hydrogels (FIG. 25). On Day 3 healthy RBCs were seen in the RBC/hydrogels, with the most found in the 0.5% h9e hydrogel, less in the 1% h9e hydrogel, and the least in the 2% h9e hydrogel (FIG. 26). On Day 7, donut shaped RBCs were harder to spot in samples compared to previous days of evaluation, with the most found in the 0.5% h9e hydrogel, less in the 1% h9e hydrogel, and the least in the 2% h9e hydrogel (FIG. 27). On Day 10, donut shaped RBCs were harder to spot in samples compared to previous days of evaluation, with the most found in the 0.5% h9e hydrogel, less in the 1% h9e hydrogel, and the least and virtually none in the 2% h9e hydrogel (FIG. 28).

The morphology change of the RBCs is predicted to be due to the loss of moisture or the increase of viscosity of the hydrogels over the days due to handling and exposure to air during sample preparation for testing. The slide preparation procedure can also smash cells and cause them to lose the donut shape appearance. When there are loose RBCs floating in channels formed between stationary cells, they preserve donut shape. However, when the RBCs settle on the microscope slide, the pressure of the coverslip and glass slide cause them to become flat. Moreover, the pressure of the objective lens pushes down on the coverslip (oil immersion technique). As gels lose moisture and increase in thickness, this 'smashing' phenomena increases on the slide, and it is more difficult to find donut shaped cells.

Fresh RBCs were diluted with PBS, 1:10 v/v, on Day 0 and preserved for testing throughout 10 days. This sample was used to compare to the hydrogel images on Day 0 and 10. However, the microscopic images based on this sample showed only white blood cells. This is most likely because the red blood cells were lysed in the PBS solution or because the RBC sample extracted on Day 0 comprised primarily white blood cells. Additionally, PBS dilution of the fresh RBC sample on Day 3 produced images with mostly WBCs and deformed RBCs. The PBS seemed to be lysing RBCs and leaving WBCs, and therefore centrifugation may be necessary for extraction of RBCs from whole fresh RBC samples in the future.

2. Viability Measurements

Viability measurements showed similar results for fresh RBCs and RBCs in RBC/hydrogel suspension. Viability measurements on diluted RBC/hydrogel samples were taken on Day 0, 1, 3, 7, and 10. Fresh RBCs were diluted with PBS, 1:10 v/v, on Day 0 and preserved for testing throughout 10 days. Fresh RBC was prepared by taking 1 uL of fresh RBC and diluting 1 mL of PBS on the day of evaluation. Two test trials on the same dilution sample (see Materials and Methods section 3) yielded the results displayed in Table 6 as an average.

TABLE 6

| Viability (% Live cells) | 0.5% h9e gel | 1% h9e gel | 2% h9e gel | RBCs in PBS | Fresh RBCs |
|---|---|---|---|---|---|
| Day 0 | 35.7 | 33.2 | 32.4 | 54.3 | — |
| Day 1 | 39.5 | 39.8 | 42.6 | 45.5 | — |
| Day 3 | 52.4 | 36.4 | 37.5 | 70.5 | 40.6 |
| Day 7 | 35.1 | 34.1 | 35.1 | 58 | 37.3 |
| Day 10 | 36.4 | 38.3 | 39.3 | 62.2 | — |

Table 6 illustrates the difficulty in producing accurate viability measurements. Images from Cellometer Mini for each test showed that the machine was not counting live cells properly. For example, half of the well was not in the same plane as the other half, which accounted for results mostly under 50% viability due to the inability to focus on all the cells at once during counting. This resulted in varying viability with no correlation over the days and among the samples. Also, the more viscous samples (higher concentration of h9e) had cell clumping problems that prevented accurate counting. This may also explain why RBCs in PBS exhibited high viability, as the individual cells were countable. Also, changing to mixing by syringe and needle on Day 3 seemed to increase viability.

3. Gelation

Figure 29A:
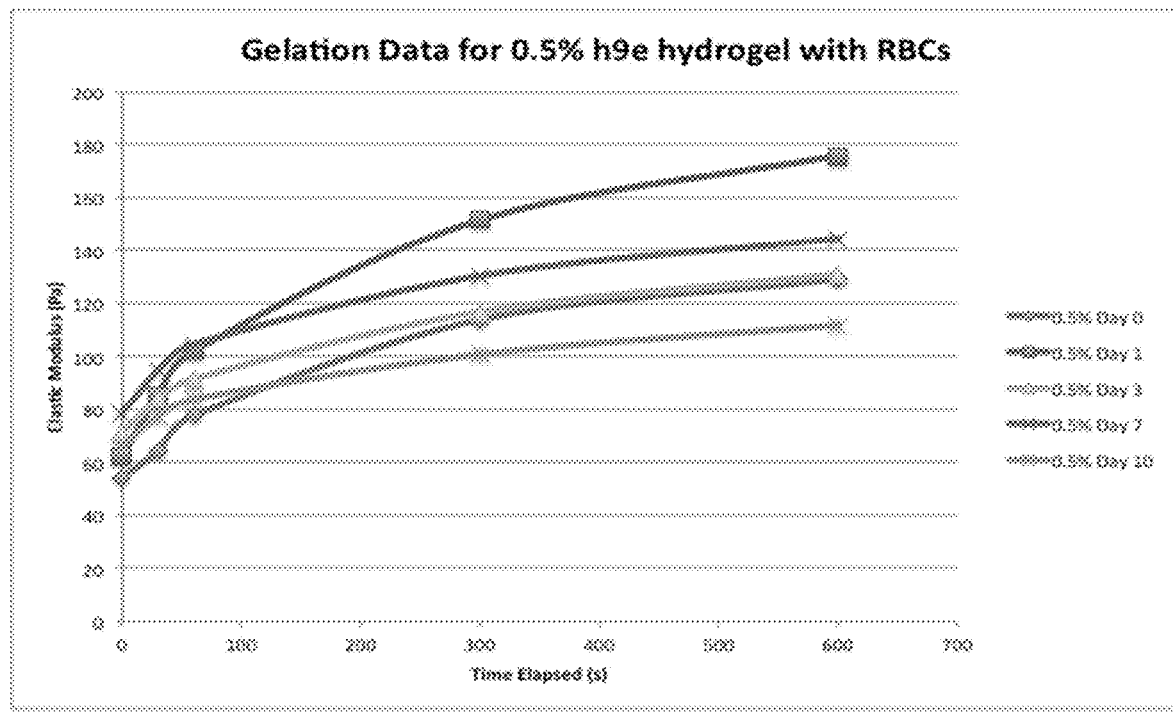
FIG. 29A shows a graph of gelation data displayed in elastic modulus (Pa) over time elapsed (s) on rheometer for hydrogel with h9e concentration of 0.5%. Oscillation tests were performed at 37° C. on Bohlin Instruments Rheometer CVOR 150.
Figure 29B:
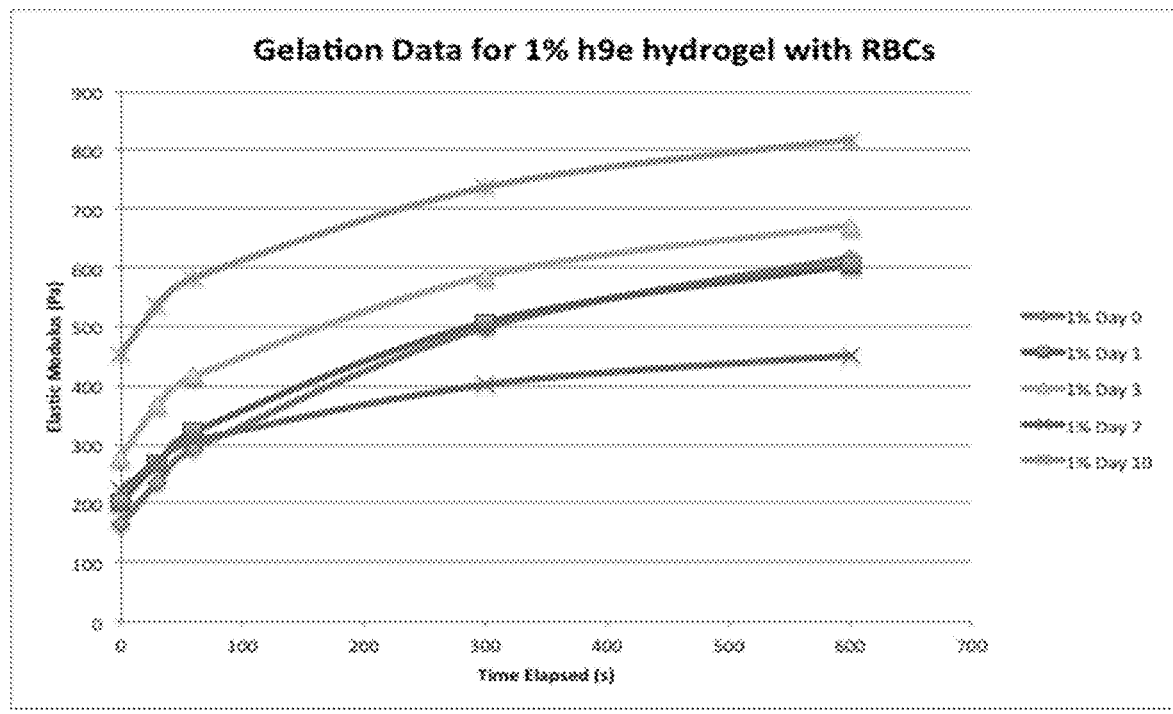
FIG. 29B shows a graph of gelation data displayed in elastic modulus (Pa) over time elapsed (s) on rheometer for hydrogel with h9e concentration of 1%.
Figure 29C:
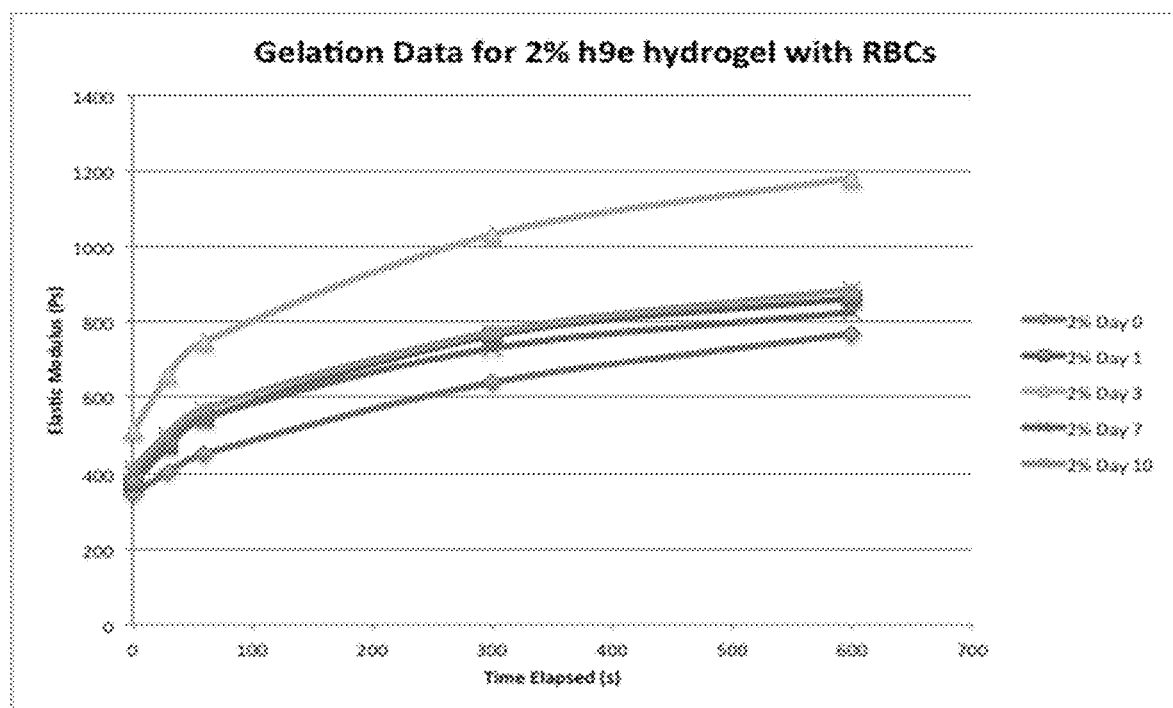
FIG. 29C shows a graph of gelation data displayed in elastic modulus (Pa) over time elapsed (s) on rheometer for hydrogel with h9e concentration of 2%.

Gelation data over the 10 days were plotted on graphs of elastic modulus over time elapsed in FIG. 29A, FIG. 29B, and FIG. 29C, which correspond with hydrogels having h9e concentrations of 0.5%, 1%, and 2%, respectively. The hydrogels exhibited similar gelation profiles over the 10 days. Between hydrogel samples, starting elastic modulus increased with increased concentration of h9e.

Excessive handling and shearing of the hydrogels during sample preparation for each test on each day may explain the inconclusive, varying results. Unexpectedly, there was no clear increase in elastic modulus over the days of evaluation. To avoid these issues, hydrogel samples for rheometer testing may be saved in separate tubes. Additionally, sample sizes of about 300 uL or 400 uL per test may provide more accurate data, as 200 uL was not enough to cover the full measuring plate of the rheometer. In general, gelation profiles seemed to stay constant over the evaluation days.

CONCLUSIONS

Healthy RBC cell morphology decreased over days of evaluation. Viability was maintained similarly in the fresh RBC vial as in the hydrogel over time. The hydrogels were shown to sustain cell viability, and each sample maintained a similar gelation profile over a period of 10 days. WBCs in the samples disrupt viability and imaging data. Also, diluting samples with PBS for testing may have lysed the RBCs and left only WBCs. Notably, gelation or viscosity of h9e hydrogels with RBCs can be as low as 10 Pa at h9e concentrations of <0.05% for artificial blood applications or RBC storage, or as high as up to >1,000 Pa with higher h9e concentrations (>0.5%) for film or molding into shapes for tissue engineering or wounds management.

The invention claimed is:

1. A method of storing and expanding cells, said method comprising
   mixing cells with a self-assembling amphiphilic peptide and a hydrogelation agent, wherein said peptide consists of a terminal hydrophobic region, a central turning region, and a terminal hydrophilic region, to yield a 3-dimensional cell culture comprising said cells embedded in a hydrogel matrix, said hydrogel matrix comprising a 3-dimensional nanofiber matrix comprising said peptide; and
   maintaining said cells in said hydrogel matrix under cell culture conditions.

2. The method of claim 1, wherein said hydrogelation agent is a source of albumin or metal ion.

3. The method of claim 2, wherein said source of albumin is serum-supplemented cell media comprising said cells.

4. The method of claim 2, wherein said metal ion is calcium.

5. The method of claim 1, wherein said maintaining comprises covering said hydrogel matrix with cell media and incubating said hydrogel containing said cells under said cell culture conditions.

6. The method of claim 1, wherein said cells are stem cells or red blood cells.

7. The method of claim 6, wherein said cells are stem cells, further comprising expanding said cells in said hydrogel matrix for at least about 20 passages after said mixing, wherein said stem cells remain in an undifferentiated state.

8. The method of claim 1, said hydrogel matrix further comprising an extracellular matrix ligand, lipid, protein, or biopolymer attached to said hydrophilic region of said peptide.

9. The method of claim 8, wherein said extracellular matrix ligand is selected from the group consisting of GRGD (SEQ ID NO:70), RGDS (SEQ ID NO:71), RGD, HAV, RGDSY (SEQ ID NO:72), and KYRGDS (SEQ ID NO:73).

10. The method of claim 8, wherein said protein is a laminin protein selected from the group consisting of YIGSR (SEQ ID NO:74) and IKVAV (SEQ ID NO:75).

11. The method of claim 1, further comprising isolating said cells from said hydrogel.

12. The method of claim 11, wherein said isolating comprises:
   subjecting said hydrogel to a mechanical force to disrupt the hydrogel matrix;
   diluting said hydrogel with additional cell media; and
   separating said cultured cells from said hydrogel.

13. The method of claim 12, wherein said mechanical force is selected from the group consisting of pipetting, centrifugation, vibration, injection, filtration, spraying, and combinations thereof.

14. The method of claim 1, wherein:
   the terminal hydrophobic region consists of 2 to 15 amino acid residues and contains at least F and I or at least V and I;
   the central turning region consists of 1 to 12 amino acid residues and contains at least G; and
   the terminal hydrophilic region consists of 5 to 20 amino acid residues, where at least three of the residues are G, P, and D.

15. The method of claim 14, wherein the terminal hydrophobic region is FLIVI (SEQ ID NO: 2).

16. The method of claim 14, wherein the central turning region is G, GG, GGG, GGGG (SEQ ID NO:41), or GSII (SEQ ID NO:3).

17. The method of claim 14, wherein said terminal hydrophilic region is GPGGDGPGGD (SEQ ID NO:4) in any order.

18. The method of claim 14, wherein said peptide is FLIVIGSIIGPGGDGPGGD (SEQ ID NO: 1) or a derivative thereof having at least 90% homology with SEQ ID NO: 1 and retaining the functional characteristics thereof.

19. The method of claim 18, wherein said derivative is FLIVIGSIIPGGGDGPGGD (SEQ ID NO:67) or FLIVIGSIIGPGVDPGGAD (SEQ ID NO:68).

* * * * *

SEQUENCE LISTING

```
<160> NUMBER OF SEQ ID NOS: 75

<210> SEQ ID NO 1
<211> LENGTH: 19
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel

<400> SEQUENCE: 1

Phe Leu Ile Val Ile Gly Ser Ile Ile Gly Pro Gly Gly Asp Gly Pro
1               5                   10                  15

Gly Gly Asp

<210> SEQ ID NO 2
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 2

Phe Leu Ile Val Ile
1               5

<210> SEQ ID NO 3
<211> LENGTH: 4
<212> TYPE: PRT
<213> ORGANISM: Artificial Sequence
<220> FEATURE:
<223> OTHER INFORMATION: Peptide turning region derived from the third
      trans-membrane segment of subunit IV in the dihydropyridine
``` sensitive human muscle L-type calcium channel

<400> SEQUENCE: 3

Gly Ser Ile Ile
1

<210> SEQ ID NO 4
<211> LENGTH: 10
<212> TYPE: PRT
<213> ORGANISM: Artificial Sequence
<220> FEATURE:
<223> OTHER INFORMATION: Derivative of spider flagelliform silk protein

<400> SEQUENCE: 4

Gly Pro Gly Gly Asp Gly Pro Gly Gly Asp
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 5

Gly Leu Ile Val Ile
1               5

<210> SEQ ID NO 6
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 6

Pro Leu Ile Val Ile
1               5

<210> SEQ ID NO 7
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 7

Asp Leu Ile Val Ile
1               5

<210> SEQ ID NO 8
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 8

Val Leu Ile Val Ile
1               5

<210> SEQ ID NO 9
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 9

Ile Leu Ile Val Ile
1               5

<210> SEQ ID NO 10
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 10

Leu Leu Ile Val Ile
1               5

<210> SEQ ID NO 11
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 11

Ala Leu Ile Val Ile
1               5

<210> SEQ ID NO 12
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 12

Phe Gly Ile Val Ile
1               5

<210> SEQ ID NO 13
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 13

Phe Pro Ile Val Ile
1               5

<210> SEQ ID NO 14
<211> LENGTH: 5

```
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 14

Phe Asp Ile Val Ile
1               5

<210> SEQ ID NO 15
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 15

Phe Val Ile Val Ile
1               5

<210> SEQ ID NO 16
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 16

Phe Ile Ile Val Ile
1               5

<210> SEQ ID NO 17
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 17

Phe Ala Ile Val Ile
1               5

<210> SEQ ID NO 18
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 18

Phe Leu Gly Val Ile
1               5

<210> SEQ ID NO 19
<211> LENGTH: 5
<212> TYPE: PRT
<213> ORGANISM: Artificial Sequence
<220> FEATURE:
<223> OTHER INFORMATION: Hydrophobic region derived from the third
``` trans-membrane segment of subunit IV in the dihydropyridine
sensitive human muscle L-type calcium channel

<400> SEQUENCE: 19

Phe Leu Pro Val Ile
1               5

<210> SEQ ID NO 20
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 20

Phe Leu Asp Val Ile
1               5

<210> SEQ ID NO 21
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 21

Phe Leu Val Ile Val
1               5

<210> SEQ ID NO 22
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 22

Phe Leu Ala Val Ile
1               5

<210> SEQ ID NO 23
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 23

Phe Leu Ile Gly Ile
1               5

<210> SEQ ID NO 24
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 24

```
Phe Leu Ile Pro Ile
1               5

<210> SEQ ID NO 25
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 25

Phe Leu Ile Asp Ile
1               5

<210> SEQ ID NO 26
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 26

Phe Leu Ile Ile Ile
1               5

<210> SEQ ID NO 27
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 27

Phe Leu Ile Leu Ile
1               5

<210> SEQ ID NO 28
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 28

Phe Leu Ile Ala Ile
1               5

<210> SEQ ID NO 29
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 29

Phe Leu Ile Val Gly
1               5
```

```
<210> SEQ ID NO 30
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 30

Phe Leu Ile Val Pro
1               5

<210> SEQ ID NO 31
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 31

Phe Leu Ile Val Asp
1               5

<210> SEQ ID NO 32
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 32

Phe Leu Ile Val Val
1               5

<210> SEQ ID NO 33
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 33

Phe Leu Ile Val Leu
1               5

<210> SEQ ID NO 34
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 34

Phe Leu Ile Val Ala
1               5

<210> SEQ ID NO 35
<211> LENGTH: 5
<212> TYPE: PRT
```

```
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (3)..(4)
<223> OTHER INFORMATION: each Xaa is individually G, A, D, R, Q, E, S,
      T, K, Y, H, or P

<400> SEQUENCE: 35

Gly Pro Xaa Xaa Asp
1               5

<210> SEQ ID NO 36
<211> LENGTH: 5
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (2)..(3)
<223> OTHER INFORMATION: each Xaa is individually G, A, D, R, Q, E, S,
      T, K, Y, H, or P

<400> SEQUENCE: 36

Gly Xaa Xaa Pro Asp
1               5

<210> SEQ ID NO 37
<211> LENGTH: 5
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (2)..(2)
<223> OTHER INFORMATION: each Xaa is individually G, A, D, R, Q, E, S,
      T, K, Y, H, or P
<220> FEATURE:
<221> NAME/KEY: MISC_FEATURE
<222> LOCATION: (4)..(4)
<223> OTHER INFORMATION: each Xaa is individually G, A, D, R, Q, E, S,
      T, K, Y, H, or P

<400> SEQUENCE: 37

Gly Xaa Pro Xaa Asp
1               5

<210> SEQ ID NO 38
<211> LENGTH: 10
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
<223> OTHER INFORMATION: Xaa is G or A
<220> FEATURE:
<221> NAME/KEY: MISC_FEATURE
<222> LOCATION: (9)..(9)
<223> OTHER INFORMATION: Xaa is G or A

<400> SEQUENCE: 38

Gly Pro Gly Xaa Asp Gly Pro Gly Xaa Asp
1               5                   10

<210> SEQ ID NO 39
<211> LENGTH: 10
```

```
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
<223> OTHER INFORMATION: Xaa is A, G, V, I, or L
<220> FEATURE:
<221> NAME/KEY: MISC_FEATURE
<222> LOCATION: (7)..(7)
<223> OTHER INFORMATION: Xaa is P, A, G, V, I, or L
<220> FEATURE:
<221> NAME/KEY: MISC_FEATURE
<222> LOCATION: (8)..(8)
<223> OTHER INFORMATION: Xaa is individually A, G, V, I, or L
<220> FEATURE:
<221> NAME/KEY: MISC_FEATURE
<222> LOCATION: (9)..(9)
<223> OTHER INFORMATION: Xaa is individually A, G, V, I, or L

<400> SEQUENCE: 39

Gly Pro Gly Xaa Asp Gly Xaa Xaa Xaa Asp
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
<223> OTHER INFORMATION: Xaa is A, G, V, I, or L

<400> SEQUENCE: 40

Gly Pro Gly Xaa Asp
1               5

<210> SEQ ID NO 41
<211> LENGTH: 4
<212> TYPE: PRT
<213> ORGANISM: Artificial Sequence
<220> FEATURE:
<223> OTHER INFORMATION: Peptide turning region

<400> SEQUENCE: 41

Gly Gly Gly Gly
1

<210> SEQ ID NO 42
<211> LENGTH: 4
<212> TYPE: PRT
<213> ORGANISM: Artificial Sequence
<220> FEATURE:
<223> OTHER INFORMATION: Peptide turning region
<220> FEATURE:
<221> NAME/KEY: MISC_FEATURE
<222> LOCATION: (2)..(2)
<223> OTHER INFORMATION: Ser could be Thr
<220> FEATURE:
<221> NAME/KEY: MISC_FEATURE
<222> LOCATION: (3)..(4)
<223> OTHER INFORMATION: each Xaa is individually G, I, V, A, L, or S

<400> SEQUENCE: 42

Gly Ser Xaa Xaa
1

<210> SEQ ID NO 43
```

```
<211> LENGTH: 4
<212> TYPE: PRT
<213> ORGANISM: Artificial Sequence
<220> FEATURE:
<223> OTHER INFORMATION: Peptide turning region
<220> FEATURE:
<221> NAME/KEY: MISC_FEATURE
<222> LOCATION: (1)..(1)
<223> OTHER INFORMATION: each Xaa is individually G, I, V, A, L, or S
<220> FEATURE:
<221> NAME/KEY: MISC_FEATURE
<222> LOCATION: (3)..(3)
<223> OTHER INFORMATION: Ser could be Thr
<220> FEATURE:
<221> NAME/KEY: MISC_FEATURE
<222> LOCATION: (4)..(4)
<223> OTHER INFORMATION: each Xaa is individually G, I, V, A, L, or S

<400> SEQUENCE: 43

Xaa Gly Ser Xaa
1

<210> SEQ ID NO 44
<211> LENGTH: 4
<212> TYPE: PRT
<213> ORGANISM: Artificial Sequence
<220> FEATURE:
<223> OTHER INFORMATION: Peptide turning region
<220> FEATURE:
<221> NAME/KEY: MISC_FEATURE
<222> LOCATION: (1)..(2)
<223> OTHER INFORMATION: each Xaa is individually G, I, V, A, L, or S
<220> FEATURE:
<221> NAME/KEY: MISC_FEATURE
<222> LOCATION: (4)..(4)
<223> OTHER INFORMATION: Ser could be Thr

<400> SEQUENCE: 44

Xaa Xaa Gly Ser
1

<210> SEQ ID NO 45
<211> LENGTH: 4
<212> TYPE: PRT
<213> ORGANISM: Artificial Sequence
<220> FEATURE:
<223> OTHER INFORMATION: Peptide turning region
<220> FEATURE:
<221> NAME/KEY: MISC_FEATURE
<222> LOCATION: (1)..(1)
<223> OTHER INFORMATION: Ser could be Thr
<220> FEATURE:
<221> NAME/KEY: MISC_FEATURE
<222> LOCATION: (3)..(4)
<223> OTHER INFORMATION: each Xaa is individually G, I, V, A, L, or S

<400> SEQUENCE: 45

Ser Gly Xaa Xaa
1

<210> SEQ ID NO 46
<211> LENGTH: 4
<212> TYPE: PRT
<213> ORGANISM: Artificial Sequence
<220> FEATURE:
<223> OTHER INFORMATION: Peptide turning region
<220> FEATURE:
<221> NAME/KEY: MISC_FEATURE
<222> LOCATION: (1)..(1)
<223> OTHER INFORMATION: each Xaa is individually G, I, V, A, L, or S
<220> FEATURE:
<221> NAME/KEY: MISC_FEATURE
<222> LOCATION: (2)..(2)
```

```
<223> OTHER INFORMATION: Ser could be Thr
<220> FEATURE:
<221> NAME/KEY: MISC_FEATURE
<222> LOCATION: (4)..(4)
<223> OTHER INFORMATION: each Xaa is individually G, I, V, A, L, or S

<400> SEQUENCE: 46

Xaa Ser Gly Xaa
1

<210> SEQ ID NO 47
<211> LENGTH: 4
<212> TYPE: PRT
<213> ORGANISM: Artificial Sequence
<220> FEATURE:
<223> OTHER INFORMATION: Peptide turning region
<220> FEATURE:
<221> NAME/KEY: MISC_FEATURE
<222> LOCATION: (1)..(2)
<223> OTHER INFORMATION: each Xaa is individually G, I, V, A, L, or S
<220> FEATURE:
<221> NAME/KEY: MISC_FEATURE
<222> LOCATION: (3)..(3)
<223> OTHER INFORMATION: Ser could be Thr

<400> SEQUENCE: 47

Xaa Xaa Ser Gly
1

<210> SEQ ID NO 48
<211> LENGTH: 4
<212> TYPE: PRT
<213> ORGANISM: Artificial Sequence
<220> FEATURE:
<223> OTHER INFORMATION: Peptide turning region
<220> FEATURE:
<221> NAME/KEY: MISC_FEATURE
<222> LOCATION: (2)..(2)
<223> OTHER INFORMATION: each Xaa is individually G, I, V, A, L, or S
<220> FEATURE:
<221> NAME/KEY: MISC_FEATURE
<222> LOCATION: (3)..(3)
<223> OTHER INFORMATION: Ser could be Thr
<220> FEATURE:
<221> NAME/KEY: MISC_FEATURE
<222> LOCATION: (4)..(4)
<223> OTHER INFORMATION: each Xaa is individually G, I, V, A, L, or S

<400> SEQUENCE: 48

Gly Xaa Ser Xaa
1

<210> SEQ ID NO 49
<211> LENGTH: 4
<212> TYPE: PRT
<213> ORGANISM: Artificial Sequence
<220> FEATURE:
<223> OTHER INFORMATION: Peptide turning region
<220> FEATURE:
<221> NAME/KEY: MISC_FEATURE
<222> LOCATION: (1)..(1)
<223> OTHER INFORMATION: each Xaa is individually G, I, V, A, L, or S
<220> FEATURE:
<221> NAME/KEY: MISC_FEATURE
<222> LOCATION: (3)..(3)
<223> OTHER INFORMATION: each Xaa is individually G, I, V, A, L, or S
<220> FEATURE:
<221> NAME/KEY: MISC_FEATURE
<222> LOCATION: (4)..(4)
<223> OTHER INFORMATION: Ser could be Thr

<400> SEQUENCE: 49
```

Xaa Gly Xaa Ser
1

<210> SEQ ID NO 50
<211> LENGTH: 4
<212> TYPE: PRT
<213> ORGANISM: Artificial Sequence
<220> FEATURE:
<223> OTHER INFORMATION: Peptide turning region
<220> FEATURE:
<221> NAME/KEY: MISC_FEATURE
<222> LOCATION: (1)..(1)
<223> OTHER INFORMATION: Ser could be Thr
<220> FEATURE:
<221> NAME/KEY: MISC_FEATURE
<222> LOCATION: (2)..(2)
<220> FEATURE:
<221> NAME/KEY: MISC_FEATURE
<222> LOCATION: (4)..(4)

<400> SEQUENCE: 50

Ser Xaa Gly Xaa
1

<210> SEQ ID NO 51
<211> LENGTH: 4
<212> TYPE: PRT
<213> ORGANISM: Artificial Sequence
<220> FEATURE:
<223> OTHER INFORMATION: Peptide turning region
<220> FEATURE:
<221> NAME/KEY: MISC_FEATURE
<222> LOCATION: (1)..(1)
<223> OTHER INFORMATION: each Xaa is individually G, I, V, A, L, or S
<220> FEATURE:
<221> NAME/KEY: MISC_FEATURE
<222> LOCATION: (2)..(2)
<223> OTHER INFORMATION: Ser could be Thr
<220> FEATURE:
<221> NAME/KEY: MISC_FEATURE
<222> LOCATION: (3)..(3)
<223> OTHER INFORMATION: each Xaa is individually G, I, V, A, L, or S

<400> SEQUENCE: 51

Xaa Ser Xaa Gly
1

<210> SEQ ID NO 52
<211> LENGTH: 4
<212> TYPE: PRT
<213> ORGANISM: Artificial Sequence
<220> FEATURE:
<223> OTHER INFORMATION: Peptide turning region
<220> FEATURE:
<221> NAME/KEY: MISC_FEATURE
<222> LOCATION: (2)..(3)
<223> OTHER INFORMATION: each Xaa is individually G, I, V, A, L, or S
<220> FEATURE:
<221> NAME/KEY: MISC_FEATURE
<222> LOCATION: (4)..(4)
<223> OTHER INFORMATION: Ser could be Thr

<400> SEQUENCE: 52

Gly Xaa Xaa Ser
1

<210> SEQ ID NO 53
<211> LENGTH: 4
<212> TYPE: PRT
<213> ORGANISM: Artificial Sequence
<220> FEATURE:
<223> OTHER INFORMATION: Peptide turning region

```
<220> FEATURE:
<221> NAME/KEY: MISC_FEATURE
<222> LOCATION: (1)..(1)
<223> OTHER INFORMATION: Ser could be Thr
<220> FEATURE

```
<223> OTHER INFORMATION: Xaa can be K, E, R, Y, or S
<220> FEATURE:
<221> NAME/KEY: MISC_FEATURE
<222> LOCATION: (6)..(9)
<223> OTHER INFORMATION: Any residue can be replaced by W
<220> FEATURE:
<221> NAME/KEY: MISC_FEATURE
<222> LOCATION: (7)..(7)
<223> OTHER INFORMATION: Xaa is P, A, G, V, I, or L
<220> FEATURE:
<221> NAME/KEY: MISC_FEATURE
<222> LOCATION: (8)..(9)
<223> OTHER INFORMATION: each Xaa is K, E, R, Y, or S

<400> SEQUENCE: 56

Gly Pro Gly Xaa Asp Gly Xaa Xaa Xaa Asp
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (5)..(5)
<223> OTHER INFORMATION: Xaa can be K, E, R, Y, or S
<220> FEATURE:
<221> NAME/KEY: MISC_FEATURE
<222> LOCATION: (8)..(8)
<223> OTHER INFORMATION: Xaa is P, A, G, V, I, or L
<220> FEATURE:
<221> NAME/KEY: MISC_FEATURE
<222> LOCATION: (9)..(10)
<223> OTHER INFORMATION: each Xaa is K, E, R, Y, or S

<400> SEQUENCE: 57

Trp Gly Pro Gly Xaa Asp Gly Xaa Xaa Xaa Asp
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
<223> OTHER INFORMATION: Xaa can be K, E, R, Y, or S
<220> FEATURE:
<221> NAME/KEY: MISC_FEATURE
<222> LOCATION: (7)..(7)
<223> OTHER INFORMATION: Xaa is P, A, G, V, I, or L
<220> FEATURE:
<221> NAME/KEY: MISC_FEATURE
<222> LOCATION: (8)..(9)
<223> OTHER INFORMATION: each Xaa is K, E, R, Y, or S

<400> SEQUENCE: 58

Gly Pro Gly Xaa Asp Gly Xaa Xaa Xaa Asp Trp
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
```

```
<223> OTHER INFORMATION: Xaa is A, G, V, I, H, or L
<220> FEATURE:
<221> NAME/KEY: MISC_FEATURE
<222> LOCATION: (7)..(7)
<223> OTHER INFORMATION: Xaa is P, A, G, V, I, H, or L
<220> FEATURE:
<221> NAME/KEY: MISC_FEATURE
<222> LOCATION: (8)..(9)
<223> OTHER INFORMATION: each Xaa is A, G, V, I, H, or L

<400> SEQUENCE: 59

Gly Pro Gly Xaa Asp Gly Xaa Xaa Xaa Asp
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
<223> OTHER INFORMATION: Xaa is A, G, V, I, H, or L
<220> FEATURE:
<221> NAME/KEY: MISC_FEATURE
<222> LOCATION: (7)..(7)
<223> OTHER INFORMATION: Xaa is P, A, G, V, I, H, or L
<220> FEATURE:
<221> NAME/KEY: MISC_FEATURE
<222> LOCATION: (8)..(9)
<223> OTHER INFORMATION: each Xaa is A, G, V, I, H, or L

<400> SEQUENCE: 60

Pro Gly Gly Xaa Asp Gly Xaa Xaa Xaa Asp
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
<223> OTHER INFORMATION: Xaa is A, G, V, I, H, or L
<220> FEATURE:
<221> NAME/KEY: MISC_FEATURE
<222> LOCATION: (7)..(7)
<223> OTHER INFORMATION: Xaa is P, A, G, V, I, H, or L
<220> FEATURE:
<221> NAME/KEY: MISC_FEATURE
<222> LOCATION: (8)..(9)
<223> OTHER INFORMATION: each Xaa is A, G, V, I, H, or L

<400> SEQUENCE: 61

Gly Gly Pro Xaa Asp Gly Xaa Xaa Xaa Asp
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
<223> OTHER INFORMATION: Xaa is A, G, V, I, H, or L
<220> FEATURE:
<221> NAME/KEY: MISC_FEATURE
<222> LOCATION: (7)..(7)
```

```
<223> OTHER INFORMATION: Xaa is P, A, G, V, I, H, or L
<220> FEATURE:
<221> NAME/KEY: MISC_FEATURE
<222> LOCATION: (8)..(9)
<223> OTHER INFORMATION: each Xaa is A, G, V, I, H, or L

<400> SEQUENCE: 62

Gly Pro Gly Xaa Gly Asp Xaa Xaa Xaa Asp
1               5                   10

<210> SEQ ID NO 63
<211> LENGTH: 5
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
<223> OTHER INFORMATION: Xaa is A, G, V, I, L, K, E, S, R, Y, H, or W

<400> SEQUENCE: 63

Gly Pro Gly Xaa Asp
1               5

<210> SEQ ID NO 64
<211> LENGTH: 10
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
<223> OTHER INFORMATION: Xaa is K, E, R, Y, or S
<220> FEATURE:
<221> NAME/KEY: MISC_FEATURE
<222> LOCATION: (5)..(5)
<223> OTHER INFORMATION: D can be K, E, W, or S
<220> FEATURE:
<221> NAME/KEY: MISC_FEATURE
<222> LOCATION: (7)..(4)
<223> OTHER INFORMATION: Xaa is P, A, G, V, I, H, or L
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(9)
<223> OTHER INFORMATION: each Xaa is K, E, R, Y, or S
<220> FEATURE:
<221> NAME/KEY: MISC_FEATURE
<222> LOCATION: (10)..(10)
<223> OTHER INFORMATION: D can be K, E, W, or S

<400> SEQUENCE: 64

Gly Pro Gly Xaa Asp Gly Xaa Xaa Xaa Asp
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (11)..(11)
<223> OTHER INFORMATION: Xaa is G, S, Y, K, E, D, H, V, or A
<220> FEATURE:
<221> NAME/KEY: MISC_FEATURE
<222> LOCATION: (12)..(12)
```

```
<223> OTHER INFORMATION: Xaa is R, Y, S, or E
<220> FEATURE:
<221> NAME/KEY: MISC_FEATURE
<222> LOCATION: (13)..(13)
<223> OTHER INFORMATION: Xaa is A, G, or V
<220> FEATURE:
<221> NAME/KEY: MISC_FEATURE
<222> LOCATION: (14)..(14)
<223> OTHER INFORMATION: Xaa is D, R, S, H, V, or A

<400> SEQUENCE: 65

Gly Pro Gly Gly Asp Gly Pro Gly Gly Asp Xaa Xaa Xaa Xaa
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (9)..(9)
<223> OTHER INFORMATION: Xaa is G, S, Y, K, E, D, H, V, or A
<220> FEATURE:
<221> NAME/KEY: MISC_FEATURE
<222> LOCATION: (10)..(10)
<223> OTHER INFORMATION: Xaa is R, Y, S, or E
<220> FEATURE:
<221> NAME/KEY: MISC_FEATURE
<222> LOCATION: (11)..(11)
<223> OTHER INFORMATION: Xaa is A, G, or V
<220> FEATURE:
<221> NAME/KEY: MISC_FEATURE
<222> LOCATION: (12)..(12)
<223> OTHER INFORMATION: Xaa is D, R, S, H, V, or A

<400> SEQUENCE: 66

Gly Pro Gly Gly Asp Gly Pro Gly Xaa Xaa Xaa Xaa
1               5                   10

<210> SEQ ID NO 67
<211> LENGTH: 19
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel

<400> SEQUENCE: 67

Phe Leu Ile Val Ile Gly Ser Ile Ile Pro Gly Gly Asp Gly Pro
1               5                   10                  15

Gly Gly Asp

<210> SEQ ID NO 68
<211> LENGTH: 19
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel

<400> SEQUENCE: 68

Phe Leu Ile Val Ile Gly Ser Ile Ile Gly Pro Gly Val Asp Pro Gly
1               5                   10                  15

Gly Ala Asp
```

```
<210> SEQ ID NO 69
<211> LENGTH: 23
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel with built-in ECM
      ligand

<400> SEQUENCE: 69

Phe Leu Ile Val Ile Gly Ser Ile Ile Gly Pro Gly Gly Asp Gly Pro
1               5                   10                  15

Gly Gly Asp Gly Arg Gly Asp
            20

<210> SEQ ID NO 70
<211> LENGTH: 4
<212> TYPE: PRT
<213> ORGANISM: Artificial Sequence
<220> FEATURE:
<223> OTHER INFORMATION: Synthetic ligand

<400> SEQUENCE: 70

Gly Arg Gly Asp
1

<210> SEQ ID NO 71
<211> LENGTH: 4
<212> TYPE: PRT
<213> ORGANISM: Artificial Sequence
<220> FEATURE:
<223> OTHER INFORMATION: Synthetic ligand

<400> SEQUENCE: 71

Arg Gly Asp Ser
1

<210> SEQ ID NO 72
<211> LENGTH: 5
<212> TYPE: PRT
<213> ORGANISM: Artificial Sequence
<220> FEATURE:
<223> OTHER INFORMATION: Synthetic ligand

<400> SEQUENCE: 72

Arg Gly Asp Ser Tyr
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic ligand

<400> SEQUENCE: 73

Lys Tyr Arg Gly Asp Ser
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic ligand

<400> SEQUENCE: 74
```

```
Tyr Ile Gly Ser Arg
1               5

<210> SEQ ID NO 75
<211> LENGTH: 5
<212> TYPE: PRT
<213> ORGANISM: Artificial Sequence
<220> FEATURE:
<223> OTHER INFORMATION: Synthetic ligand

<400> SEQUENCE: 75

Ile Lys Val Ala Val
1               5
```